US012637663B2

(12) United States Patent
Murakami et al.

(10) Patent No.: US 12,637,663 B2
(45) Date of Patent: May 26, 2026

(54) ONCOLYTIC VACCINIA VIRUS

(71) Applicant: KM Biologics Co., Ltd., Kumamoto (JP)

(72) Inventors: Toshio Murakami, Kikuchi (JP); Go Okita, Kikuchi (JP); Yui Kamizuru, Kikuchi (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 955 days.

(21) Appl. No.: 17/632,907

(22) PCT Filed: Aug. 7, 2020

(86) PCT No.: PCT/JP2020/030448
§ 371 (c)(1),
(2) Date: Feb. 4, 2022

(87) PCT Pub. No.: WO2021/029385
PCT Pub. Date: Feb. 18, 2021

(65) Prior Publication Data
US 2022/0275347 A1 Sep. 1, 2022

(30) Foreign Application Priority Data
Aug. 9, 2019 (JP) ................................. 2019-147885

(51) Int. Cl.
*C12N 7/00* (2006.01)
*A61K 35/768* (2015.01)
*A61P 35/00* (2006.01)

(52) U.S. Cl.
CPC .............. *C12N 7/00* (2013.01); *A61K 35/768* (2013.01); *A61P 35/00* (2018.01); *C12N 2710/24121* (2013.01); *C12N 2710/24132* (2013.01); *C12N 2710/24162* (2013.01); *C12N 2710/24171* (2013.01)

(58) Field of Classification Search
None
See application file for complete search history.

(56) References Cited

U.S. PATENT DOCUMENTS

| | | |
|---|---|---|
| 2007/0298054 A1 | 12/2007 | Shida et al. |
| 2013/0071430 A1 | 3/2013 | Nakamura et al. |
| 2013/0288338 A1 | 10/2013 | Kohara et al. |
| 2016/0281066 A1 | 9/2016 | Nakamura |

FOREIGN PATENT DOCUMENTS

| | | |
|---|---|---|
| JP | 2006-506974 | 3/2006 |
| JP | 2011-504104 | 2/2011 |
| JP | 2015/076422 | 5/2015 |
| JP | 2016-178945 | 10/2016 |
| JP | 2017-524693 | 8/2017 |
| WO | 2004/014314 | 2/2004 |
| WO | 2009/065546 | 5/2009 |
| WO | 2015/076422 | 5/2015 |
| WO | WO-2015076422 A1 * | 5/2015 ........... A61K 35/768 |
| WO | 2016/009017 | 1/2016 |

OTHER PUBLICATIONS

Potts, et al. EMBO Mol Med. May 2017;9(5):638-654. doi: 10.15252/emmm.201607296. (Year: 2017).*
Blasco, et al. J Virol. Jun. 1993;67(6):3319-25. doi: 10.1128/JVI.67.6.3319-3325.199. (Year: 1993).*
Parkinson et al. Virology. Oct. 1994;204(1):376-90. doi: 10.1006/viro.1994.1542. PMID: 8091668. (Year: 1994).*
Potts K.G et al., "Deletion of F4L (ribonucleotide reductase) in vaccinia virus produces a selective oncolytic virus and promotes anti-tumor immunity with superior safety in bladder cancer models", EMBO Mol Med., 2017, vol. 9, No. 5, pp. 638-654.
International Search Report issued in Sep. 8, 2020 in corresponding International (PCT) Patent Application No. PCT/JP2020-030448.
International Preliminary Report on Patentability issued Feb. 8, 2022 in corresponding International (PCT) Patent Application No. PCT/JP2020/030448.
Beerli C., et al., "Vaccinia virus hijacks EGFR signaling to enhance virus spread through rapid and directed infected cell motility", Nature Microbiology, vol. 4, No. (2), pp. 216-225, 2019.
Schweneker, M., et al., "The vaccinia virus O1 protein is required for sustained activation of extracellular signal-regulated kinase 1/2 and promotes viral virulence", Journal of Virology, vol. 86, No. (4), pp. 2323-2336, 2012.
Blasco, R., et al., "Dissociation of progeny vaccinia virus from the cell membrane is regulated by a viral envelope glycoprotein: Effect of a point mutation in the lectin homology domain of the A34R gene", Journal of Virology, vol. 67, No. (6), pp. 3319-3325, 1993.
Downs-Canner, S., et al., "Phase 1 study of intravenous oncolytic poxvirus (vvDD) in patients with advanced solid cancers", Molecular Therapy, vol. 24, No. (8), pp. 1492-1501, 2016.
Mell, L., et al., "Phase I trial of intravenous oncolytic vaccinia virus (GL-ONC1) with cisplatin and radiotherapy in patients with locoregionally advanced head and neck carcinoma", Clinical Cancer Research, vol. 23, No. (19), pp. 5696-5702, 2017.

(Continued)

*Primary Examiner* — Benjamin P Blumel
*Assistant Examiner* — Jeffrey Mark Sifford
(74) *Attorney, Agent, or Firm* — Wenderoth, Lind & Ponack, L.L.P.

(57) ABSTRACT

Provided is an oncolytic virus having both improved safety and productivity. Provided are: a conditionally replicating vaccinia virus which lacks the functions of a vaccinia virus growth factor (VGF), an extracellular signal-regulated kinase (ERK) activation protein, and a ribonucleotide reductase (RNR), is not replicated in a normal cell, is selectively replicable in a proliferative cell, and has improved safety; and a conditionally replicating vaccinia virus which lacks the functions of a VGF, an ERK activation protein, and an RNR, is not replicated in a normal cell, is selectively replicable in a proliferative cell, and has improved safety and productivity, and in which a gene encoding an extracellular enveloped virus (EEV)-related protein is substituted with a gene corresponding to another vaccinia virus strain having a high EEV-producing ability.

11 Claims, 15 Drawing Sheets

Specification includes a Sequence Listing.

(56) References Cited

OTHER PUBLICATIONS

McIntosh A., "Vaccinia virus glycoprotein A34R is required for infectivity of extracellular enveloped virus", Journal of Virology, vol. 70, No. (1), pp. 272-281, 1996.

Ferguson M. S., et al., "Systemic delivery of oncolytic viruses: Hopes and hurdles", Advances in Virology, vol. 2012, Article ID 805629, 2012, 14 pages.

Badrinath N, et al., "Viruses as nanomedicine for cancer", International Journal of Nanomedicine, vol. 11, pp. 4835-4847, 2016.

Bernet J., et al., "Viral mimicry of the complement system", Journal of Biosciences, vol. 28, No. (3), pp. 249-264, 2003.

Dehaven B. C., et al., "The vaccinia virus A56 protein: a multi-functional transmembrane glycoprotein that anchors two secreted viral proteins", Journal of General Virology, vol. 92, pp. 1971-1980, 2011.

Chung, C-S. et al., "A27L protein mediates vaccinia virus interaction with cell surface heparan sulfate", Journal of Virology, vol. 72, No. (2), pp. 1577-1585, 1998.

Gammon, D. B., et al., "Vaccinia virus-encoded ribonucleotide reductase subunits are differentially required for replication and pathogenesis", PLOS Pathogens, vol. 6, No. (7), e1000984, 2010, 20 pages.

Aye Y., et al., "Ribonucleotide reductase and cancer: biological mechanisms and targeted therapies", Oncogene, vol. 34, No. (16), pp. 2011-2021, 2015.

Engstrom, Y., et al., "Cell cycle-dependent expression of mammalian ribonucleotide reductase", The Journal of Biological Chemistry, vol. 260, No. (16), pp. 9114-9116, 1985.

Torii, S., et al., "ERK MAP kinase in G1 cell cycle progression and cancer", Cancer Science, vol. 97, No. (8), pp. 697-702, 2006.

Morikawa, S. et al., "An Attenuated LC16m8 smallpox vaccine: analysis of full-genome sequence and induction of immune protection", Journal of Virology, vol. 79, No. (18), pp. 11873-11891, 2005.

Smith G.L. et al., "The formation and function of extracellular enveloped vaccinia virus", Journal of General Virology, vol. 83 (Pt 12), pp. 2915-2931, 2002.

Guo, Z.S., et al., "Vaccinia virus-mediated cancer immunotherapy: cancer vaccines and oncolytics", Journal for Immuno Therapy of Cancer, vol. 7, No. 6, 2019, 21 pages.

Extended European Search Report issued Aug. 28, 2023 in corresponding European Patent Application No. 20853185.5.

Goebel, S.J. et al., "The complete DNA Sequence of Vaccinia Virus", Virology, 1990, vol. 179, No. 1, pp. 247-266.

McCart, J.A. et al., "Systemic Cancer Therapy with a Tumor-selective Vaccinia Virus Mutant Lacking Thymidine Kinase and Vaccinia Growth Factor Genes", Cancer Research, 2001, vol. 61, pp. 8751-8757.

* cited by examiner

Fig. 1

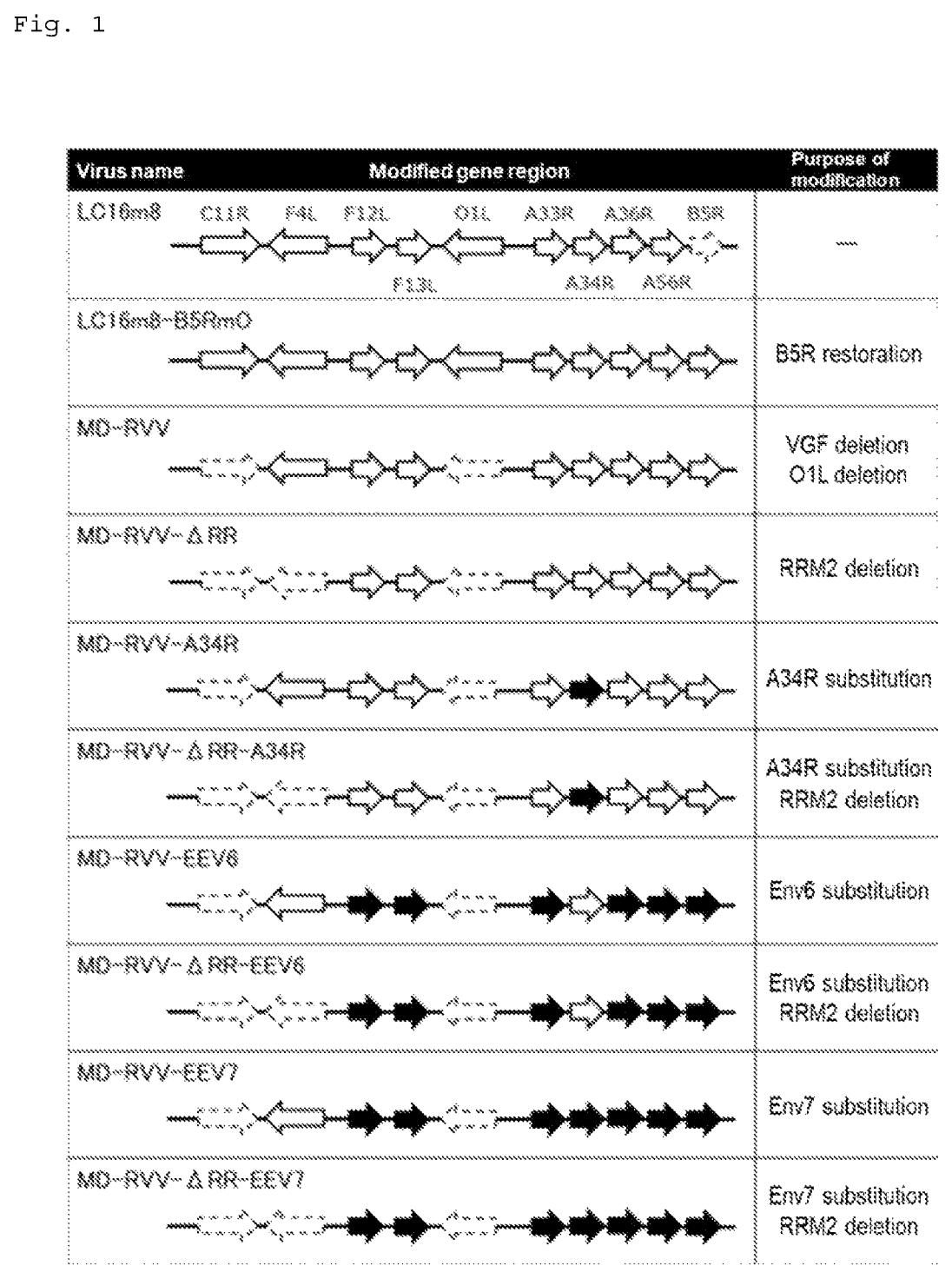

| Virus name | Modified gene region | Purpose of modification |
|---|---|---|
| LC16m8 | C11R F4L F12L O1L A33R A36R B5R / F13L A34R A56R | --- |
| LC16m8-B5RmO | | B5R restoration |
| MD-RVV | | VGF deletion O1L deletion |
| MD-RVV-ΔRR | | RRM2 deletion |
| MD-RVV-A34R | | A34R substitution |
| MD-RVV-ΔRR-A34R | | A34R substitution RRM2 deletion |
| MD-RVV-EEV6 | | Env6 substitution |
| MD-RVV-ΔRR-EEV6 | | Env6 substitution RRM2 deletion |
| MD-RVV-EEV7 | | Env7 substitution |
| MD-RVV-ΔRR-EEV7 | | Env7 substitution RRM2 deletion |

[Fig.3]
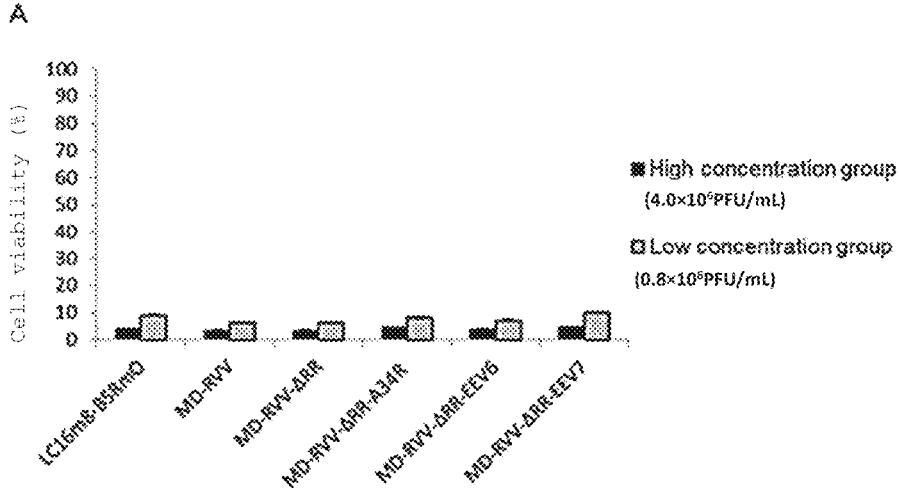
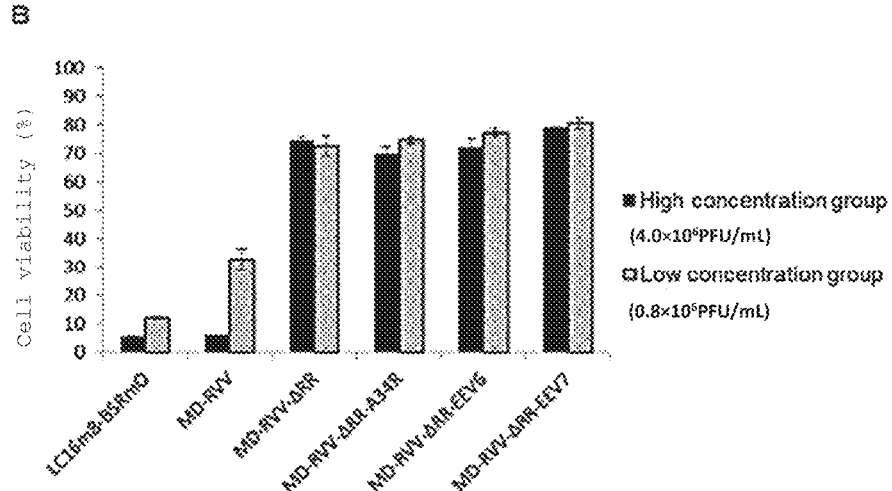

Fig. 7
A
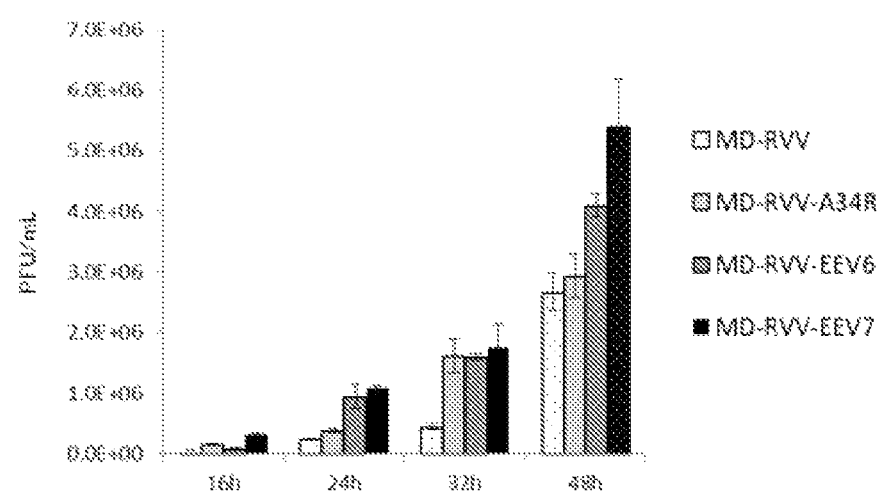
B
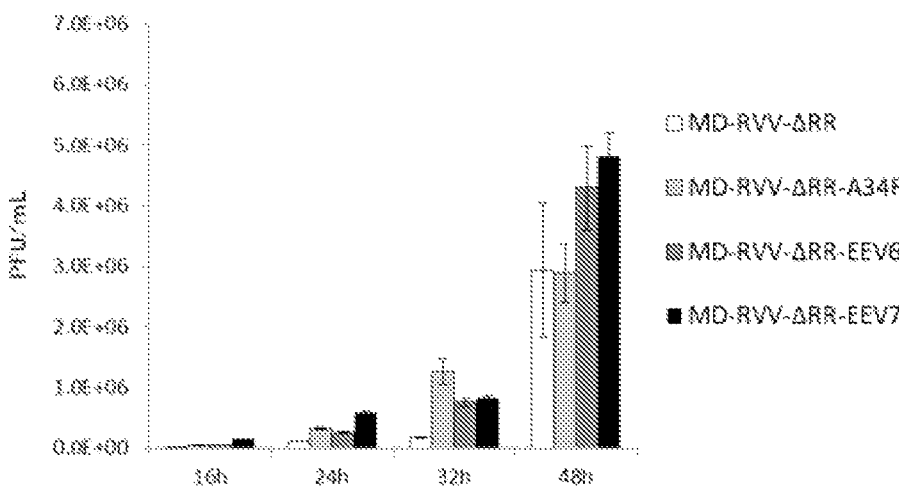

[Fig.8]
A
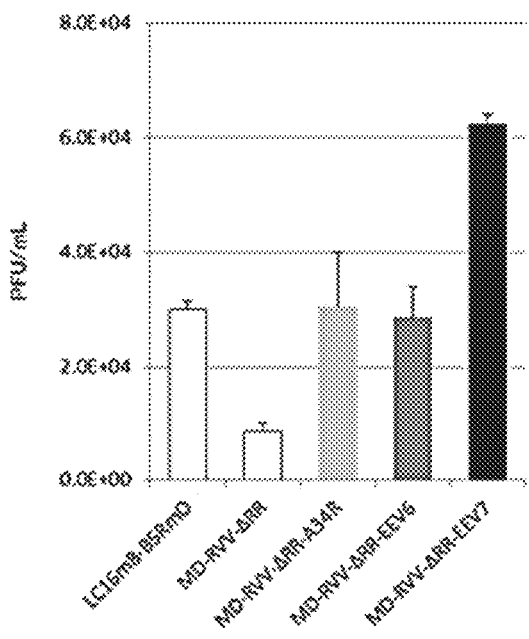
B
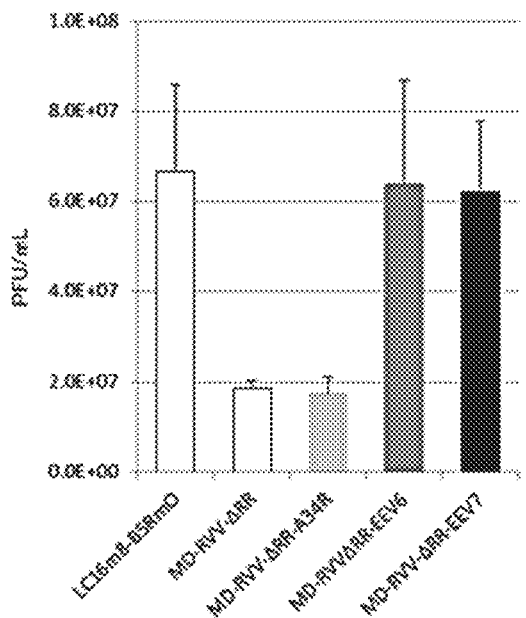

[Fig. 9]
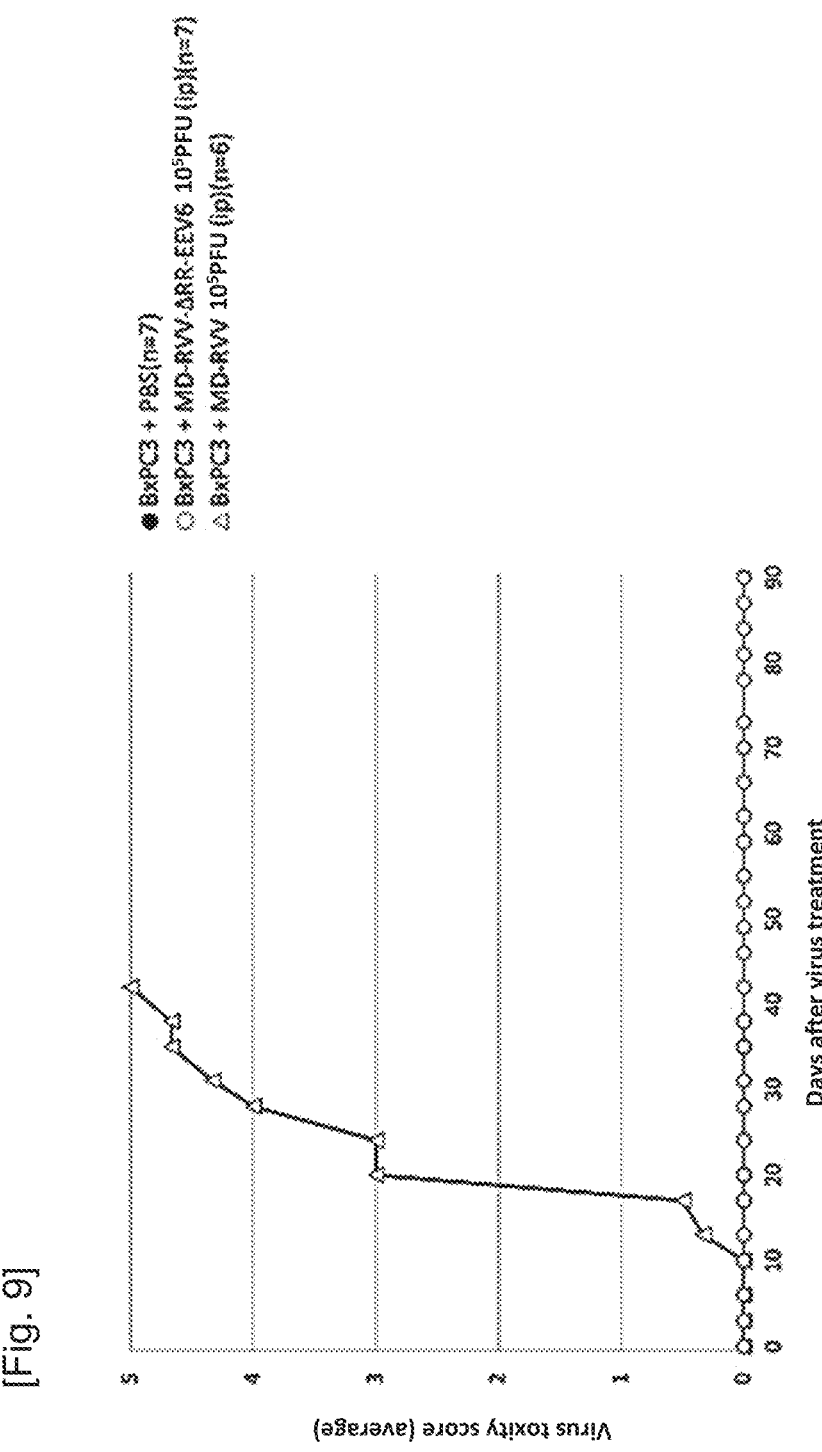

[Fig. 10]
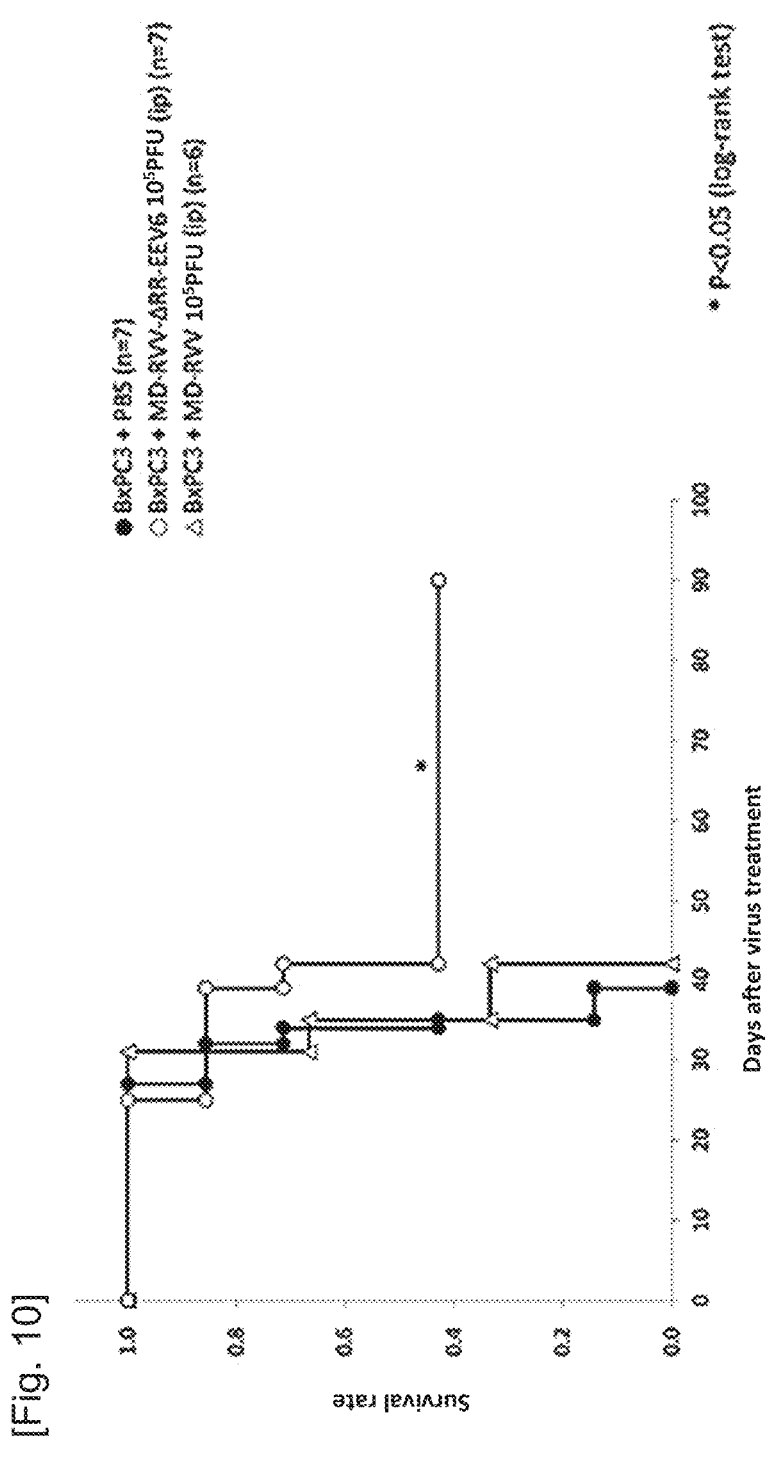

[Fig. 11]
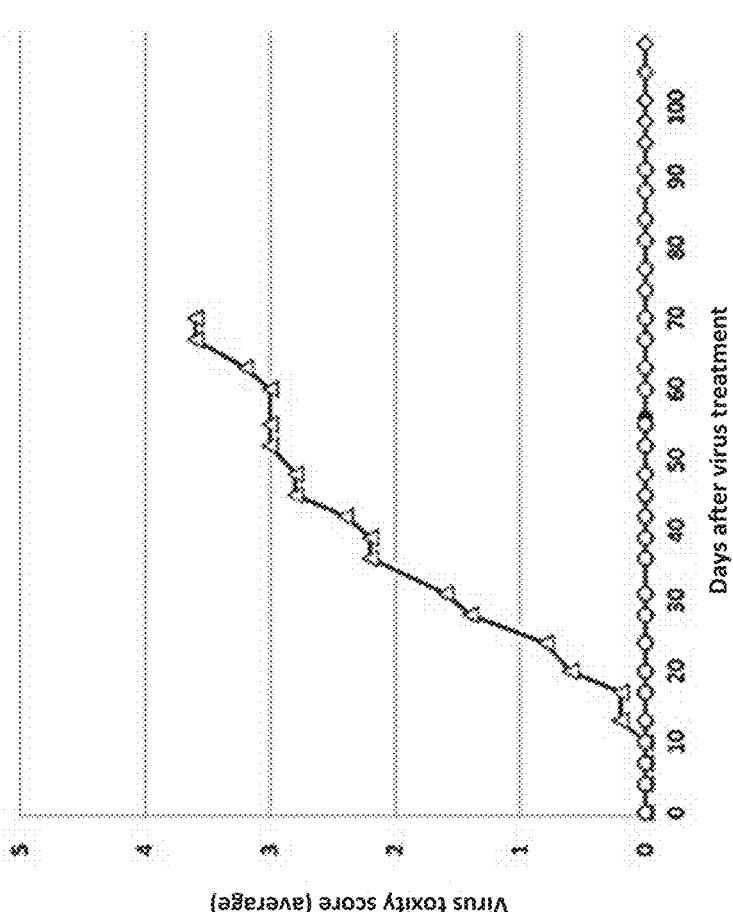

[Fig. 12]
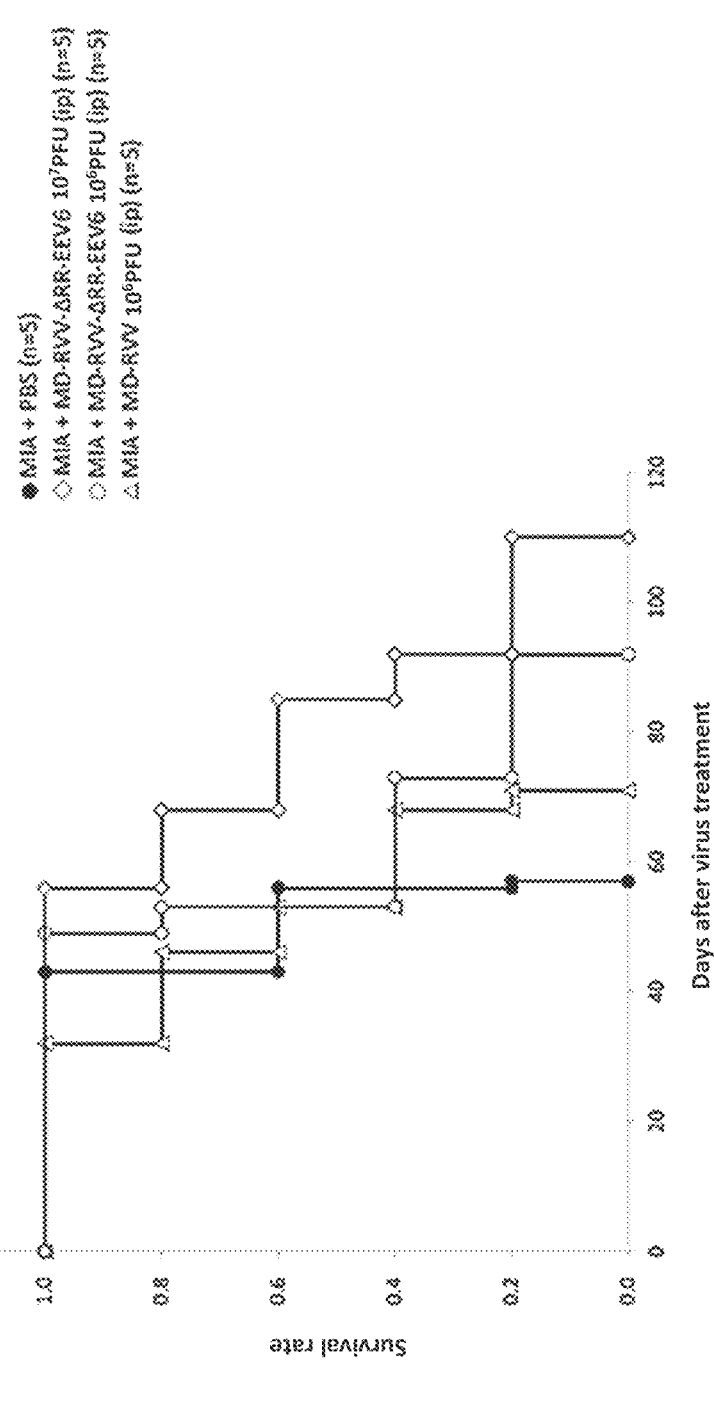

Figure 14:
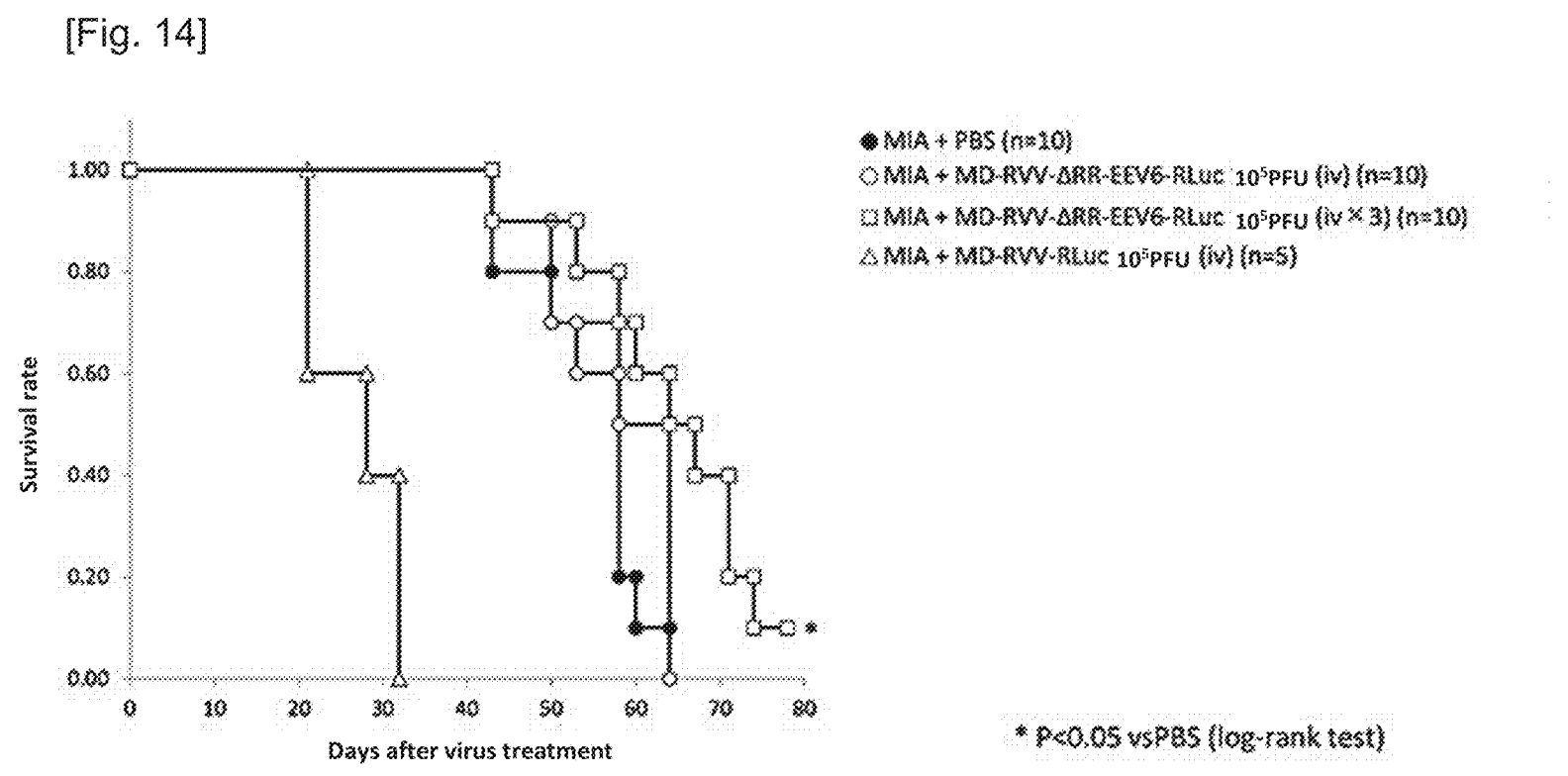

● MIA + PBS (n=10)
○ MIA + MD-RVV-ΔRR-EEV6-RLuc 10⁵PFU (iv) (n=10)
□ MIA + MD-RVV-ΔRR-EEV6-RLuc 10⁵PFU (iv × 3) (n=10)
△ MIA + MD-RVV-RLuc 10⁵PFU (iv) (n=5)

* P<0.05 vsPBS (log-rank test)

Survival rate

Days after virus treatment

[Fig. 15]
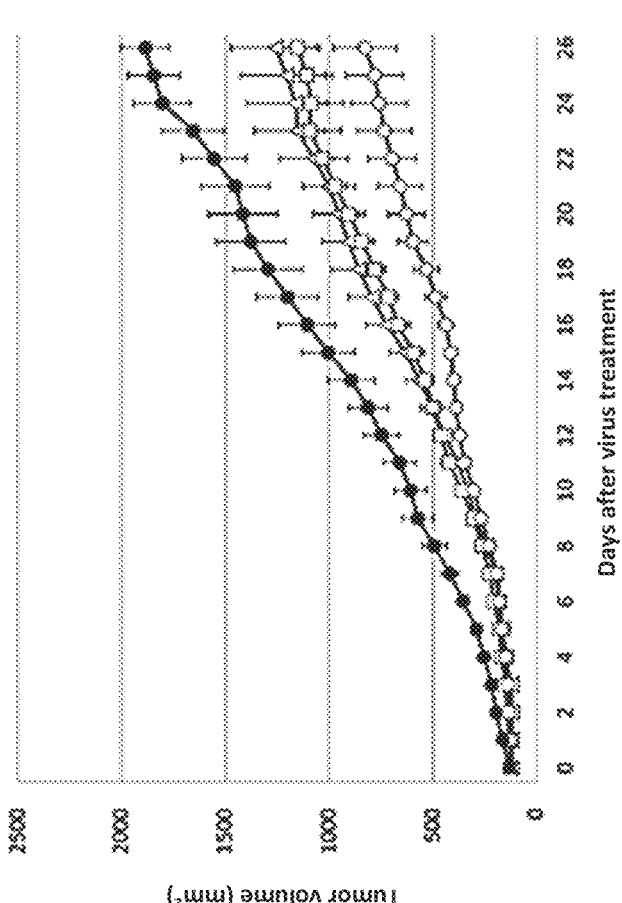

```
                        SEQUENCE LISTING

<160> NUMBER OF SEQ ID NOS: 63

<210> SEQ ID NO 1
<211> LENGTH: 30
<212> TYPE: DNA
<213> ORGANISM: Artificial Sequence
<220> FEATURE:
<223> OTHER INFORMATION: TK1 primer Fw

<400> SEQUENCE: 1
cggggtacca taaattagaa gccgtgggtc                                   30

<210> SEQ ID NO 2
<211> LENGTH: 40
<212> TYPE: DNA
<213> ORGANISM: Artificial Sequence
<220> FEATURE:
<223> OTHER INFORMATION: TK1 primer Re

<400> SEQUENCE: 2
ccttaattaa gaaaaatatt atgagtcgat gtaacacttt                        40

<210> SEQ ID NO 3
<211> LENGTH: 35
<212> TYPE: DNA
<213> ORGANISM: Artificial Sequence
<220> FEATURE:
<223> OTHER INFORMATION: TK2 primer Fw

<400> SEQUENCE: 3
ccttaattaa tatatttttt atctaaaaaa ctaaa                             35

<210> SEQ ID NO 4
<211> LENGTH: 33
<212> TYPE: DNA
<213> ORGANISM: Artificial Sequence
<220> FEATURE:
<223> OTHER INFORMATION: TK2 primer Re

<400> SEQUENCE: 4
gctctagacg gtagtatatc tcagtagtac gtt                               33

<210> SEQ ID NO 5
<211> LENGTH: 4458
<212> TYPE: DNA
<213> ORGANISM: Artificial Sequence
<220> FEATURE:
<223> OTHER INFORMATION: pUCIDT-KAN-op7.5+EGFP

<400> SEQUENCE: 5
cccccccccc catgacatta acctataaaa ataggcgtat cacgaggcca gcttgggaaa    60
ccataagacc gagatagagt tgagtgttgt tccagtttgg aacaagagtc cactattaaa   120
gaacgtggac tccaacgtca aagggcgaaa aaccgtctat cagggcgatg gcccactacg   180
tgaaccatca cccaaatcaa gttttttggg gtcgaggtgc cgtaaagcac taaatcggaa   240
ccctaaaggg agcccccgat ttagagcttg acggggaaag ccggcgaacg tggcgagaaa   300
ggaagggaag aaagcgaaag gagcgggcgc taagcgctg gcaagtgtag cggtcacgct   360
gcgcgtaacc accacacccg ccgcgcttaa tgcgccgcta cagggcgcgt actatggttg   420
```

```
ctttgacgta tgcggtgtga aataccgcac agatgcgtaa ggagaaaata ccgcatcagg      480
cgccattcgc cattcaggct gcgcaactgt tgggaagggc gatcggtgcg ggcctcttcg      540
ctattacgcc agctggcgaa aggggatgt gctgcaaggc gattaagttg ggtaacgcca       600
gggttttccc agtcacgacg ttgtaaaacg acggccagtg aattgatcga gatcgtgatc      660
cggatcaaga tccagatcga attccatggt ctcaactttc acaggctgtc gccgtgctca      720
tttgattgaa ccggtcagct acggttcgaa tgcgtcagcg tcagcgattt aattaaggat      780
ccgcggccgc tagccgacat atactatata gtaataccaa tactcaagac tacgaaactg      840
atacaatctc ttatcatgtg ggtaatgttc tcgatgtcga atagccatat gccggtagtt      900
gcgatataca taaactgatc actaattcca aacccacccg cttttatag taagttttt      960 acccataaat aataaataca ataattaatt tctcgtaaaa gtagaaaata tattctaatt     1020
tattgcacgg taaggaagta gaatcataaa gaacagtgac ggatcgctag caccggtcgc     1080
caccatggtg agcaagggcg aggagctgtt caccgggggtg gtgcccatcc tggtcgagct     1140
ggacggcgac gtaaacggcc acaagttcag cgtgtccggc gagggcgagg gcgatgccac     1200
ctacggcaag ctgaccctga agttcatctg caccaccggc aagctgcccg tgccctggcc     1260 cacccctcgtg accaccctga cctacggcgt gcagtgcttc agccgctacc ccgaccacat     1320
gaagcagcac gacttcttca gtccgccat gcccgaaggc tacgtccagg agcgcaccat      1380
cttcttcaag gacgacggca actacaagac ccgcgccgag gtgaagttcg agggcgacac     1440
cctggtgaac cgcatcgagc tgaagggcat cgacttcaag gaggacggca acatcctggg     1500
gcacaagctg gagtacaact acaacagcca caacgtctat atcatggccg acaagcagaa     1560
gaacggcatc aaggtgaact tcaagatccg ccacaacatc gaggacggca gcgtgcagct     1620
cgccgaccac taccagcaga acacccccat cggcgacggc cccgtgctgc tgcccgacaa     1680
ccactacctg agcacccagt ccgccctgag caaagacccc aacgagaagc gcgatcacat     1740
ggtcctgctg gagttcgtga ccgccgccgg gatcactctc ggcatggacg agctgtacaa     1800
gtaaggatcc ttaattaaat cggcagctac ggtaagctaa ggtcgtcagc atcagaaggg     1860
atcttgctgc cgcccgaaag gagataggat ccaagcttga tccagatccc gatctggatc     1920
cagatccgga tcgcagcttg gcgtaatcat ggtcatagct gtttcctgtg tgaaattgtt     1980
atccgctcac aattccacac aacatacgag ccggaagcat aaagtgtaaa gcctggggtg     2040
cctaatgagt gagctaactc acattaattg cgttgcgctc actgcccgct ttccagtcgg     2100
gaaacctgtc gtgccagctg cattaatgaa tcggccaacg cgcggggaga ggcggtttgc     2160
gtattgggcg ctcttccgct tcctcgctca ctgactcgct gcgctcggtc gttcggctgc     2220
ggcgagcggt atcagctcac tcaaaggcgg taatacggtt atccacagaa tcaggggata     2280
acgcaggaaa gaacatgtga gcaaaaggcc agcaaaaggc caggaaccgt aaaaaggccg     2340
cgttgctggc gtttttccat aggctccgcc ccctgacga gcatcacaaa aatcgacgct      2400
caagtcagag gtggcgaaac ccgacaggac tataaagata ccaggcgttt cccccctggaa    2460 gctccctcgt cgctctcctg ttccgaccct gccgcttacc ggatacctgt ccgcctttct     2520
cccttcggga agcgtggcgc tttctcatag ctcacgctgt aggtatctca gttcggtgta     2580
ggtcgttcgc tccaagctgg gctgtgtgca cgaacccccc gttcagcccg accgctgcgc     2640
cttatccggg aactatcgtc ttgagtccaa cccggtaaga cacgacttat cgccactggc     2700
agcagccact ggtaacagga ttagcagagc gaggtatgta ggcggtgcta cagagttctt     2760
```

-continued

```
gaagtggtgg cctaactacg gctacactag aagaacagta tttggtatct gcgctctgct      2820
gaagccagtt accttcggaa aaagagttgg tagctcttga tccggcaaac aaaccaccgc      2880
tggtagcggt ggtttttttg tttgcaagca gcagattacg cgcagaaaaa aaggatctca      2940
agaagatcct ttgatctttt ctacggggtc tgacgctcag tggaacgaaa actcacgtta      3000
agggattttg gtcatgagat tatcaaaaag gatcttcacc tagatccttt taaattaaaa      3060
atgaagtttt aaatcaatct aaagtatata tgagtaaact tggtctgaca gttaccaatg      3120
cttaatcagt gaggcaccta tctcagcgat ctgtctattt cgttcatcca tagttgcctg      3180
actccccgtc gtgtagataa ctacgatacg ggagggctta ccatctggcc ccagtgctgc      3240
aatgataccg cagcttggga aaccataaga gctgaagcca gttaccttcg gaaaaagagt      3300
tggtagctct tgatccggca aacaaaccac cgctggtagc ggtggttttt ttgtttgcaa      3360
gcagcagatt acgcgcagaa aaaaggatc tcaagaagat cctttgatct tttctacggg      3420
gtctgacgct cagtggaacg aaaactcacg ttaagggatt ttggtcatga gcttgcgccg      3480
tcccgtcaag tcagcgtaat gctctgccag tgttacaacc aattaaccaa ttctgattag      3540
aaaaactcat cgagcatcaa atgaaactgc aatttattca catcaggatt atcaatacca      3600
tatttttgaa aaagccgttt ctgtaatgaa ggagaaaact caccgaggca gttccatagg      3660
atggcaagat cctggtatcg gtctgcgatt ccgactcgtc caacatcaat acaacctatt      3720
aatttcccct cgtcaaaaat aaggttatca agtgagaaat caccatgagt gacgactgaa      3780
tccggtgaga atggcaaaag tttatgcatt tctttccaga cttgttcaac aggccagcca      3840
ttacgctcgt catcaaaatc actcgcatca accaaaccgt tattcattcg tgattgcgcc      3900
tgagcaagac gaaatacgcg atcgctgtta aaaggacaat tacaaacagg aatcgaatgc      3960
aaccggcgca ggaacactgc cagcgcatca acaatatttt cacctgaatc aggatattct      4020
tctaatacct ggaatgctgt ttttccgggg atcgcagtgg tgagtaacca tgcatcatca      4080
ggagtacgga taaaatgctt gatggtcgga agaggcataa attccgtcag ccagtttagt      4140
ctgaccatct catctgtaac atcattggca acgctacctt tgccatgttt cagaaacaac      4200
tctggcgcat cgggcttccc atacaagcga tagattgtcg cacctgattg cccgacatta      4260
tcgcgagccc atttataccc atataaatca gcatccatgt tggaatttaa tcgcggcctc      4320
gacgtttccc gttgaatatg gctcataaca ccccttgtat tactgtttat gtaagcagac      4380
agttttattg ttcatgatga tatattttta tcttgtgcaa tgtaacatca gagatttttga      4440 gacacaacgt ggctttcc                                                    4458
```

<210> SEQ ID NO 6
<211> LENGTH: 4153
<212> TYPE: DNA
<213> ORGANISM: Artificial Sequence
<220> FEATURE:
<223> OTHER INFORMATION: BACgfp removing cassette

<400> SEQUENCE: 6

```
ctgcaggtca ctgttgtaat tcattaagca ttctgccgac atggaagcca tcacaaacgg        60
catgatgaac ctgaatcgcc agcggcatca gcaccttgtc gccttgcgta taatatttgc       120
ccatggtgaa aacggggggcg aagaagttgt ccatattggc cacgtttaaa tcaaaactgg      180
tgaaactcac ccagggattg gctgagacga aaaacatatt ctcaataaac cctttaggga      240
aataggccag gttttcaccg taacacgcca tcttgcgata tatatgtgt agaaactgcc       300 ggaaatcgtc gtggtattca ctccagagcg atgaaaacgt ttcagtttgc tcatggaaaa      360
```

-continued

```
cggtgtaaca agggtgaaca ctatcccata tcaccagctc accgtctttc attgccatac    420
ggaattccgg atgagcattc atcaggcggg caagaatgtg aataaaggcc ggataaaact    480
tgtgcttatt tttctttacg gtctttaaaa aggccgtaat atccagctga acggtctggt    540
tataggtaca ttgagcaact gactgaaatg cctcaaaatg ttctttacga tgccattggg    600
atatatcaac ggtggtatat ccagtgattt ttttctccat tttagcttcc ttagctcctg    660
aaaatctcga taactcaaaa aatacgcccg gtagtgatct tatttcatta tggtgaaagt    720
tggaacctct tacgtgccga tcaacgtctc attttcgcca aaagttggcc cagggcttcc    780
cggtatcaac agggacacca ggatttattt attctgcgaa gtgatcttcc gtcacaggta    840
tttattcgcc gcggaggttg taacatttta ttaccgtgtg ggatataaaa gtccttgatc    900
cattgatctg aaacgggca tctccattta agactagatg ccacggggtt taaaatacta    960
atcatgacat tttgtagagc gtaattactt agtaaatccg ccgtactagg ttcatttcct   1020
cctcgtttgg atcttacatc agaaattaaa ataatcttag aaggatgcag ttgtttttg    1080 atggatcgta gatattcctc atcaacgaac cgagtcacta gagtcacatc acgcaatcca   1140
tttaaaatag gatcatgatg gcggccgtca attagcatcc atttgatgat cactcctaaa   1200
ttatagaaat gatctctcaa ataacgtata tgtgtaccgg gagcagatcc tatatacact   1260
acggtggcac catctaatat accgtgtcgc tgtaacttac taagaaaaaa taattctcct   1320
agtaatagtt ttaactgtcc ttgatacggc agttttttg cgacctcatt tgcactttct    1380
ggttcgtaat ctaactcatt atcaatttcc tcaaaataca taaacggttt atctaacgac   1440
acaacatcca ttttttaagta ttatattaaa atttaatcaa tgtttatttt tagtttttta   1500
gataaaaaat ataatattat gagtcgatgt aacactttct acacaccgat tgatacatat   1560
cattacctcc tattatttct atctcggttt cctcacccaa tcgtttagaa aaggaagcct   1620
ccttaaagca tttcatacac acagcagtta gttttaccac catttcagat aatggaataa   1680
gattcaaaat attattaaac ggtttacgtt gaaatgtccc atcgagtgcg gctactataa   1740 ctattttcc ttcgtttgcc atacgctcac agaattcaac aatgtctgga aagaactgtc   1800
cttcatcgat acctatcacg gagaaatctg taattgattc caagacatcg catagtttag   1860
ttgcttccaa tgcttcaaaa ttattcttat catgcgtcca tagtcccgtt ccgtatctat   1920
tatcgttaga atattttata gtcacgcatt tatattgagc tatttgataa cgtctaactc   1980
gtctaattaa ttctgtactt ttacctgaaa acatggggcc gattatcaac tgaatatgtc   2040
cgccgttcat gatgacaata aagaattaat tattgttcac tttattcgac tttaatatat   2100
ccatcacgtt agaaaatgcg atatcacgac gaggatctat gtatctaata ggatctattg   2160
cggtggtagc tagagaggat tctttttga atcgcatcaa actaatcaca aagtccgcgg   2220
cgataagctc atggagcggc gtaaccgtcg cacaggaagg acagagaaag tagggataac   2280
agggtaatcg atttattcaa caaagccacg ttgtgtctca aaatctctga tgttacattg   2340
cacaagataa aaatatatca tcatgaacaa taaaactgtc tgcttacata aacagtaata   2400 caagggggtgt tatgagccat attcaacggg aaacgtcttg ctcgaggccg cgattaaatt   2460
ccaacatgga tgctgattta tatgggtata aatgggctcg cgataatgtc gggcaatcag   2520
gtgcgacaat ctatcgattg tatgggaagc ccgatgcgcc agagttgttt ctgaaacatg   2580
gcaaaggtag cgttgccaat gatgttacag atgagatggt cagactaaac tggctgacgg   2640
aatttatgcc tcttccgacc atcaagcatt ttatccgtac tcctgatgat gcatggttac   2700
```

-continued

```
tcaccactgc gatccccggg aaaacagcat tccaggtatt agaagaatat cctgattcag    2760
gtgaaaatat tgttgatgcg ctggcagtgt tcctgcgccg gttgcattcg attcctgttt    2820
gtaattgtcc ttttaacagc gatcgcgtat ttcgtctcgc tcaggcgcaa tcacgaatga    2880
ataacggttt ggttgatgcg agtgattttg atgacgagcg taatggctgg cctgttgaac    2940
aagtctggaa agaaatgcat aagcttttgc cattctcacc ggattcagtc gtcactcatg    3000
gtgatttctc acttgataac cttatttttg acgaggggaa attaataggt tgtattgatg    3060
ttggacgagt cggaatcgca gaccgatacc aggatcttgc catcctatgg aactgcctcg    3120
gtgagttttc tccttcatta cagaaacggc tttttcaaaa atatggtatt gataatcctg    3180
atatgaataa attgcagttt catttgatgc tcgatgagtt tttctaatca gaattggtta    3240
attggttgta acactggccg ataagctcat ggagcggcgt aaccgtcgca caggaaggac    3300
agagaaagcg cggatctggg aagtgacgga cagaacggtc aggacctgga ttggggaggc    3360
ggttgccgcc gctgctgctg acggtgtgac gttctctgtt ccggtcacac cacatacgtt    3420
ccgccattcc tatgcgatgc acatgctgta tgccggtata ccgctgaaag ttctgcaaag    3480
cctgatggga cataagtcca tcagttcaac ggaagtctac acgaaggttt ttgcgctgga    3540
tgtggctgcc cggcaccggg tgcagtttgc gatgccggag tctgatgcgg ttgcgatgct    3600
gaaacaatta tcctgagaat aaatgccttg gcctttatat ggaaatgtgg aactgagtgg    3660
atatgctgtt tttgtctgtt aaacagagaa gctggctgtt atccactgag aagcgaacga    3720
aacagtcggg aaaatctccc attatcgtag agatccgcat tattaatctc aggagcctgt    3780
gtagcgttta taggaagtag tgttctgtca tgatgcctgc aagcggtaac gaaaacgatt    3840
tgaatatgcc ttcaggaaca atagaaatct tcgtgcggtg ttacgttgaa gtggagcgga    3900
ttatgtcagc aatggacaga acaacctaat gaacacagaa ccatgatgtg gtctgtcctt    3960
ttacagccag tagtgctcgc cgcagtcgag cgacagggcg aagccctcga gtgagcgagg    4020
aagcaccagg gaacagcact tatatattct gcttacacac gatgcctgaa aaaacttccc    4080
ttggggttat ccacttatcc acgggatat ttttataatt attttttttta tagtttttag     4140 atccccgggt acc                                                       4153
```

```
<210> SEQ ID NO 7
<211> LENGTH: 31
<212> TYPE: DNA
<213> ORGANISM: Artificial Sequence
<220> FEATURE:
<223> OTHER INFORMATION: TK primer Fw

<400> SEQUENCE: 7
ccgcggactt tgtgattagt ttgatgcgat t                                     31

<210> SEQ ID NO 8
<211> LENGTH: 48
<212> TYPE: DNA
<213> ORGANISM: Artificial Sequence
<220> FEATURE:
<223> OTHER INFORMATION: TK primer Re

<400> SEQUENCE: 8
acaggtattt attcgccgcg gaaggttgta acattttatt accgtgtg                   48

<210> SEQ ID NO 9
<211> LENGTH: 87
<212> TYPE: DNA
<213> ORGANISM: Artificial Sequence
```

```
<220> FEATURE:
<223> OTHER INFORMATION: Kanamycin primer 1 Fw

<400> SEQUENCE: 9
tcacaaagtc cgcggcgata agctcatgga gcggcgtaac cgtcgcacag gaaggacaga      60
gaaagtaagt agggataaca gggtaat                                         87

<210> SEQ ID NO 10
<211> LENGTH: 40
<212> TYPE: DNA
<213> ORGANISM: Artificial Sequence
<220> FEATURE:
<223> OTHER INFORMATION: Kanamycin primer 1 Re

<400> SEQUENCE: 10
tccatgagct tatcgtgcca gtgttacaac caattaacca                           40

<210> SEQ ID NO 11
<211> LENGTH: 3175
<212> TYPE: DNA
<213> ORGANISM: Artificial Sequence
<220> FEATURE:
<223> OTHER INFORMATION: B5R modification cassette

<400> SEQUENCE: 11
tctagatttt tgatgctgtt gaatctttag attatctatt atccagagga gttattgata      60
ttaactatcg tactatatac aacgaaacat ctatttacga cgctgtcagt tataatgcgt     120
ataatacgtt ggtctatcta ttaaacaaaa atggtgattt tgagacgatt actactagtg     180
gatgtacatg tatttcggaa gcagtcgcaa acaacaacaa aataataatg gaagtactat     240
tgtctaaacg accatctttg aaaattatga tacagtctat gatagcaatt actaaacata     300
aacagcataa tgcagattta ttgaaaatgt gtataaaata tactgcgtgt atgaccgatt     360
atgatactct tatagatgta cagtcgctac agcaatataa atggtatatt ttaagatgtt     420
tcgatgaaat agatatcatg aagagatgtt atataaaaaa taaaactgta ttccaattag     480
ttttttgtat caaagacatt aatactttaa tgagatacgg taaacatcct tctttcgtga     540
agtgcactag tctcgacgta tacggaagtc gtgtacgtaa tatcatagca tctattagat     600
atcgtcagag attaattagt ctattatcca agaagctgga tgcgggagat aaatggtcgt     660
gttttcctaa cgaaataaaa tataaaatat tggaaaactt aacgataac gaactatcca     720 catatctaaa aatcttataa acattattaa aatataaaat ctaagtggat aaaatcacac     780
tacatcattg tttcctttta gtgctcgaca gtgtatacta tttttaacgc tcataaataa     840
aaatgaaaac gatttccgtt gttacgttgt tatgcgtact acctgctgtt gtttattcaa     900
catgtactgt acccactatg aataacgcta aattaacgtc taccgaaaca tcgtttaatg     960
ataaacagaa agttacattt acatgtgatc agggatatca ttctttggat ccaaatgctg    1020
tctgtgaaac agataaatgg aaatacgaaa atccatgcaa gaaaatgtgc acagtttctg    1080
attatgtctc tgaattatat gataagccat atacgaagt gaattccacc atgacactaa    1140
gttgcaacgg cgaaacaaaa tattttcgtt taagtaggga taacagggta atcgatttat    1200
tcaacaaagc cacgttgtgt ctcaaaatct ctgatgttac attgcacaag ataaaaatat    1260
atcatcatga acaataaaac tgtctgctta cataaacagt aatacaaggg gtgttatgag    1320
ccatattcaa cggaaacgt cttgctcgag gccgcgatta aattccaaca tggatgctga    1380
tttatatggg tataaatggg ctcgcgataa tgtcgggcaa tcaggtgcga caatctatcg    1440
```

-continued

```
attgtatggg aagcccgatg cgccagagtt gtttctgaaa catggcaaag gtagcgttgc    1500
caatgatgtt acagatgaga tggtcagact aaactggctg acggaattta tgcctcttcc    1560
gaccatcaag cattttatcc gtactcctga tgatgcatgg ttactcacca ctgcgatccc    1620
cgggaaaaca gcattccagg tattagaaga atatcctgat tcaggtgaaa atattgttga    1680
tgcgctggca gtgttcctgc gccggttgca ttcgattcct gtttgtaatt gtccttttaa    1740
cagcgatcgc gtatttcgtc tcgctcaggc gcaatcacga atgaataacg gtttggttga    1800
tgcgagtgat tttgatgacg agcgtaatgg ctggcctgtt gaacaagtct ggaaagaaat    1860
gcataagctt ttgccattct caccggattc agtcgtcact catggtgatt tctcacttga    1920
taaccttatt tttgacgagg ggaaattaat aggttgtatt gatgttggac gagtcggaat    1980
cgcagaccga taccaggatc ttgccatcct atggaactgc ctcggtgagt tttctccttc    2040
attacagaaa cggctttttc aaaaatatgg tattgataat cctgatatga ataaattgca    2100
gtttcatttg atgctcgatg agttttctta atcagaattg gttaattggt tgtaacactg    2160
gcagaattcc accatgacac taagttgcaa cggcgaaaca aaatatttc gttgcgaaga    2220 aaaaaatgga aatacttctt ggaatgatac tgttacgtgt cctaatgcgg aatgtcaacc    2280
tcttcaatta gaacacggat cgtgtcaacc agttaaagaa aaatactcat ttggggaata    2340
tatgactatc aactgtgatg ttggatatga ggttattggt gcttcgtaca taagttgtac    2400
agctaattct tggaatgtta ttccatcatg tcaacaaaaa tgtgatatgc cgtctctatc    2460
taacggatta atttccggat ctacattttc tatcggtggc gttatacatc ttagttgtaa    2520
aagtggtttt acactaacgg ggtctccatc atccacatgt atcgacggta aatggaatcc    2580
catactccca acatgtgtac gatctaacga aaaatttgat ccagtggatg atggtcccga    2640
cgatgagaca gatttgagca aactctcgaa agacgttgta caatatgaac aagaaataga    2700
atcgttagaa gcaacttatc atataatcat agtggcgtta acaattatgg gcgtcatatt    2760
tttaatctcc gttatagtat tagtttgttc ctgtgacaaa aataatgacc aatataagtt    2820
ccataaattg ctaccgtaaa tataaatccg ttaaataat taataattaa taacgaacaa    2880
gtatcaaaag attaaagact tatagctaga atcaattgag atgtcttctt cagtggatgt    2940
tgatatctac gatgccgtta gagcattttt actcaggcac tattataaca agagatttat    3000
tgtgtatgga agaagtaacg ccatattaca taatatatac aggctatttt caagatgcgc    3060
cgttataccg ttcgatgata tagtacgtac tatgccaaat gaatcacgtg ttaaacaatg    3120
ggtgatggat acacttaatg gtataatgat gaatgaacgc gatgtttctt ctaga    3175
```

```
<210> SEQ ID NO 12
<211> LENGTH: 5047
<212> TYPE: DNA
<213> ORGANISM: Artificial Sequence
<220> FEATURE:
<223> OTHER INFORMATION: pUCFk-B5RmO

<400> SEQUENCE: 12
tctagatttt tgatgctgtt gaatctttag attatctatt atccagagga gttattgata     60
ttaactatcg tactatatac aacgaaacat ctatttacga cgctgtcagt tataatgcgt    120
ataatacgtt ggtctatcta ttaaacaaaa atggtgattt tgagacgatt actactagtg    180
gatgtacatg tatttcggaa gcagtcgcaa acaacaacaa aataataatg gaagtactat    240
tgtctaaacg accatctttg aaaattatga tacagtctat gatagcaatt actaaacata    300
aacagcataa tgcagattta ttgaaaatgt gtataaaata tactgcgtgt atgaccgatt    360
```

-continued

```
atgatactct tatagatgta cagtcgctac agcaatataa atggtatatt ttaagatgtt    420
tcgatgaaat agatatcatg aagagatgtt atataaaaaa taaaactgta ttccaattag    480
ttttttgtat caaagacatt aatactttaa tgagatacgg taaacatcct tctttcgtga    540
agtgcactag tctcgacgta tacggaagtc gtgtacgtaa tatcatagca tctattagat    600
atcgtcagag attaattagt ctattatcca agaagctgga tgcgggagat aaatggtcgt    660
gttttcctaa cgaaataaaa tataaaatat tggaaaactt taacgataac gaactatcca    720
catatctaaa aatcttataa acattattaa aatataaaat ctaagtggat aaaatcacac    780
tacatcattg tttcctttta gtgctcgaca gtgtatacta tttttaacgc tcataaataa    840
aaatgaaaac gatttccgtt gttacgttgt tatgcgtact acctgctgtt gtttattcaa    900
catgtactgt acccactatg aataacgcta aattaacgtc taccgaaaca tcgtttaatg    960
ataaacagaa agttacattt acatgtgatc agggatatca ttctttggat ccaaatgctg    1020
tctgtgaaac agataaatgg aaatacgaaa atccatgcaa gaaaatgtgc acagtttctg    1080
attatgtctc tgaattatat gataagccat tatacgaagt gaattccacc atgacactaa    1140
gttgcaacgg cgaaacaaaa tattttcgtt gcgaagaaaa aaatggaaat acttcttgga    1200
atgatactgt tacgtgtcct aatgcggaat gtcaacctct tcaattagaa cacggatcgt    1260
gtcaaccagt taaagaaaaa tactcatttg gggaatatat gactatcaac tgtgatgttg    1320
gatatgaggt tattggtgct tcgtacataa gttgtacagc taattcttgg aatgttattc    1380
catcatgtca acaaaaatgt gatatgccgt ctctatctaa cggattaatt tccggatcta    1440
cattttctat cggtggcgtt atacatctta gttgtaaaag tggtttttaca ctaacggggt    1500 ctccatcatc cacatgtatc gacggtaaat ggaatcccat actcccaaca tgtgtacgat    1560
ctaacgaaaa atttgatcca gtggatgatg gtcccgacga tgagacagat ttgagcaaac    1620
tctcgaaaga cgttgtacaa tatgaacaag aaatagaatc gttagaagca acttatcata    1680
taatcatagt ggcgttaaca attatgggcg tcatattttt aatctccgtt atagtattag    1740
tttgttcctg tgacaaaaat aatgaccaat ataagttcca taaattgcta ccgtaaatat    1800
aaatccgtta aaataattaa taattaataa cgaacaagta tcaaaagatt aaagacttat    1860
agctagaatc aattgagatg tcttcttcag tggatgttga tatctacgat gccgttagag    1920 cattttact caggcactat tataacaaga gatttattgt gtatggaaga agtaacgcca    1980
tattacataa tatatacagg ctatttacaa gatgcgccgt tataccgttc gatgatatag    2040
tacgtactat gccaaatgaa tcacgtgtta aacaatgggt gatggataca cttaatggta    2100
taatgatgaa tgaacgcgat gtttcttcta gaatcagatc ggaagagcgt cgttaaggga    2160
aagagtgttc cgtactcaga gagctattac aattcactgg ccgtcgtttt acaacgtcgt    2220
gactgggaaa acccaggcgt tacccaactt aatcgccttg cagcacatcc tccgtttgcg    2280
agttggcgga atagcgaaga agcgcgtaca gatcgtccgt cacagcagtt gcgctctctg    2340
taacgtaccg cagttcaaag tctacaccta caaacgcgaa agtcgctatc gcctgtttgt    2400
ggatgtgcaa agcgacatca tcgatactcc tggtcgtcgc acggtgattc cgttggcttc    2460
tgcacggtta ctgagcgaca aagtttcccg tgaactctat ccggttgtcc acattgggga    2520
tgaaagctgg cgtatgatga ccacggatat ggcgtcagta ccagtgtcgg taattggcga    2580
agaggttgcg gatctgtcgc atcgcgagaa tgacatcaag aacgccatta acctgatgtt    2640
ttggggcatt taattaagcc agccccgaca cccgccaaca cccgctgacg cgccctgacg    2700
```

-continued

```
ggcttgtctg ctcccggcat ccgcttacag acaagctgtg accgtctccg ggagctgcat      2760
gtgtcagagg tttttcaccgt catcaccgaa acgcgcgaga cgaaagggcc tcgtgatacg      2820
cctattttta taggttaatg tcatgataat aatggtttct tagacgtcag gtggcacttt      2880
tcggggaaat gtgcgcggaa cccctatttg tttattttc taaatacatt caaatatgta      2940
tccgctcatg agacaataac cctgataaat gcttcaataa tattgaaaaa ggaagagtat      3000
gagccatatt caacgggaaa cgtcgaggcc gcgattaaat tccaacatgg atgctgattt      3060
atatgggtat aaatgggctc gcgataatgt cgggcaatca ggtgcgacaa tctatcgctt      3120
gtatgggaag cccgatgcgc cagagttgtt tctgaaacat ggcaaaggta gcgttgccaa      3180
tgatgttaca gatgagatgg tcagactaaa ctggctgacg gaatttatgc ctcttccgac      3240
catcaagcat tttatccgta ctcctgatga tgcatggtta ctcaccactg cgatccccgg      3300
aaaaacagca ttccaggtat tagaagaata tcctgattca ggtgaaaata ttgttgatgc      3360
gctggcagtg ttcctgcgcc ggttgcattc gattcctgtt tgtaattgtc cttttaacag      3420
cgatcgcgta tttcgtctcg ctcaggcgca atcacgaatg aataacggtt tggttgatgc      3480
gagtgatttt gatgacgagc gtaatggctg gcctgttgaa caagtctgga agaaatgca      3540 taaacttttg ccattctcac cggattcagt cgtcactcat ggtgatttct cacttgataa      3600
ccttattttt gacgagggga aattaatagg ttgtattgat gttggacgag tcggaatcgc      3660
agaccgatac caggatcttg ccatcctatg gaactgcctc ggtgagtttt ctccttcatt      3720
acagaaacgg ctttttcaaa aatatggtat tgataatcct gatatgaata aattgcagtt      3780
tcatttgatg ctcgatgagt ttttctaact gtcagaccaa gtttactcat atatacttta      3840
gattgattta aaacttcatt tttaatttaa aaggatctag gtgaagatcc tttttgataa      3900
tctcatgacc aaaatccctt aacgtgagtt ttcgttccac tgagcgtcag accccgtaga      3960
aaagatcaaa ggatcttctt gagatccttt ttttctgcgc gtaatctgct gcttgcaaac      4020
aaaaaaacca ccgctaccag cggtggtttg tttgccggat caagagctac caactctttt      4080
tccgaaggta actggcttca gcagagcgca gataccaaat actgttcttc tagtgtagcc      4140
gtagttaggc caccacttca agaactctgt agcaccgcct acatacctcg ctctgctaat      4200
cctgttacca gtggctgctg ccagtggcga taagtcgtgt cttaccgggt tggactcaag      4260
acgatagtta ccggataagg cgcagcggtc gggctgaacg gggggttcgt gcacacagcc      4320
cagcttggag cgaacgacct acaccgaact gagataccta cagcgtgagc tatgagaaag      4380
cgccacgctt cccgaaggga aaaggcgga caggtatccg gtaagcggca gggtcggaac      4440
aggagagcgc acgagggagc ttccaggggg aaacgcctgg tatctttata gtcctgtcgg      4500
gtttcgccac ctctgacttg agcgtcgatt tttgtgatgc tcgtcagggg ggcggagcct      4560
atggaaaaac gccagcaacg cggcctttt acggttcctg gccttttgct ggcctttgc      4620 tcacatgttc tttcctgcgt tatcccctga ttctgtggat aaccgtatta ccgcctttga      4680
gtgagctgat accgctcgcc gcagccgaac gaccgagcgc agcgagtcag tgagcgagga      4740
agcggaagag cgcccaatac gcaaaccgcc tctccccgcg cgttggccga ttcattaatg      4800
cagctggcac gacaggtttc ccgactggaa agcgggcagt gagcgcaacg caattaatgt      4860
gagttagctc actcattagg caccccaggc tttacacttt atgcttccgg ctcgtatgtt      4920
gtgtggaatt gtgagcggat aacaatttca cacaggaaac agctatgacc atgaccatga      4980
ttacgccaag ctatctgggc gataccattg aagactggag ttcagacgtg tgctcttccg      5040
atctgat                                                                 5047
```

-continued

```
<210> SEQ ID NO 13
<211> LENGTH: 73
<212> TYPE: DNA
<213> ORGANISM: Artificial Sequence
<220> FEATURE:
<223> OTHER INFORMATION: Kanamycin primer 2 Fw

<400> SEQUENCE: 13
ccggaattcc accatgacac taagttgcaa cggcgaaaca aaatatttttc gtttaagtag     60 ggataacagg gta                                                          73

<210> SEQ ID NO 14
<211> LENGTH: 39
<212> TYPE: DNA
<213> ORGANISM: Artificial Sequence
<220> FEATURE:
<223> OTHER INFORMATION: Kanamycin primer 2 Re

<400> SEQUENCE: 14
ccggaattct gccagtgtta caaccaatta accaattct                               39

<210> SEQ ID NO 15
<211> LENGTH: 3061
<212> TYPE: DNA
<213> ORGANISM: Artificial Sequence
<220> FEATURE:
<223> OTHER INFORMATION: C11R deletion cassette

<400> SEQUENCE: 15
ggatcccata ttgcaagtta ttctcggtac ccaccatcat atcaacgctg gtaactatat       60
tcttagaaat ataaaacttg tctgtatatg taagatgttt agaaaatgga tatttccaca      120
ttgctttaaa atggacggcg ctaacaactg tcatacgagt attaatggat agcggactag      180
tcaataagga attaatttta ccatttgtca ttgtcttaac ccattcgttg attagttcct      240
ttgtttggtt agcattatta aagtttacag tttgaaaatc gtcttttatt ttttgtagga      300
aggaggcatg gaactcgata ctatcgctac cgtatatttt atttgcggta gctagtgtcg      360
cacaatacgg aatatctacg tccatgtcat tattgtcatc gggtgtattc tcattcatat      420
tctctatata ttttgatagt tgttcagctg tagaaccagc tgctccatga tttagaatag      480
ataaagtaga taaaatagaa actggagaaa tcaaaacatt ttcatccgtg tgttttaaga      540
ttagttcttt aaagatatcc atggtataga ccaaacaata acgataacga tatatatcat      600
aaataaataa tgttaaattt tagtttatgt ttgtaccccg tattcatact taacaaattg      660
gtattgcgta cacaatcaat catattacat accattaata atgcaagcat aaaaaatcgt      720
tagtagatgt ttctaaatat aggttccgta agcaaagaat ataagaatga agcggtaatg      780
ataaaatcaa ttgttatcta aaatgatcat actcatttat tttattctat tatattaaca      840
catacatttt taacagcaac acattcaata ttgtattgtt atttttatat tatttacaca      900
attaacaata tattattagt ttatattact gaattaataa tataaaattc ccaatcttgt      960
cataaacaca cactgagaaa cagcataaac acaaaatcca tcaaaagtag actatcaacg     1020
ttcagaaaac ccaaacacta caacgtcata tatccctaag tagggataac agggtaatcg     1080
atttattcaa caaagccacg ttgtgtctca aaatctctga tgttacattg cacaagataa     1140
aaatatatca tcatgaacaa taaaactgtc tgcttacata aacagtaata caaggggtgt     1200
tatgagccat attcaacggg aaacgtcttg ctcgaggccg cgattaaatt ccaacatgga     1260
```

```
tgctgattta tatgggtata aatgggctcg cgataatgtc gggcaatcag gtgcgacaat      1320
ctatcgattg tatgggaagc ccgatgcgcc agagttgttt ctgaaacatg gcaaaggtag      1380
cgttgccaat gatgttacag atgagatggt cagactaaac tggctgacgg aatttatgcc      1440
tcttccgacc atcaagcatt ttatccgtac tcctgatgat gcatggttac tcaccactgc      1500
gatccccggg aaaacagcat tccaggtatt agaagaatat cctgattcag gtgaaaatat      1560
tgttgatgcg ctggcagtgt tcctgcgccg gttgcattcg attcctgttt gtaattgtcc      1620
ttttaacagc gatcgcgtat ttcgtctcgc tcaggcgcaa tcacgaatga ataacggttt      1680
ggttgatgcg agtgattttg atgacgagcg taatggctgg cctgttgaac aagtctggaa      1740
agaaatgcat aagcttttgc cattctcacc ggattcagtc gtcactcatg gtgatttctc      1800
acttgataac cttatttttg acgaggggaa attaataggt tgtattgatg ttggacgagt      1860
cggaatcgca gaccgatacc aggatcttgc catcctatgg aactgcctcg gtgagttttc      1920
tccttcatta cagaaacggc tttttcaaaa atatggtatt gataatcctg atatgaataa      1980
attgcagttt catttgatgc tcgatgagtt ttttctaatca gaattggtta attggttgta      2040
acactggcag tagactatca acgttcgaaa aacccaaaca ctacaacgtc atatatccca      2100
tctcccggta ttatgcttgt attagtaggc attattatta ttacgtgttg tctattatct      2160
gtttataggt tcactcgacg aactaaacta cttatacaag atatggttgt gccataattt      2220
ttataaattt tttttatgag tatttttaca aaaatgtata aagtgtatgt cttatgtata      2280
tttataaaaa tgctaaatat gcgatgtatc tatgttattt gtatttatct aaacaatacc      2340
tctacctcta gatattatac aaaaatttt tatttcagca tattaaagta aaatctagtt      2400
accttgaaaa tgaatacagt gggtggttcc gtatcaccag taagaacata atagtcgaat      2460
acagtatccg attgagattt tgcatacaat actagtctag aaagaaattt gtaatcattt      2520
tctgtgacgg gagtccatat atctgtatca tcgtctagtt tatcagtgtc ccatgctata      2580
ttcctgttat catcattagt taatgaaaat aactctcgtg cttcagaaaa gtcaaatatt      2640
gtatccatac atacatctcc aaaactatcg cttatacgtt tatctttaac gatacctata      2700
cctagatggt tatttactaa cagacatttt ccagatctat tgactataac tcctatagtt      2760
tccacatcaa ccaagtaatg atcatctatt gttatataac aataacataa ctcttttcca      2820
tttttatcag tatgtatatc tatatcaacg tcgtcgttgt agtgaatagt agtcattgat      2880
ctattatatg aaacggatat gtctagaacg gcaattgttt tacgtccagt taacactttc      2940
tttgatttaa agtctagagt ctttgcaaac ataatatcct tatccgactt tatatttcct      3000
gtagggtggt ataattttat tttgcctcca catatcggtg tttccaaata tattagaatt      3060
c                                                                      3061
```

<210> SEQ ID NO 16
<211> LENGTH: 4689
<212> TYPE: DNA
<213> ORGANISM: Artificial Sequence
<220> FEATURE:
<223> OTHER INFORMATION: pUC57-deltaVGF plasmid

<400> SEQUENCE: 16

```
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg       120 ttggcgggtg tcgggctgg cttaactatg cggcatcaga gcagattgta ctgagagtgc       180
accatatgcg gtgtgaaata ccgcacagat gcgtaaggag aaaataccgc atcaggcgcc       240
```

```
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt gacgcgtatt gggatggatc      420
ccatattgca agttattctc ggtacccacc atcatatcaa cgctggtaac tatattctta      480
gaaatataaa acttgtctgt atatgtaaga tgtttagaaa atggatattt ccacattgct      540
ttaaaatgga cggcgctaac aactgtcata cgagtattaa tggatagcgg actagtcaat      600
aaggaattaa ttttaccatt tgtcattgtc ttaacccatt cgttgattag ttcctttgtt      660
tggttagcat tattaaagtt tacagtttga aaatcgtctt ttattttttg taggaaggag      720
gcatggaact cgatactatc gctaccgtat attttatttg cggtagctag tgtcgcacaa      780 tacgaatat ctacgtccat gtcattattg tcatcgggtg tattctcatt catattctct      840
atatattttg atagttgttc agctgtagaa ccagctgctc catgatttag aatagataaa      900
gtagataaaa tagaaactgg agaaatcaaa acattttcat ccgtgtgttt taagattagt      960
tctttaaaga tatccatggt atagaccaaa caataacgat aacgatatat atcataaata     1020
aataatgtta aattttagtt tatgtttgta ccccgtattc atacttaaca aattggtatt     1080
gcgtacacaa tcaatcatat tacataccat taataatgca agcataaaaa atcgttagta     1140
gatgtttcta aatataggtt ccgtaagcaa agaatataag aatgaagcgg taatgataaa     1200
atcaattgtt atctaaaatg atcatactca tttattttat tctattatat taacacatac     1260 attttaaca gcaacacatt caatattgta ttgttatttt tatattattt acacaattaa     1320
caatatatta ttagtttata ttactgaatt aataatataa aattcccaat cttgtcataa     1380
acacacactg agaaacagca taaacacaaa atccatcaaa agtagactat caacgttcag     1440
aaaacccaaa cactacaacg tcatatatcc catctcccgg tattatgctt gtattagtag     1500
gcattattat tattacgtgt tgtctattat ctgtttatag gttcactcga cgaactaaac     1560
tacttataca agatatggtt gtgccataat ttttataaat tttttttatg agtattttta     1620
caaaaatgta taaagtgtat gtcttatgta tatttataaa aatgctaaat atgcgatgta     1680
tctatgttat ttgtatttat ctaaacaata cctctacctc tagatattat acaaaaattt     1740
tttatttcag catattaaag taaaatctag ttaccttgaa aatgaataca gtgggtggtt     1800
ccgtatcacc agtaagaaca taatagtcga atacagtatc cgattgagat tttgcataca     1860
atactagtct agaaagaaat ttgtaatcat tttctgtgac gggagtccat atatctgtat     1920
catcgtctag tttatcagtg tcccatgcta tattcctgtt atcatcatta gttaatgaaa     1980
ataactctcg tgcttcagaa aagtcaaata ttgtatccat acatacatct ccaaaactat     2040
cgcttatacg tttatcttta acgataccta tacctagatg gttatttact aacagacatt     2100
ttccagatct attgactata actcctatag tttccacatc aaccaagtaa tgatcatcta     2160
ttgttatata acaataacat aactcttttc cattttttatc agtatgtata tctatatcaa     2220
cgtcgtcgtt gtagtgaata gtagtcattg atctattata tgaaacggat atgtctagaa     2280
cggcaattgt tttacgtcca gttaacactt tctttgattt aaagtctaga gtctttgcaa     2340
acataatatc cttatccgac tttatatttc ctgtagggtg gtataatttt attttgcctc     2400
cacatatcgg tgtttccaaa tatattagaa ttcatcccaa tggcgcgccg agcttggcgt     2460
aatcatggtc atagctgttt cctgtgtgaa attgttatcc gctcacaatt ccacacaaca     2520
tacgagccgg aagcataaag tgtaaagcct ggggtgccta atgagtgagc taactcacat     2580
```

-continued

```
taattgcgtt gcgctcactg cccgctttcc agtcgggaaa cctgtcgtgc cagctgcatt   2640
aatgaatcgg ccaacgcgcg gggagaggcg gtttgcgtat tgggcgctct tccgcttcct   2700
cgctcactga ctcgctgcgc tcggtcgttc ggctgcggcg agcggtatca gctcactcaa   2760
aggcggtaat acggttatcc acagaatcag gggataacgc aggaaagaac atgtgagcaa   2820
aaggccagca aaaggccagg aaccgtaaaa aggccgcgtt gctggcgttt ttccataggc   2880
tccgcccccc tgacgagcat cacaaaaatc gacgctcaag tcagaggtgg cgaaacccga   2940
caggactata aagataccag gcgtttcccc ctggaagctc cctcgtgcgc tctcctgttc   3000
cgaccctgcc gcttaccgga tacctgtccg cctttctccc ttcgggaagc gtggcgcttt   3060
ctcatagctc acgctgtagg tatctcagtt cggtgtaggt cgttcgctcc aagctgggct   3120
gtgtgcacga accccccgtt cagcccgacc gctgcgcctt atccggtaac tatcgtcttg   3180
agtccaaccc ggtaagacac gacttatcgc cactggcagc agccactggt aacaggatta   3240
gcagagcgag gtatgtaggc ggtgctacag agttcttgaa gtggtggcct aactacggct   3300
acactagaag aacagtattt ggtatctgcg ctctgctgaa gccagttacc ttcggaaaaa   3360
gagttggtag ctcttgatcc ggcaaacaaa ccaccgctgg tagcggtggt ttttttgttt   3420
gcaagcagca gattacgcgc agaaaaaaag gatctcaaga agatcctttg atctttccta   3480
cggggtctga cgctcagtgg aacgaaaact cacgttaagg gattttggtc atgagattat   3540
caaaaaggat cttcacctag atccttttaa attaaaaatg aagttttaaa tcaatctaaa   3600
gtatatatga gtaaacttgg tctgacagtt accaatgctt aatcagtgag gcacctatct   3660
cagcgatctg tctatttcgt tcatccatag ttgcctgact ccccgtcgtg tagataacta   3720
cgatacggga gggcttacca tctggcccca gtgctgcaat gataccgcga gacccacgct   3780
caccggctcc agatttatca gcaataaacc agccagccgg aagggccgag cgcagaagtg   3840
gtcctgcaac tttatccgcc tccatccagt ctattaattg ttgccgggaa gctagagtaa   3900
gtagttcgcc agttaatagt ttgcgcaacg ttgttgccat tgctacaggc atcgtggtgt   3960
cacgctcgtc gtttggtatg gcttcattca gctccggttc ccaacgatca aggcgagtta   4020
catgatcccc catgttgtgc aaaaaagcgg ttagctcctt cggtcctccg atcgttgtca   4080
gaagtaagtt ggccgcagtg ttatcactca tggttatggc agcactgcat aattctctta   4140
ctgtcatgcc atccgtaaga tgcttttctg tgactggtga gtactcaacc aagtcattct   4200
gagaatagtg tatgcggcga ccgagttgct cttgcccggc gtcaatacgg gataataccg   4260
cgccacatag cagaacttta aaagtgctca tcattggaaa acgttcttcg gggcgaaaac   4320
tctcaaggat cttaccgctg ttgagatcca gttcgatgta acccactcgt gcacccaact   4380
gatcttcagc atcttttact ttcaccagcg tttctgggtg agcaaaaaca ggaaggcaaa   4440
atgccgcaaa aaagggaata agggcgacac ggaaatgttg aatactcata ctcttccttt   4500
ttcaatatta ttgaagcatt tatcagggtt attgtctcat gagcggatac atatttgaat   4560
gtatttagaa aaataaacaa ataggggttc cgcgcacatt tccccgaaaa gtgccacctg   4620
acgtctaaga aaccattatt atcatgacat taacctataa aaataggcgt atcacgaggc   4680
cctttcgtc                                                             4689
```

<210> SEQ ID NO 17
<211> LENGTH: 85
<212> TYPE: DNA
<213> ORGANISM: Artificial Sequence
<220> FEATURE:
<223> OTHER INFORMATION: Kanamycin primer 3 Fw -continued

```
<400> SEQUENCE: 17
caaaatccat caaaagtaga ctatcaacgt tcagaaaacc caaacactac aacgtcatat      60
atccctaagt agggataaca gggta                                           85

<210> SEQ ID NO 18
<211> LENGTH: 51
<212> TYPE: DNA
<213> ORGANISM: Artificial Sequence
<220> FEATURE:
<223> OTHER INFORMATION: Kanamycin primer 3 Re

<400> SEQUENCE: 18
ttctgaacgt tgatagtcta ctgccagtgt tacaaccaat taaccaattc t             51

<210> SEQ ID NO 19
<211> LENGTH: 2724
<212> TYPE: DNA
<213> ORGANISM: Artificial Sequence
<220> FEATURE:
<223> OTHER INFORMATION: O1L deletion cassette

<400> SEQUENCE: 19
gaattctcgg tattttttat ggcaaacttt actcttccag catccgtttc taaaaaaata     60
ttaacgagtt ccattatat catccaatat tattgaaatg acgttgatgg acagatgata     120
caaataagaa ggtacggtac ctttgtccac catctcctcc aattcatgct ctattttgtc    180
attaacttta atgtatgaaa acagtacgcc acatgcttcc atgacagtgt gtaacacttt    240
ggatacaaaa tgtttgacat tagtataatt gtccaagact gtcaatctat aatagatagt    300
agctataata tattctatga tggtattgaa gaagatgaca accttggcat attgatcatt    360
taacacagac atggtatcaa cagatagctt gaatgaaaga gaatcagtaa ttggaataag    420
cgtcttctcg atagagtgtc cgtataccaa catgtctgat attttgatgt attccattaa    480
attatttagt tttttctttt tattctcgtt aaacagcatt tctgtcaacg gaccccaaca    540
tcgttgaccg attaagtttt gattgatttt tccgtgtaag gcgtatctag tcagatcgta    600
tagcctatcc aataatccat cgtctgtgtg tagatcacat cgtacacttt ttaattctct    660
atagaagagc gacagacatc tggagcaatt acagacagca atttctttat tctctacaga    720
tgtaagatac ttgaagacat tcctatgatg atgcagaatt ttggataaca cggtattgat    780
ggtatctgtt accataattc ctttgatggc tgatagtgtc agagcacaag atttccaatc    840
tttgacaatt tttagcacca ttatctttgt tttgatatct atatcagaca gcatggtgcg    900
tctgacaaca cagggattaa gacggaaaga tgaaatgatt ctctcaacat cttcaatgga    960
taccttgcta ttttttctgg cattatctat atgtgcgaga atatcctcta gagtcggcga   1020
catgattaag tattgttttt tcattatttt tatatttaag tagggataac agggtaatcg   1080
atttattcaa caaagccacg ttgtgtctca aaatctctga tgttacattg cacaagataa   1140
aaatatatca tcatgaacaa taaaactgtc tgcttacata aacagtaata caaggggtgt   1200
tatgagccat attcaacggg aaacgtcttg ctcgaggccg cgattaaatt ccaacatgga   1260
tgctgattta tatgggtata atgggctcg cgataatgtc gggcaatcag gtgcgacaat   1320
ctatcgattg tatgggaagc ccgatgcgcc agagttgttt ctgaaacatg gcaaaggtag   1380
cgttgccaat gatgttacag atgagatggt cagactaaac tggctgacgg aatttatgcc   1440
tcttccgacc atcaagcatt ttatccgtac tcctgatgat gcatggttac tcaccactgc   1500
```

-continued

```
gatccccggg aaaacagcat tccaggtatt agaagaatat cctgattcag gtgaaaatat      1560
tgttgatgcg ctggcagtgt tcctgcgccg gttgcattcg attcctgttt gtaattgtcc      1620 tttttaacagc gatcgcgtat ttcgtctcgc tcaggcgcaa tcacgaatga ataacggttt      1680
ggttgatgcg agtgattttg atgacgagcg taatggctgg cctgttgaac aagtctggaa      1740
agaaatgcat aagcttttgc cattctcacc ggattcagtc gtcactcatg gtgatttctc      1800
acttgataac cttatttttg acgaggggaa attaataggt tgtattgatg ttggacgagt      1860
cggaatcgca gaccgatacc aggatcttgc catcctatgg aactgcctcg gtgagttttc      1920
tccttcatta cagaaacggc tttttcaaaa atatggtatt gataatcctg atatgaataa      1980
attgcagttt catttgatgc tcgatgagtt tttctaatca gaattggtta attggttgta      2040
acactggcat ctagagtcgg cgacatgatt aagtattgtt ttttcattat ttttatattt      2100
tctcaacaag ttctcaatac cccaatagat gatagaatat cacccaatgc gtccatgttg      2160
tctatttcca acaggtcgct atatccacca atagaagttt ttccaaaaaa gattctagga      2220
acagttctac caccagtaat ttgttcaaaa taatcacgca attcattttc gggtttaaat      2280
tctttaatat cgacaatttc atacgctcct cttttgaaac taaacttatt tagaatatcc      2340
agtgcatttc tacaaaaagg acatgtatac ttgacaaaaa ttgtcacttt gttattggcc      2400
aacctttgtt gtacaaattc ctcggccatt ttaatattta agtgatataa aactatctcg      2460
acttatttaa ctctttagtc gagatatatg gacgcagata gctatatgat agccaactac      2520
agaaggcaaa cgctataaaa aacataatta caacgagcat atttataaat atttttattc      2580
agcattactt gatatagtaa tattaggcac agtcaaacat caaccactc tcgatacatt       2640 aactctctca ttttctttaa caaattctgc aatatcttcg taaaaagatt cttgaaactt      2700
tttagaatat ctatcgacga attc                                              2724
```

```
<210> SEQ ID NO 20
<211> LENGTH: 5403
<212> TYPE: DNA
<213> ORGANISM: Artificial Sequence
<220> FEATURE:
<223> OTHER INFORMATION: pUC57-deltaO1L-rKanI

<400> SEQUENCE: 20
```

```
gaattctcgg tattttttat ggcaaacttt actcttccag catccgtttc taaaaaaata       60
ttaacgagtt ccatttatat catccaatat tattgaaatg acgttgatgg acagatgata      120
caaataagaa ggtacggtac ctttgtccac catctcctcc aattcatgct ctattttgtc      180
attaacttta atgtatgaaa acagtacgcc acatgcttcc atgacagtgt gtaacacttt      240
ggatacaaaa tgtttgacat tagtataatt gtccaagact gtcaatctat aatagatagt      300
agctataata tattctatga tggtattgaa gaagatgaca accttggcat attgatcatt      360
taacacagac atggtatcaa cagatagctt gaatgaaaga gaatcagtaa ttggaataag      420
cgtcttctcg atagagtgtc cgtataccaa catgtctgat attttgatgt attccattaa      480
attatttagt tttttctttt tattctcgtt aaacagcatt tctgtcaacg accccaaca       540 tcgttgaccg attaagtttt gattgatttt tccgtgtaag gcgtatctag tcagatcgta      600
tagcctatcc aataatccat cgtctgtgtg tagatcacat cgtacacttt ttaattctct      660
atagaagagc gacagacatc tggagcaatt acagacagca atttctttat tctctacaga      720
tgtaagatac ttgaagacat tcctatgatg atgcagaatt ttggataaca cggtattgat      780
ggtatctgtt accataattc ctttgatggc tgatagtgtc agagcacaag atttccaatc      840
```

```
tttgacaatt tttagcacca ttatctttgt tttgatatct atatcagaca gcatggtgcg      900
tctgacaaca cagggattaa gacggaaaga tgaaatgatt ctctcaacat cttcaatgga      960
taccttgcta tttttttctgg cattatctat atgtgcgaga atatcctcta gagtcggcga     1020
catgattaag tattgttttt tcattatttt tatatttaag tagggataac agggtaatcg     1080
atttattcaa caaagccacg ttgtgtctca aaatctctga tgttacattg cacaagataa     1140
aaatatatca tcatgaacaa taaaactgtc tgcttacata aacagtaata caaggggtgt     1200
tatgagccat attcaacggg aaacgtcttg ctcgaggccg cgattaaatt ccaacatgga     1260
tgctgattta tatgggtata aatgggctcg cgataatgtc gggcaatcag gtgcgacaat     1320
ctatcgattg tatgggaagc ccgatgcgcc agagttgttt ctgaaacatg gcaaaggtag     1380
cgttgccaat gatgttacag atgagatggt cagactaaac tggctgacgg aatttatgcc     1440
tcttccgacc atcaagcatt ttatccgtac tcctgatgat gcatggttac tcaccactgc     1500
gatccccggg aaaacagcat tccaggtatt agaagaatat cctgattcag gtgaaaatat     1560
tgttgatgcg ctggcagtgt tcctgcgccg gttgcattcg attcctgttt gtaattgtcc     1620
ttttaacagc gatcgcgtat ttcgtctcgc tcaggcgcaa tcacgaatga ataacggttt     1680
ggttgatgcg agtgattttg atgacgagcg taatggctgg cctgttgaac aagtctggaa     1740
agaaatgcat aagcttttgc cattctcacc ggattcagtc gtcactcatg gtgatttctc     1800
acttgataac cttattttttg acgaggggaa attaataggt tgtattgatg ttggacgagt     1860
cggaatcgca gaccgatacc aggatcttgc catcctatgg aactgcctcg gtgagttttc     1920
tccttcatta cagaaacggc tttttcaaaa atatggtatt gataatcctg atatgaataa     1980
attgcagttt catttgatgc tcgatgagtt ttttctaatca gaattggtta attggttgta     2040
acactggcat ctagagtcgg cgacatgatt aagtattgtt ttttcattat ttttatattt     2100
tctcaacaag ttctcaatac cccaatagat gatagaatat cacccaatgc gtccatgttg     2160
tctatttcca acaggtcgct atatccacca atagaagttt ttccaaaaaa gattctagga     2220
acagttctac caccagtaat ttgttcaaaa taatcacgca attcattttc gggtttaaat     2280
tctttaatat cgacaatttc atacgctcct cttttgaaac taaacttatt tagaatatcc     2340
agtgcatttc tacaaaaagg acatgtatac ttgacaaaaa ttgtcacttt gttattggcc     2400
aacctttgtt gtacaaattc ctcggccatt ttaatattta agtgatataa aactatctcg     2460
acttatttaa ctctttagtc gagatatatg gacgcagata gctatatgat agccaactac     2520
agaaggcaaa cgctataaaa aacataatta caacgagcca atttataaat atttttattc     2580
agcattactt gatatagtaa tattaggcac agtcaaacat tcaaccactc tcgatacatt     2640
aactctctca ttttctttaa caaattctgc aatatcttcg taaaaagatt cttgaaactt     2700
tttagaatat ctatcgacga attcatccca atggcgcgcc gagcttggcg taatcatggt     2760
catagctgtt tcctgtgtga aattgttatc cgctcacaat tccacacaac atacgagccg     2820
gaagcataaa gtgtaaagcc tggggtgcct aatgagtgag ctaactcaca ttaattgcgt     2880
tgcgctcact gcccgctttc cagtcgggaa acctgtcgtg ccagctgcat taatgaatcg     2940
gccaacgcgc ggggagaggc ggtttgcgta ttgggcgctc ttccgcttcc tcgctcactg     3000
actcgctgcg ctcggtcgtt cggctgcggc gagcggtatc agctcactca aaggcggtaa     3060
tacggttatc cacagaatca ggggataacg caggaaagaa catgtgagca aaaggccagc     3120
aaaaggccag gaaccgtaaa aaggccgcgt tgctggcgtt tttccatagg ctccgccccc     3180
```

-continued

```
ctgacgagca tcacaaaatc acaaaaatcg acgctcaagt cagaggtggc gaaacccgac      3240
aggactataa agataccagg cgtttccccc tggaagctcc ctcgtgcgct ctcctgttcc      3300
gaccctgccg cttaccggat acctgtccgc ctttctccct tcgggaagcg tggcgctttc      3360
tcatagctca cgctgtaggt atctcagttc ggtgtaggtc gttcgctcca agctgggctg      3420
tgtgcacgaa ccccccgttc agcccgaccg ctgcgcctta tccggtaact atcgtcttga      3480
gtccaacccg gtaagacacg acttatcgcc actggcagca gccactggta acaggattag      3540
cagagcgagg tatgtaggcg gtgctacaga gttcttgaag tggtggccta actacggcta      3600
cactagaaga acagtatttg gtatctgcgc tctgctgaag ccagttacct tcggaaaaag      3660
agttggtagc tcttgatccg gcaaacaaac caccgctggt agcggtggtt tttttgtttg      3720
caagcagcag attacgcgca gaaaaaaagg atctcaagaa gatcctttga tcttttctac      3780
ggggtctgac gctcagtgga acgaaaactc acgttaaggg attttggtca tgagattatc      3840
aaaaaggatc ttcacctaga tcctttttaaa ttaaaaatga agttttaaat caatctaaag      3900
tatatatgag taaacttggt ctgacagtta ccaatgctta atcagtgagg cacctatctc      3960
agcgatctgt ctatttcgtt catccatagt tgcctgactc cccgtcgtgt agataactac      4020
gatacgggag ggcttaccat ctggccccag tgctgcaatg ataccgcgag acccacgctc      4080
accggctcca gatttatcag caataaacca gccagccgga agggccgagc gcagaagtgg      4140
tcctgcaact ttatccgcct ccatccagtc tattaattgt tgccgggaag ctagagtaag      4200
tagttcgcca gttaatagtt tgcgcaacgt tgttgccatt gctacaggca tcgtggtgtc      4260
acgctcgtcg tttggtatgg cttcattcag ctccggttcc caacgatcaa ggcgagttac      4320
atgatccccc atgttgtgca aaaaagcggt tagctccttc ggtcctccga tcgttgtcag      4380
aagtaagttg gccgcagtgt tatcactcat ggttatggca gcactgcata attctcttac      4440
tgtcatgcca tccgtaagat gcttttctgt gactggtgag tactcaacca agtcattctg      4500
agaatagtgt atgcggcgac cgagttgctc ttgcccggcg tcaatacggg ataataccgc      4560
gccacatagc agaactttaa aagtgctcat cattggaaaa cgttcttcgg ggcgaaaact      4620
ctcaaggatc ttaccgctgt tgagatccag ttcgatgtaa cccactcgtg cacccaactg      4680
atcttcagca tcttttactt tcaccagcgt ttctgggtga gcaaaaacag gaaggcaaaa      4740
tgccgcaaaa aagggaataa gggcgacacg gaaatgttga atactcatac tcttcctttt      4800
tcaatattat tgaagcattt atcagggtta ttgtctcatg agcggataca tatttgaatg      4860
tatttagaaa aataaacaaa tagggggttcc gcgcacattt ccccgaaaag tgccacctga      4920
cgtctaagaa accattatta tcatgacatt aacctataaa aataggcgta tcacgaggcc      4980
ctttcgtctc gcgcgtttcg gtgatgacgg tgaaaacctc tgacacatgc agctcccgga      5040
gacggtcaca gcttgtctgt aagcggatgc cgggagcaga caagcccgtc agggcgcgtc      5100
agcgggtgtt ggcgggtgtc ggggctggct taactatgcg gcatcagagc agattgtact      5160
gagagtgcac catatgcggt gtgaaatacc gcacagatgc gtaaggagaa aataccgcat      5220
caggcgccat cgccattca ggctgcgcaa ctgttgggaa gggcgatcgg tgcgggcctc      5280
ttcgctatta cgccagctgg cgaaggggg atgtgctgca aggcgattaa gttgggtaac      5340
gccagggttt tcccagtcac gacgttgtaa aacgacggcc agtgaattga cgcgtattgg      5400
gat                                                                   5403
```

<210> SEQ ID NO 21
<211> LENGTH: 3162

<212> TYPE: DNA
<213> ORGANISM: Artificial Sequence
<220> FEATURE:
<223> OTHER INFORMATION: F4L deletion cassette

<400> SEQUENCE: 21

```
ggatcctatt tcattgttca tccatccacc gatgagatat actacttctc caacatgagt      60
acttgtacac atatggaata tatctataat ttgatccatg ttcataggat actctatgaa     120
tggatacttg tatgatttgc gtggttgttt atcacaatga aatattttgg tacagtctag     180
tatccatttt acattattta tacctctggg agaaagataa tttgacctga ttacattttt     240
gataaggagt agcagatttc ctaatttatt tcttcgcctc atataccact taatgacaaa     300
atcaactaca taatcctcat ctggaacatt tagttcatcg ctttctagaa taagtttcat     360
agatagataa tcaaaattgt ctatgatgtc atcttccagt tccaaaaagt gtttggcaat     420
aaagttttta gtatgacata agagattgga tagtccgtat tctataccca tcatgtaaca     480
ctcgacacaa tattcctttc taaaatctcg taagataaag tttatacaag tgtagatgat     540
aaattctaca gaggttaata tagaagcacg taataaattg acgacgttat gactatctat     600
atataccttt ccagtatatg agtaaataac tatagaagtt aaactgtgaa tgtcaaggtc     660
tagacaaacc ctcgtaactg gatctttatt tttcgtgtat ttttgacgta aatgtgtgcg     720
aaagtaagga gataacttttt tcaatatcgt agaattgact attatattgc ctcctatggc     780
atcaataatt gttttgaatt tcttagtcat agacaatgct aatatattct tacagtacac     840
agtattgaca aatatcggca tttatgtttc tttaaaagtc aacatctaga gaaaaatgat     900
tatctttttg agacataact cccatttttt ggtattcacc cacacgtttt tcgaaaaaat     960 tagttttttcc ttccaatgat atattttcca tgaaatcaaa cggattggta acattataaa    1020 ttttttttaaa tcccaattca gaaatcaatc tatccgcgac gaattcaact aaattaacaa    1080
taacaataaa tttttttttca gttatctata taagtaggga taacagggta atcgatttat    1140
tcaacaaagc cacgttgtgt ctcaaaatct ctgatgttac attgcacaag ataaaaatat    1200
atcatcatga acaataaaac tgtctgctta cataaacagt aatacaaggg gtgttatgag    1260
ccatattcaa cgggaaacgt cttgctcgag gccgcgatta aattccaaca tggatgctga    1320
tttatatggg tataaatggg ctcgcgataa tgtcgggcaa tcaggtgcga caatctatcg    1380
attgtatggg aagcccgatg cgccagagtt gtttctgaaa catggcaaag gtagcgttgc    1440
caatgatgtt acagatgaga tggtcagact aaactggctg acggaattta tgcctcttcc    1500
gaccatcaag cattttatcc gtactcctga tgatgcatgg ttactcacca ctgcgatccc    1560
cgggaaaaca gcattccagg tattagaaga atatcctgat tcaggtgaaa atattgttga    1620
tgcgctggca gtgttcctgc gccggttgca ttcgattcct gtttgtaatt gtccttttaa    1680
cagcgatcgc gtatttcgtc tcgctcaggc gcaatcacga atgaataacg gtttggttga    1740
tgcgagtgat tttgatgacg agcgtaatgg ctggcctgtt gaacaagtct ggaaagaaat    1800
gcataagctt ttgccattct caccggattc agtcgtcact catggtgatt tctcacttga    1860
taaccttatt tttgacgagg ggaaattaat aggttgtatt gatgttggac gagtcggaat    1920
cgcagaccga taccaggatc ttgccatcct atggaactgc ctcggtgagt tttctccttc    1980
attacagaaa cggctttttc aaaaatatgg tattgataat cctgatatga ataaattgca    2040
gtttcatttg atgctcgatg agtttttcta atcagaattg gttaattggt tgtaacactg    2100
gcagaattca actaaattaa caataacaat aaatttttttt tcagttatct atatgcctgt    2160
```

```
acttggatct tttgtacatc gatatcgccg caatcactac aataattaca agtattattg    2220
atagcattgt tattagtact atcataatta aattatctac attcatgggt gctgaataat    2280
cgttattatc atcattatca ttttgtaatt gtgacatcat actagataaa tcgtttgcga    2340
gattgttgtg ggaagcgggc atggaggatg cattatcatt attatttaac gccttccatt    2400
tggattcaca aatgttacgc acattcaaca ttttatggaa actataattt tgtgaaaaca    2460
gataacaaga aaactcgtca tcgttcaaat ttttaacgat agtaaaccga ttaaacgtcg    2520
agctaatttc taacgctagc gactctgttg gatatgggtt tccagatata tatcttttca    2580
gttcccctac gtatctataa tcatctgtag gaaatggaag atatttccat ttatctactg    2640
ttcctaatat catatgtggt ggtgtagtag aaccattaag cgcgaaagat gttatttcgc    2700
atcgtatttt aacttcgcaa taatttctgg ttagataacg cactctacca gtcaagtcaa    2760
tgatattagc ctttacagat atattcatag tagtcgtaac gatgactcca tcttttagat    2820
gcgatactcc tttgtatgta ccagaatctt cgtacctcaa actcgatata tttaaacaag    2880
ttaatgagat attaacgcgt tttatgaatg atgatatata accagaagtt ttatcctcgg    2940
tggctagcgc tataacctta tcattataat accaactagt gtgattaata tgtgacacgt    3000
cagtgtgggt acaaatatgt acattatcgt ctacgtcgta ttcgtacat ccgcatacag    3060 ccaacaaata taaaatgaca aatactctaa cgacgttcgt acccatcttg atgcggttta    3120
ataaatgttt tgatttcaat ttattgtaaa aaaagaggat cc                       3162
```

<210> SEQ ID NO 22
<211> LENGTH: 5841
<212> TYPE: DNA
<213> ORGANISM: Artificial Sequence
<220> FEATURE:
<223> OTHER INFORMATION: pUC57-deltaF4L-rKanI

<400> SEQUENCE: 22

```
ggatcctatt tcattgttca tccatccacc gatgagatat actacttctc caacatgagt      60
acttgtacac atatggaata tatctataat ttgatccatg ttcataggat actctatgaa     120
tggatacttg tatgatttgc gtggttgttt atcacaatga aatattttgg tacagtctag     180
tatccatttt acattattta tacctctggg agaaagataa tttgacctga ttacattttt     240
gataaggagt agcagatttc ctaatttatt tcttcgcctc atataccact aatgacaaa     300 atcaactaca taatcctcat ctggaacatt tagttcatcg ctttctagaa taagtttcat     360
agatagataa tcaaaattgt ctatgatgtc atcttccagt tccaaaaagt gtttggcaat     420 aaagtttta gtatgacata agagattgga tagtccgtat tctatccca tcatgtaaca      480 ctcgacacaa tattcctttc taaaatctcg taagataaag tttatacaag tgtagatgat     540
aaattctaca gaggttaata tagaagcacg taataaattg acgacgttat gactatctat     600
atataccttt ccagtatatg agtaaataac tatagaagtt aaactgtgaa tgtcaaggtc     660
tagacaaacc ctcgtaactg gatctttatt tttcgtgtat ttttgacgta aatgtgtgcg     720
aaagtaagga gataactttt tcaatatcgt agaattgact attatattgc ctcctatggc     780
atcaataatt gttttgaatt tcttagtcat agacaatgct aatatattct tacagtacac     840
agtattgaca aatatcggca tttatgtttc tttaaaagtc aacatctaga gaaaaatgat     900 tatcttttttg agacataact cccatttttt ggtattcacc cacacgtttt tcgaaaaaat     960 tagttttttcc ttccatgat atattttcca tgaaatcaaa cggattggta acattataaa    1020 ttttttttaaa tcccaattca gaaatcaatc tatccgcgac gaattcaact aaattaacaa    1080
```

-continued

```
taacaataaa ttttttttca gttatctata taagtaggga taacagggta atcgatttat  1140
tcaacaaagc cacgttgtgt ctcaaaatct ctgatgttac attgcacaag ataaaaatat  1200
atcatcatga acaataaaac tgtctgctta cataaacagt aatacaaggg gtgttatgag  1260
ccatattcaa cgggaaacgt cttgctcgag gccgcgatta aattccaaca tggatgctga  1320
tttatatggg tataaatggg ctcgcgataa tgtcgggcaa tcaggtgcga caatctatcg  1380
attgtatggg aagcccgatg cgccagagtt gtttctgaaa catggcaaag gtagcgttgc  1440
caatgatgtt acagatgaga tggtcagact aaactggctg acggaattta tgcctcttcc  1500
gaccatcaag cattttatcc gtactcctga tgatgcatgg ttactcacca ctgcgatccc  1560
cgggaaaaca gcattccagg tattagaaga atatcctgat tcaggtgaaa atattgttga  1620
tgcgctggca gtgttcctgc gccggttgca ttcgattcct gtttgtaatt gtccttttaa  1680
cagcgatcgc gtatttcgtc tcgctcaggc gcaatcacga atgaataacg gtttggttga  1740
tgcgagtgat tttgatgacg agcgtaatgg ctggcctgtt gaacaagtct ggaaagaaat  1800
gcataagctt ttgccattct caccggattc agtcgtcact catggtgatt tctcacttga  1860
taaccttatt tttgacgagg ggaaattaat aggttgtatt gatgttggac gagtcggaat  1920
cgcagaccga taccaggatc ttgccatcct atggaactgc ctcggtgagt tttctccttc  1980
attacagaaa cggctttttc aaaaatatgg tattgataat cctgatatga ataaattgca  2040
gtttcatttg atgctcgatg agtttttcta atcagaattg gttaattggt tgtaacactg  2100
gcagaattca actaaattaa caataacaat aaattttttt tcagttatct atatgcctgt  2160
acttggatct tttgtacatc gatatcgccg caatcactac aataattaca agtattattg  2220
atagcattgt tattagtact atcataatta aattatctac attcatgggt gctgaataat  2280
cgttattatc atcattatca ttttgtaatt gtgacatcat actagataaa tcgtttgcga  2340
gattgttgtg ggaagcgggc atggaggatg cattatcatt attatttaac gccttccatt  2400
tggattcaca aatgttacgc acattcaaca ttttatggaa actataattt tgtgaaaaca  2460
gataacaaga aaactcgtca tcgttcaaat ttttaacgat agtaaaccga ttaaacgtcg  2520
agctaatttc taacgctagc gactctgttg gatatgggtt tccagatata tatcttttca  2580
gttcccctac gtatctataa tcatctgtag gaaatggaag atatttccat ttatctactg  2640
ttcctaatat catatgtggt ggtgtagtag aaccattaag cgcgaaagat gttatttcgc  2700
atcgtatttt aacttcgcaa taatttctgg ttagataacg cactctacca gtcaagtcaa  2760
tgatattagc ctttacagat atattcatag tagtcgtaac gatgactcca tcttttagat  2820
gcgatactcc tttgtatgta ccagaatctt cgtacctcaa actcgatata tttaaacaag  2880
ttaatgagat attaacgcgt tttatgaatg atgatatata accagaagtt ttatcctcgg  2940
tggctagcgc tataacctta tcattataat accaactagt gtgattaata tgtgacacgt  3000
cagtgtgggt acaaatatgt acattatcgt ctacgtcgta ttcgtacat ccgcatacag  3060 ccaacaaata taaaatgaca aatactctaa cgacgttcgt acccatcttg atgcggttta  3120
ataaatgttt tgatttcaat ttattgtaaa aaaagaggat ccatcccaat ggcgcgccga  3180
gcttggcgta atcatggtca tagctgtttc ctgtgtgaaa ttgttatccg ctcacaattc  3240
cacacaacat acgagccgga agcataaagt gtaaagcctg gggtgcctaa tgagtgagct  3300
aactcacatt aattgcgttg cgctcactgc ccgctttcca gtcgggaaac ctgtcgtgcc  3360
agctgcatta atgaatcggc caacgcgcgg ggagaggcgg tttgcgtatt gggcgctctt  3420
```

-continued

```
ccgcttcctc gctcactgac tcgctgcgct cggtcgttcg gctgcggcga gcggtatcag   3480
ctcactcaaa ggcggtaata cggttatcca cagaatcagg ggataacgca ggaaagaaca   3540
tgtgagcaaa aggccagcaa aaggccagga accgtaaaaa ggccgcgttg ctggcgtttt   3600
tccataggct ccgcccccct gacgagcatc acaaaatcac aaaaatcgac gctcaagtca   3660
gaggtggcga aacccgacag gactataaag ataccaggcg tttccccctg gaagctccct   3720
cgtgcgctct cctgttccga ccctgccgct taccggatac ctgtccgcct ttctcccttc   3780
gggaagcgtg gcgctttctc atagctcacg ctgtaggtat ctcagttcgg tgtaggtcgt   3840
tcgctccaag ctgggctgtg tgcacgaacc ccccgttcag cccgaccgct gcgccttatc   3900
cggtaactat cgtcttgagt ccaacccggt aagacacgac ttatcgccac tggcagcagc   3960
cactggtaac aggattagca gagcgaggta tgtaggcggt gctacagagt tcttgaagtg   4020
gtggcctaac tacggctaca ctagaagaac agtatttggt atctgcgctc tgctgaagcc   4080
agttaccttc ggaaaaagag ttggtagctc ttgatccggc aaacaaacca ccgctggtag   4140
cggtggtttt tttgtttgca agcagcagat tacgcgcaga aaaaaaggat ctcaagaaga   4200
tcctttgatc ttttctacgg ggtctgacgc tcagtggaac gaaaactcac gttaagggat   4260
tttggtcatg agattatcaa aaaggatctt cacctagatc cttttaaatt aaaaatgaag   4320
ttttaaatca atctaaagta tatatgagta aacttggtct gacagttacc aatgcttaat   4380
cagtgaggca cctatctcag cgatctgtct atttcgttca tccatagttg cctgactccc   4440
cgtcgtgtag ataactacga tacgggaggg cttaccatct ggccccagtg ctgcaatgat   4500
accgcgagac ccacgctcac cggctccaga tttatcagca ataaaccagc cagccggaag   4560
ggccgagcgc agaagtggtc ctgcaacttt atccgcctcc atccagtcta ttaattgttg   4620
ccgggaagct agagtaagta gttcgccagt taatagtttg cgcaacgttg ttgccattgc   4680
tacaggcatc gtggtgtcac gctcgtcgtt tggtatggct tcattcagct ccggttccca   4740
acgatcaagg cgagttacat gatcccccat gttgtgcaaa aaagcggtta gctccttcgg   4800
tcctccgatc gttgtcagaa gtaagttggc cgcagtgtta tcactcatgg ttatggcagc   4860
actgcataat tctcttactg tcatgccatc cgtaagatgc ttttctgtga ctggtgagta   4920
ctcaaccaag tcattctgag aatagtgtat gcggcgaccg agttgctctt gcccggcgtc   4980
aatacgggat aataccgcgc cacatagcag aactttaaaa gtgctcatca ttggaaaacg   5040
ttcttcgggg cgaaaactct caaggatctt accgctgttg agatccagtt cgatgtaacc   5100
cactcgtgca cccaactgat cttcagcatc ttttactttc accagcgttt ctgggtgagc   5160
aaaaacagga aggcaaaatg ccgcaaaaaa gggaataagg gcgacacgga aatgttgaat   5220
actcatactc ttcctttttc aatattattg aagcatttat cagggttatt gtctcatgag   5280
cggatacata tttgaatgta tttagaaaaa taaacaaata ggggttccgc gcacatttcc   5340
ccgaaaagtg ccacctgacg tctaagaaac cattattatc atgacattaa cctataaaaa   5400
taggcgtatc acgaggccct ttcgtctcgc gcgtttcggt gatgacggtg aaaacctctg   5460
acacatgcag ctcccggaga cggtcacagc ttgtctgtaa gcggatgccg ggagcagaca   5520
agcccgtcag ggcgcgtcag cgggtgttgg cgggtgtcgg ggctggctta actatgcggc   5580
atcagagcag attgtactga gagtgcacca tatgcggtgt gaaataccgc acagatgcgt   5640
aaggagaaaa taccgcatca ggcgccattc gccattcagg ctgcgcaact gttgggaagg   5700
gcgatcggtg cgggcctctt cgctattacg ccagctggcg aaagggggat gtgctgcaag   5760
gcgattaagt tgggtaacgc cagggttttc ccagtcacga cgttgtaaaa cgacggccag   5820
```

-continued

```
tgaattgacg cgtattggga t                                            5841

<210> SEQ ID NO 23
<211> LENGTH: 3149
<212> TYPE: DNA
<213> ORGANISM: Artificial Sequence
<220> FEATURE:
<223> OTHER INFORMATION: A33R modification cassette

<400> SEQUENCE: 23
ggatccaatg ttaaaactac aaaaatgcgt aatgttagcc cgtcctaata ttggtacgtg     60
tctataagtt tggcatagta gaataataga cgtgtttaaa tgccttccga agtttaagaa    120
ttctattaga gtattgcatt ttgatagttt atcacctaca tcatcaaaaa taagtaaaaa    180
gtgtgctgat tttttatgat tttgtgcgac agcaatacat ttttctatgt tacttttagt    240
tcgtatcaga ttatattcta gagattcctg actactaacg aaattaatat gatttggcca    300
aatgtatcca tcataatctg ggttataaac gggtgtaaac aagaatatat gtttatattt    360
tttaactagt gtagaaaaca gagatagtaa atagatagtt tttccagatc cagatcctcc    420
cgttaaaacc attctaaacg gcatttttaa taaattttct cttgaaaatt gtttttcttg    480
gaaacaattc ataattatat ttacagttac taaattaatt tgataataaa tcaaaatatg    540
gaaaactaag gttgttagta gggaggagaa caaagaaggc acatcgtgat ataaataaca    600
tttattatca tgatgacacc agaaaacgac gaagagcaga catctgtgtt ctccgctact    660
gtttacggag acaaaattca gggaaagaat aaacgcaaac gcgtgattgg tctatgtatt    720
agaatatcta tggttatttc actactatct atgattacca tgtccgcgtt tctcatagtg    780
cgcctaaatc aatgcatgtc tgctaacgag gctgctatta ctgacgccgc tgttgccgtt    840
gctgctgcat catctactca tagaaaggtt gcgtctagca ctacgcaata tgatcacaaa    900
gaaagctgta atggtttata ttaccagggt tcttgttata tattacattc agactaccag    960
ttattctcgg atgctaaagc aaattgcact gcggaatcat caacactaag tagggataac   1020
agggtaatcg atttattcaa caaagccacg ttgtgtctca aaatctctga tgttacattg   1080
cacaagataa aaatatatca tcatgaacaa taaaactgtc tgcttacata aacagtaata   1140 caagggtgt tatgagccat attcaacggg aaacgtcttg ctcgaggccg cgattaaatt   1200
ccaacatgga tgctgattta tatgggtata aatgggctcg cgataatgtc gggcaatcag   1260
gtgcgacaat ctatcgattg tatgggaagc ccgatgcgcc agagttgttt ctgaaacatg   1320
gcaaaggtag cgttgccaat gatgttacag atgagatggt cagactaaac tggctgacgg   1380
aatttatgcc tcttccgacc atcaagcatt ttatccgtac tcctgatgat gcatggttac   1440
tcaccactgc gatccccggg aaaacagcat tccaggtatt agaagaatat cctgattcag   1500
gtgaaaatat tgttgatgcg ctggcagtgt tcctgcgccg gttgcattcg attcctgttt   1560
gtaattgtcc tttaacagc gatcgcgtat ttcgtctcgc tcaggcgcaa tcacgaatga   1620
ataacggttt ggttgatgcg agtgattttg atgacgagcg taatggctgg cctgttgaac   1680
aagtctggaa agaaatgcat aagcttttgc cattctcacc ggattcagtc gtcactcatg   1740
gtgatttctc acttgataac cttattttg acgaggggaa attaataggt tgtattgatg   1800
ttggacgagt cggaatcgca gaccgatacc aggatcttgc catcctatgg aactgcctcg   1860
gtgagttttc tccttcatta cagaaacggc tttttcaaaa atatggtatt gataatcctg   1920
atatgaataa attgcagttt catttgatgc tcgatgagtt tttctaatca gaattggtta   1980
```

```
attggttgta acactggcaa ttctcggatg ctaaagcaaa ttgcactgcg gaatcatcaa       2040
cactacccaa taaatccgat gtcttgatta cctggctcat tgattatgtt gaggatacat       2100
ggggatctga tggtaatcca attacaaaaa ctacatccga ttatcaagat tctgatatat       2160
cacaagaagt tagaaagtat ttttgtgtta aaacaatgaa ctaatattta tttttgtaca       2220
ttaataaatg aaatcgctta atagacaaac tgtaagtagg tttaagaagt tgtcggtgcc       2280
ggccgctata atgatgatac tctcaaccat tattagtggc ataggaacat ttctgcatta       2340
caaagaagaa ctgatgccta gtgcttgcgc caatggatgg atacaatacg ataaacattg       2400
ttatttagat actaacatta aaatgtctac agataatgcg gtttatcagt gtcgtaaatt       2460
acgagctaga ttgcctagac ctgatactag acatctgaga gtattgttta gtatttttta       2520
taaagattat tgggtaagtt taaaaaagac caataataaa tggttagata ttaataatga       2580
taaagatata gatattagta aattaacaaa ttttaaacaa ctaaacagta cgacggatgc       2640
tgaagcgtgt tatatataca agtctggaaa actggttaaa acagtatgta aaagtactca       2700
atctgtacta tgtgttaaaa aattctacaa gtgacaacaa aaaatgaatt aataataagt       2760
cgttaacgta cgccgccatg gacgccgcgt ttgttattac tccaatgggt gtgttgacta       2820
taacagatac attgtatgat gatctcgata tctcaatcat ggactttata ggaccataca       2880
ttataggtaa cataaaaact gtccaaatag atgtacggga tataaaatat tccgacatgc       2940
aaaaatgcta ctttagctat aagggtaaaa tagttcctca ggattctaat gatttggcta       3000
gattcaacat ttatagcatt tgtgccgcat acagatcaaa aaataccatc atcatagcat       3060
gcgactatga tatcatgtta gatatagaag ataaacatca gccattttat ctattcccat       3120
ctattgatgt ttttaacgct acaggatcc                                        3149
```

<210> SEQ ID NO 24
<211> LENGTH: 3198
<212> TYPE: DNA
<213> ORGANISM: Artificial Sequence
<220> FEATURE:
<223> OTHER INFORMATION: A34R modification cassette

<400> SEQUENCE: 24

```
ggatccagta gggaggagaa caaagaaggc acatcgtgat ataaataaca tttattatca        60
tgatgacacc agaaaacgac gaagagcaga catctgtgtt ctccgctact gtttacggag       120
acaaaattca gggaaagaat aaacgcaaac gcgtgattgg tctatgtatt agaatatcta       180
tggttatttc actactatct atgattacca gtgtccgcgtt tctcatagtg cgcctaaatc      240
aatgcatgtc tgctaacgag gctgctatta ctgacgccgc tgttgccgtt gctgctgcat       300
catctactca tagaaaggtt gcgtctagca ctacgcaata tgatcacaaa gaaagctgta       360
atggtttata ttaccagggt tcttgttata tattacattc agactaccag ttattctcgg       420
atgctaaagc aaattgcact gcggaatcat caacactacc caataaatcc gatgtcttga       480
ctacctggct cattgattat gttgaggata catgggggatc tgatggtaat ccaattacaa       540
aaactacatc caattatcaa gattctgatg tatcacaaga gttagaaag tattttttgtg        600 ttaaaacaat gaactaatat ttatttttgt acattaataa atgaaatcgc ttaatagaca       660
aactgtaagt aggtttaaga agttgtcggt gccggccgct ataatgatga tactctcaac       720
cattattagt ggcataggaa catttctgca ttacaaagaa gaactgatgc ctagtgcttg       780
cgccaatgga tggatacaat acgataaaca ttgttatttta gatactaaca ttaaaatgtc       840
tacagataat gcggtttatc agtgtcgtaa attacgagct agattgccta gacctgatac       900
```

-continued

```
tagacatctg agagtattgt ttagtatttt ttataaagat tattgggtaa gtttaaaaaa    960
gaccaataat aaatggttag atattaataa tgataaagat atagatatta gtaaattaac   1020
aaattttaaa caactaaaca gtacgacgga tgctgaagcg tgttatatat acaagtctgg   1080
aaaacttaag tagggataac agggtaatcg atttattcaa caaagccacg ttgtgtctca   1140
aaatctctga tgttacattg cacaagataa aaatatatca tcatgaacaa taaaactgtc   1200
tgcttacata aacagtaata caaggggtgt tatgagccat attcaacggg aaacgtcttg   1260
ctcgaggccg cgattaaatt ccaacatgga tgctgattta tatgggtata aatgggctcg   1320
cgataatgtc gggcaatcag gtgcgacaat ctatcgattg tatgggaagc ccgatgcgcc   1380
agagttgttt ctgaaacatg gcaaaggtag cgttgccaat gatgttacag atgagatggt   1440
cagactaaac tggctgacgg aatttatgcc tcttccgacc atcaagcatt ttatccgtac   1500
tcctgatgat gcatggttac tcaccactgc gatccccggg aaaacagcat tccaggtatt   1560 agaagaaat cctgattcag gtgaaaatat tgttgatgcg ctggcagtgt tcctgcgccg   1620
gttgcattcg attcctgttt gtaattgtcc ttttaacagc gatcgcgtat ttcgtctcgc   1680
tcaggcgcaa tcacgaatga ataacggttt ggttgatgcg agtgattttg atgacgagcg   1740
taatggctgg cctgttgaac aagtctggaa agaaatgcat aagcttttgc cattctcacc   1800
ggattcagtc gtcactcatg gtgatttctc acttgataac cttatttttg acgaggggaa   1860
attaataggt tgtattgatg ttggacgagt cggaatcgca gaccgatacc aggatcttgc   1920
catcctatgg aactgcctcg gtgagttttc tccttcatta cagaaacggc tttttcaaaa   1980
atatggtatt gataatcctg atatgaataa attgcagttt catttgatgc tcgatgagtt   2040
tttctaatca gaattggtta attggttgta acactggcaa cgacggatgc tgaagcgtgt   2100
tatatataca agtctggaaa actggttgaa cagtatgtaa aagtactcaa tctgtactat   2160
gtgttaaaaa attctacaag tgacaacaaa aaatgaatta ataataagtc gttaacgtac   2220
gccgccatgg acgccgcgtt tgttattact ccaatgggtg tgttgactat aacagataca   2280
ttgtatgatg atctcgatat ctcaatcatg gactttatag gaccatacat tataggtaac   2340
ataaaaactg tccaaataga tgtacgggat ataaaatatt ccgacatgca aaaatgctac   2400
tttagctata agggtaaaat agttcctcag gattctaatg atttggctag attcaacatt   2460
tatagcattt gtgccgcata cagatcaaaa aataccatca tcatagcatg cgactatgat   2520
atcatgttag atatagaaga taaacatcag ccattttatc tattcccatc tattgatgtt   2580
tttaacgcta caatcataga agcgtataac ctgtatacag ctggagatta tcatctaatc   2640
atcaatcctt cagataatct gaaaatgaaa ttgtcgttta attcttcatt ctgcatatca   2700
gacggcaatg gatggatcat aattgatggg aaatgcaata gtaatttttt atcataaaag   2760
ttgtaaagta aataataaaa caataaatat tgaactagta gtacgtatat tgagcaatca   2820
gaaatgatgc tggtacctct tatcacggtg accgtagttg cgggaacaat attagtatgt   2880
tatatattat atatttgtag gaaaaagata cgtactgtct ataatgacaa taaaattatc   2940
atgacaaaat taaaaaagat aaagagttct aattccagca aatctagtaa atcaactgat   3000
agcgaatcag actgggagga tcactgtagt gctatggaac aaaacaatga cgtagataat   3060
atttctagga atgagatatt ggacgatgat agcttcgctg gtagtttaat atgggataac   3120
gaatccaatg ttatagcgcc tagcacagaa cacatttacg atagtgttgc tggaagcacg   3180
ctgctaataa atggatcc                                                 3198
```

<210> SEQ ID NO 25
<211> LENGTH: 3089
<212> TYPE: DNA
<213> ORGANISM: Artificial Sequence
<220> FEATURE:
<223> OTHER INFORMATION: A36R modification cassette

<400> SEQUENCE: 25

```
ggatcctaac aaattttaaa caactaaaca gtacgacgga tgctgaagcg tgttatatat        60
acaagtctgg aaaactggtt aaaacagtat gtaaaagtac tcaatctgta ctatgtgtta       120
aaaaattcta caagtgacaa caaaaaatga attaataata agtcgttaac gtacgccgcc       180
atggacgccg cgtttgttat tactccaatg ggtgtgttga ctataacaga tacattgtat       240
gatgatctcg atatctcaat catggacttt ataggaccat acattatagg taacataaaa       300
actgtccaaa tagatgtacg ggatataaaa tattccgaca tgcaaaaatg ctactttagc       360
tataagggta aaatagttcc tcaggattct aatgatttgg ctagattcaa catttatagc       420
atttgtgccg catacagatc aaaaaatacc atcatcatag catgcgacta tgatatcatg       480
ttagatatag aagataaaca tcagccattt tatctattcc catctattga tgtttttaac       540
gctacaatca tagaagcgta taacctgtat acagctggag attatcatct aatcatcaat       600
ccttcagata atctgaaaat gaaattgtcg tttaattctt cattctgcat atcagacggc       660
aatggatgga tcataattga tgggaaatgc aatagtaatt ttttatcata aaagttgtaa       720
agtaaataat aaaacaataa atattgaact agtagtacgt atattgagca atcagaaatg       780
atgctggtac ctcttatcac ggtgaccgta gttgcgggaa caatattagt atgttatata       840
ttatatattt gtaggaaaaa gatacgtact gtctataatg acaataaaat tatcatgaca       900
aaattaaaaa agataaagag ttctaattcc agcaaatcta gtaaatcaac tgatagcgaa       960
tcagactggg aggatcactg tagtgctatg gaacaaaaca atgacgtaag tagggataac      1020
agggtaatcg atttattcaa caaagccacg ttgtgtctca aaatctctga tgttacattg      1080
cacaagataa aaatatatca tcatgaacaa taaaactgtc tgcttacata aacagtaata      1140
caaggggtgt tatgagccat attcaacggg aaacgtcttg ctcgaggccg cgattaaatt      1200
ccaacatgga tgctgattta tatgggtata aatgggctcg cgataatgtc gggcaatcag      1260
gtgcgacaat ctatcgattg tatgggaagc ccgatgcgcc agagttgttt ctgaaacatg      1320
gcaaaggtag cgttgccaat gatgttacag atgagatggt cagactaaac tggctgacgg      1380
aatttatgcc tcttccgacc atcaagcatt ttatccgtac tcctgatgat gcatggttac      1440
tcaccactgc gatccccggg aaaacagcat tccaggtatt agaagaatat cctgattcag      1500
gtgaaaatat tgttgatgcg ctggcagtgt tcctgcgccg gttgcattcg attcctgttt      1560
gtaattgtcc ttttaacagc gatcgcgtat ttcgtctcgc tcaggcgcaa tcacgaatga      1620
ataacggttt ggttgatgcg agtgattttg atgacgagcg taatggctgg cctgttgaac      1680
aagtctggaa agaaatgcat aagctttttgc cattctcacc ggattcagtc gtcactcatg      1740
gtgatttctc acttgataac cttatttttg acgaggggaa attaataggt tgtattgatg      1800
ttggacgagt cggaatcgca gaccgatacc aggatcttgc catcctatgg aactgcctcg      1860
gtgagttttc tccttcatta cagaaacggc tttttcaaaa atatggtatt gataatcctg      1920
atatgaataa attgcagttt catttgatgc tcgatgagtt tttctaatca gaattggtta      1980
attggttgta acactggcaa gactgggagg atcactgtag tgctatggaa caaaacaatg      2040
acgtagataa tatttctagg aatgagatat ggacgatga tagcttcgct ggtagtttaa      2100
```

-continued

```
tatgggataa cgaatccaat gttatggcgc ctagcacaga acacatttac gatagtgttg      2160
ctggaagcac gctgctaata aataatgatc gtaatgaaca gactatttat cagaacacta      2220
cagtagtaat taatgaaacg gagactgtta aagtacttaa tgaagatacc aaacagaatc      2280
ctaactattc atccaatcct ttcgtaaatt ataataaaac cagtatttgt agcaagtcaa      2340
atccgtttat tacagaactt aacaataaat ttagtgagaa taatccgttt agacgagcac      2400
atagcgatga ttatcttaat aagcaagaac aagatcatga acacgatgat atagaatcat      2460
cggtcgtatc attggtgtga ttagtttcct ttttataaaa ttgaagtaat atttagtatt      2520
attgctgccg tcacgttgta caaatggaga tattccctgt attcggcatt tctaaaatta      2580
gcaattttat tgctaataat gactgtagat attatataga tacagaacat caaaaaatta      2640
tatctgatga gatcaataga cagatggatg aaacggtact tcttaccaac atcttaagcg      2700
tagaagttgt aaatgacaat gagatgtacc atcttattcc tcatagatta tcgacgatta      2760
tactctgtat tagttctgtc ggaggatgtg ttatctctat agataatgac atcaatgaca      2820
aaaatattct aacatttccc attgatcatg ctgtaatcat atccccactg agtaaatgtg      2880
tcgtagttag caagggtcct acaaccatat tggttgttaa agcggatata cctagcaaac      2940
gattggtaac atcgtttaca aacgacatac tatatgtaaa caatctgtca ctgattaatt      3000
atttgccgtt gtctgtattc attattagac gagtcaccga ctatttggat agacgcatat      3060
gcgatcagat atttgctaat aatggatcc                                       3089
```

```
<210> SEQ ID NO 26
<211> LENGTH: 5682
<212> TYPE: DNA
<213> ORGANISM: Artificial Sequence
<220> FEATURE:
<223> OTHER INFORMATION: A33-34-36R modification cassette

<400> SEQUENCE: 26
ggatccgatt tggttgtatt ggggaaggta acaattaatg atctaaagat gatgctattt        60
tacatggatt tatcatatca tggagtgaca agtagtggag caatttacaa attgggatcg       120
tctatcgata gactttctct aaataggact attgttacaa aagttaataa taattataat       180
tatgatgata cattttttga cgacgatgat tgatcgctat tgcacaattt tgttttttta       240
ctttctaata tagcgtttag attctttttc atgtgcgaat attgatttac taaaatatct       300
atgtttaact tttgttctat aacgtcctta tcggcggtat cggtacatat acgtaattca       360
ccttcacaaa atacggagtc ttcgataata atagccaatc gattattgga tctagctgtc       420
tgtatcatat tcaacatgtt taatatatcc tttcgtttcc cctttacagg catcgatcgt       480
agcatatttt ccgcgtctga tatggaaatg ttaaaactac aaaaatgcgt aatgttagcc       540
cgtcctaata ttggtacgtg tctataagtt tggcatagta gaataataga cgtgtttaaa       600
tgccttccga gtttaagaa ttctattaga gtattgcatt ttgatagttt atcacctaca       660
tcatcaaaaa taagtaaaaa gtgtgctgat tttttatgat tttgtgcgac agcaatacat       720
ttttctatgt tacttttagt tcgtatcaga ttatattcta gagattcctg actactaacg       780
aaattaatat gatttggcca aatgtatcca tcataatctg ggttataaac gggtgtaaac       840
aagaatatat gtttatattt tttaactagt gtagaaaaca gagatagtaa atagatagtt       900
tttccagatc cagatcctcc cgttaaaacc attctaaacg gcatttttaa taaattttct       960
cttgaaaatt gttttttcttg gaaacaattc ataattatat ttacagttac taaattaatt      1020
```

-continued

```
tgataataaa tcaaaatatg gaaaactaag gttgttagta gggaggagaa caaagaaggc   1080
acatcgtgat ataaataaca tttattatca tgatgacacc agaaaacgac gaagagcaga   1140
catctgtgtt ctccgctact gtttacggag acaaaattca gggaaagaat aaacgcaaac   1200
gcgtgattgg tctatgtatt agaatatcta tggttatttc actactatct atgattacca   1260
tgtccgcgtt tctcatagtg cgcctaaatc aatgcatgtc tgctaacgag gctgctatta   1320
ctgacgccgc tgttgccgtt gctgctgcat catctactca tagaaaggtt gcgtctagca   1380
ctacgcaata tgatcacaaa gaaagctgta atggtttata ttaccagggt tcttgttata   1440
tattacattc agactaccag ttattctcgg atgctaaagc aaattgcact gcggaatcat   1500
caacactacc caataaatcc gatgtcttga ttacctggct cattgattat gttgaggata   1560
catggggatc tgatggtaat ccaattacaa aaactacatc cgattatcaa gattctgata   1620
tatcacaaga agttagaaag tatttttgtg ttaaaacaat gaactaatat ttattttgt    1680 acattaataa atgaaatcgc ttaatagaca aactgtaagt aggtttaaga agttgtcggt   1740
gccggccgct ataatgatga tactctcaac cattattagt ggcataggaa catttctgca   1800
ttacaaagaa gaactgatgc ctagtgcttg cgccaatgga tggatacaat acgataaaca   1860
ttgttatcta gataccaaca ttaaaatgtc tacagataat gcggtttatc agtgtcgtaa   1920
attacgagct agattgccta gacctgatac tagacatctg agagtattgt ttagtatttt   1980
ttataaagat tattgggtaa gtttaaaaaa gaccaataat aaatggttag atattaataa   2040
tgataaagat atagatatta gtaaattaac aaattttaaa caactaaaca gtacgacgga   2100
tgctgaagcg tgttatatat acaagtctgg aaaactggtt gaacagtatg taaaagtact   2160
caatctgtac tatgtgttaa aaaattctac aagtgacaac aaaaaatgaa ttaataataa   2220
gtcgttaacg tacgccgcca tggacgccgc gtttgttatt actccaatgg gtgtgttgac   2280
tataacagat acattgtatg atgatctcga tatctcaatc atggacttta taggaccata   2340
cattataggt aacataaaaa ctgtccaaat agatgtacgg gatataaaat attccgacat   2400
gcaaaaatgc tactttagct ataagggtaa aatagttcct caggattcta atgatttggc   2460
tagattcaac atttatagca tttgtgccgc atacagatca aaaaatacca tcatcatagc   2520
atgcgactat gatatcatgt tagatataga agataaacat cagccatttt atctattccc   2580
atctattgat gttttttaacg ctacaatcat agaagcgtat aacctgtata cagctggaga   2640
ttatcataag tagggataac agggtaatcg atttattcaa caaagccacg ttgtgtctca   2700
aaatctctga tgttacattg cacaagataa aaatatatca tcatgaacaa taaaactgtc   2760
tgcttacata aacagtaata caaggggtgt tatgagccat attcaacggg aaacgtcttg   2820
ctcgaggccg cgattaaatt ccaacatgga tgctgattta tatgggtata atgggctcg    2880 cgataatgtc gggcaatcag gtgcgacaat ctatcgattg tatgggaagc ccgatgcgcc   2940
agagttgttt ctgaaacatg gcaaaggtag cgttgccaat gatgttacag atgagatggt   3000
cagactaaac tggctgacgg aatttatgcc tcttccgacc atcaagcatt ttatccgtac   3060
tcctgatgat gcatggttac tcaccactgc gatccccggg aaaacagcat tccaggtatt   3120
agaagaatat cctgattcag gtgaaaatat tgttgatgcg ctggcagtgt cctgcgccg    3180 gttgcattcg attcctgttt gtaattgtcc ttttaacagc gatcgcgtat ttcgtctcgc   3240
tcaggcgcaa tcacgaatga ataacggttt ggttgatgcg agtgattttg atgacgagcg   3300
taatggctgg cctgttgaac aagtctggaa agaaatgcat aagcttttgc cattctcacc   3360
ggattcagtc gtcactcatg gtgatttctc acttgataac cttattttg acgagggga    3420
```

-continued

```
attaataggt tgtattgatg ttggacgagt cggaatcgca gaccgatacc aggatcttgc    3480
catcctatgg aactgcctcg gtgagttttc tccttcatta cagaaacggc tttttcaaaa    3540
atatggtatt gataatcctg atatgaataa attgcagttt catttgatgc tcgatgagtt    3600
tttctaatca gaattggtta attggttgta acactggcaa caatcataga agcgtataac    3660
ctgtatacag ctggagatta tcatctaatc atcaatcctt cagataatct gaaaatgaaa    3720
ttgtcgttta attcttcatt ctgcatatca gacggcaatg gatggatcat aattgatggg    3780
aaatgcaata gtaatttttt atcataaaag ttgtaaagta aataataaaa caataaatat    3840
tgaactagta gtacgtatat tgagcaatca gaaatgatgc tggtacctct tatcacggtg    3900
accgtagttg cgggaacaat attagtatgt tatatattat atatttgtag gaaaaagata    3960
cgtactgtct ataatgacaa taaaattatc atgacaaaat taaaaaagat aaagagttct    4020
aattccagca aatctagtaa atcaactgat agcgaatcag actgggagga tcactgtagt    4080
gctatggaac aaaacaatga cgtagataat atttctagga atgagatatt ggacgatgat    4140
agcttcgctg gtagtttaat atgggataac gaatccaatg ttatggcgcc tagcacagaa    4200
cacatttacg atagtgttgc tggaagcacg ctgctaataa ataatgatcg taatgaacag    4260
actatttatc agaacactac agtagtaatt aatgaaacgg agactgttaa agtacttaat    4320
gaagatacca aacagaatcc taactattca tccaatcctt tcgtaaatta taataaaacc    4380
agtatttgta gcaagtcaaa tccgtttatt acagaactta acaataaatt tagtgagaat    4440
aatccgttta gacgagcaca tagcgatgat tatcttaata agcaagaaca agatcatgaa    4500
cacgatgata tagaatcatc ggtcgtatca ttggtgtgat tagtttcctt tttataaaat    4560
tgaagtaata tttagtatta ttgctgccgt cacgttgtac aaatggagat attccctgta    4620
ttcggcattt ctaaaattag caattttatt gctaataatg actgtagata ttatatagat    4680
acagaacatc aaaaaattat atctgatgag atcaatagac agatggatga aacggtactt    4740
cttaccaaca tcttaagcgt agaagttgta aatgacaatg agatgtacca tcttattcct    4800
catagattat cgacgattat actctgtatt agttctgtcg gaggatgtgt tatctctata    4860
gataatgaca tcaatgacaa aaatattcta acatttccca ttgatcatgc tgtaatcata    4920
tccccactga gtaaatgtgt cgtagttagc aagggtccta caaccatatt ggttgttaaa    4980
gcggatatac ctagcaaacg attggtaaca tcgtttacaa acgacatact atatgtaaac    5040
aatctgtcac tgattaatta tttgccgttg tctgtattca ttattagacg agtcaccgac    5100
tatttggata gacgcatatg cgatcagata tttgctaata ataagtggta ttccattata    5160
accatcgacg ataagcaata tcctattcca tcaaactgta taggtatgtc ctctgccaag    5220
tacataaatt ctagcatcga gcaagatact ttaatccatg tttgtaacct cgagcatccg    5280
ttcgactcag tatacaaaaa aatgcagtcg tacaattctc tacctatcaa ggaacaaata    5340
ttgtacggta gaattgataa tataaatatg agcattagta tttctgtgga ttaatagatt    5400
tctagtatgg ggatcattaa tcatctctaa tctctaaata cctcataaaa cgaaaaaaaa    5460
gctattatca aatactgtac ggaatggatt cattctcttc tcttttatg aaactctgtt    5520 gtatatctac tgataaaact ggaagcaaaa aatctgataa aaagaataag aataagatca    5580
aggattatat ggaacacgat tattataaaa taacaatagt tcctggttcc tcttccacgt    5640
ctactagctc gtggtattat acacatgcct agtaatggat cc    5682
```

<210> SEQ ID NO 27

-continued

```
<211> LENGTH: 3884
<212> TYPE: DNA
<213> ORGANISM: Artificial Sequence
<220> FEATURE:
<223> OTHER INFORMATION: A56R modification cassette

<400> SEQUENCE: 27
ggatcctgat atcttcacgt agatataggt gtagtttcgc agtggccgtc ctggataata      60
ttatttatat gatgggtgga tatgatcagt ccccgtatag aagttcaaag gttatagcgt     120
acaatacatg tacaaattct tggatatatg atataccaga gctaaaatat cctcgttcta     180
attgtggggg actggctgat gacgaataca tttattgtat aggcggcata cgcgatcagg     240
attcatcgtt gacatctagt attgatagat ggaagccatc aaaaccatat tggcagaagt     300
atgctaaaat gcgcgaacca aaatgtgata tgggggttgc gatgttaaac ggattaatat     360
atgtcatggg tggaatcgtt aaaggtgaca cgtgtaccga cgcactagag agtttatcag     420
aagatggatg gatgaagcat caacgtcttc caataaaaat gtccaatatg tcgacgattg     480
ttcatgatgg caagatttat atatctggag gttacaacaa tagtagtgta gttaatgtaa     540
tatcgaatct agtccttagc tataattcga tatatgatga atggaccaaa ttatcatcat     600
taaacattcc tagaattaat cccgctctat ggtcagcgca taataaatta tatgtaggag     660
gaggaatatc tgatgatgtt cgaactaata catctgagac atacgacaaa gaaaaagatt     720
gttggacatt ggataatggt cacgtgttac cacgcaatta tataatgtat aaatgcgaac     780
cgattaaaca taaatatcca ttggaaaaaa cacagtacac gaatgatttt ctaaagtatt     840
tggaaagttt tataggtagt tgatagaaca aaatacataa ttttgtaaaa ataaatcact     900
ttttatacta atatgacacg attaccaata cttttgttac taatatcatt agtatacgct     960 acacctttc ctcagacatc taaaaaaata ggtgatgatg caactctatc atgtaatcga    1020
aataatacaa atgactacgt tgttatgagt gcttggtata aggagcccaa ttccattatt    1080
cttttagctg ctaaaagcga cgtcttgtat tttgataatt ataccaagga taaaatatct    1140
tacgactctc catcgatga tctagttaca actatcacaa ttaaatcatt gactgctaga    1200
gatgccggta cttatgtatg tgcattcttt atgacatcga ctacaaatga cactgataaa    1260
gtagattatg aagaatactc cacagagttg attgtaaata cagatagtga atcgactata    1320
gacataatac tatctggatc tacacattca ccggaaacta gttctgagaa acctgaggat    1380
atagataatt ttaattgctc gtcggtattc gaaatcgcga ctccggaacc aattactgat    1440
aatgtagaag atcatacaga caccgtcaca tacactagtg atagcattaa tacagtaagt    1500
gcatcataag tagggataac agggtaatcg atttattcaa caaagccacg ttgtgtctca    1560
aaatctctga tgttacattg cacaagataa aaatatatca tcatgaacaa taaaactgtc    1620
tgcttacata aacagtaata caaggggtgt tatgagccat attcaacggg aaacgtcttg    1680
ctcgaggccg cgattaaatt ccaacatgga tgctgattta tatgggtata aatgggctcg    1740
cgataatgtc gggcaatcag gtgcgacaat ctatcgattg tatgggaagc ccgatgcgcc    1800
agagttgttt ctgaaacatg gcaaaggtag cgttgccaat gatgttacag atgagatggt    1860
cagactaaac tggctgacgg aatttatgcc tcttccgacc atcaagcatt ttatccgtac    1920
tcctgatgat gcatggttac tcaccactgc gatccccggg aaaacagcat tccaggtatt    1980
agaagaatat cctgattcag gtgaaaatat tgttgatgcg ctggcagtgt tcctgcgccg    2040
gttgcattcg attcctgttt gtaattgtcc ttttaacagc gatcgcgtat ttcgtctcgc    2100
tcaggcgcaa tcacgaatga ataacggttt ggttgatgcg agtgattttg atgacgagcg    2160
```

-continued

```
taatggctgg cctgttgaac aagtctggaa agaaatgcat aagcttttgc cattctcacc    2220
ggattcagtc gtcactcatg gtgatttctc acttgataac cttattttg acgaggggaa    2280 attaataggt tgtattgatg ttggacgagt cggaatcgca gaccgatacc aggatcttgc    2340
catcctatgg aactgcctcg gtgagttttc tccttcatta cagaaacggc tttttcaaaa    2400
atatggtatt gataatcctg atatgaataa attgcagttt catttgatgc tcgatgagtt    2460
tttctaatca gaattggtta attggttgta acactggcac cgtcacatac actagtgata    2520
gcattaatac agtaagtgca tcatctggag aatccacaac agacgagact ccggaaccaa    2580
ttactgataa agaagaagat catacagtca cagacactgt ctcatacact acagtaagta    2640
catcatctgg aattgtcact actaaatcaa ccaccgatga tgcggatctt tatgatacgt    2700
acaatgataa tgatacagta ccaccaacta ctgtaggcgg tagtacaacc tctattagca    2760
attataaaac caaggacttt gtagaaatat ttggtattac cgcattaatt atattgtcgg    2820
ccgtggcaat attctgtatt acgtattata tatataataa acgttcacgt aaatacaaaa    2880
cagagaacaa agtctagatt tttgacttac ataaatgtct gggatagtaa aatctatcat    2940
attgagcgga ccatctggtt taggaaagac agccatagcc aaaagactat gggaatatat    3000
ttggatttgt ggtgtcccat accactagat ttcctcgtcc tatggaacga gaaggtgtcg    3060
attaccatta cgttaacaga gaggccatct ggaagggaat agccgccgga aactttctag    3120
aacatactga gttttagga aatatttacg gaacttctaa aactgctgtg aatacagcgg    3180
ctattaataa tcgtatttgt gtgatggatc taaacatcga tggcgttaga agtcttaaaa    3240
atacgtacct aatgccttac tcggtgtata taagacctac ctctcttaaa atggttgaga    3300
ccaagcttcg tcgtagaaac actgaagcgg atgatgagat tcatcgtcgt gtgatgttgg    3360
caaaaactga catggatgag gcaggtgaag ccggtctatt cgacactatt attattgaag    3420
atgatgtgaa tttagcatat agtaagttaa ttcagatact acaggaccgt attagaatgt    3480
attttaacac taattagaga cttaagactt aaaacttgat aattaataat ataactcgtt    3540
tttatatgtg tctatttcaa cgtctaatgt attagttaaa tattaaaact taccacgtaa    3600
aacttaaaat ttaaaatgat atttcattga cagatagatc acacattatg aactttcaag    3660
gacttgtgtt aactgacaat tgcaaaaatc aatgggtcgt tggaccatta ataggaaaag    3720
gtggattcgg tagtatttat actactaatg acaataatta tgtagtaaaa atagagccca    3780
aagctaacgg atcattattt accgaacagg cattttatac tagagtactt aaaccatccg    3840
ttatcgaaga atggaaaaaa tctcacaata taaagcacgg atcc                    3884
```

```
<210> SEQ ID NO 28
<211> LENGTH: 3509
<212> TYPE: DNA
<213> ORGANISM: Artificial Sequence
<220> FEATURE:
<223> OTHER INFORMATION: B5R modification cassette

<400> SEQUENCE: 28
tctagaatat taactatcgt actatataca acgaaacatc tatttacgac gctgtcagtt     60
ataatgcgta taatacgttg gtctatctat taaacaaaaa tggtgatttt gagacgatta    120
ctactagtgg atgtacatgt atttcggaag cagtcgcaaa caacaacaaa ataataatgg    180
aagtactatt gtctaaacga ccatctttga aaattatgat acagtctatg atagcaatta    240
ctaaacataa acagcataat gcagatttat tgaaaatgtg tataaaatat actgcgtgta    300
```

-continued

```
tgaccgatta tgatactctt atagatgtac agtcgctaca gcaatataaa tggtatattt    360
taagatgttt cgatgaaata gatatcatga agagatgtta tataaaaaat aaaactgtat    420
tccaattagt tttttgtatc aaagacatta atactttaat gagatacggt aaacatcctt    480
ctttcgtgaa gtgcactagt ctcgacgtat acggaagtcg tgtacgtaat atcatagcat    540
ctattagata tcgtcagaga ttaattagtc tattatccaa gaagctggat gcgggagata    600
aatggtcgtg ttttcctaac gaaataaaat ataaaatatt ggaaaacttt aacgataacg    660
aactatccac atatctaaaa atcttataaa cattattaaa atataaaatc taagtggata    720
aaatcacact acatcattgt ttccttttag tgctcgacag tgtatactat ttttaacgct    780
cataaataaa aatgaaaacg atttccgttg ttacgttgtt atgcgtacta cctgctgttg    840
tttattcaac atgtactgta cccactatga ataacgctaa attaacgtct accgaaacat    900
cgtttaatga taaacagaaa gttacattta catgtgatca gggatatcat tctttggatc    960
caaatgctgt ctgtgaaaca gataaatgga aatacgaaaa tccatgcaag aaaatgtgca    1020
cagtttctga ttatgtctct gaattatatg ataagccatt atacgaagtg aattccacca    1080
tgacactaag ttgcaacggc gaaacaaaat attttcgttg cgaagaaaaa aatggaaata    1140
cttcttggaa tgatactgtt acgtgtccta atgcggaatg tcaacctctt caattagaac    1200
acggatcgtg tcaaccagtt aaagaaaaat actcatttgg ggaatatatg actatcaact    1260
gtgatgttgg atatgaggtt attggtgctt cgtacataag ttgtacagct aattcttgga    1320
atgttattcc atcatgtcaa caaaaatgtg atataccgtc tctatctaac ggattaattt    1380
ccggatctac attttctatc ggtggcgtta tacatcttag ttgtaaaagt ggtttttatac   1440 taacggggtc tccatcatcc acatgtatcg acggtaaatg gaatcccata ctcccaacat    1500
gtgtactaag tagggataac agggtaatcg atttattcaa caaagccacg ttgtgtctca    1560
aaatctctga tgttacattg cacaagataa aaatatatca tcatgaacaa taaaactgtc    1620
tgcttacata aacagtaata caaggggtgt tatgagccat attcaacggg aaacgtcttg    1680
ctcgaggccg cgattaaatt ccaacatgga tgctgattta tatgggtata aatgggctcg    1740
cgataatgtc gggcaatcag gtgcgacaat ctatcgattg tatgggaagc ccgatgcgcc    1800
agagttgttt ctgaaacatg gcaaaggtag cgttgccaat gatgttacag atgagatggt    1860
cagactaaac tggctgacgg aatttatgcc tcttccgacc atcaagcatt ttatccgtac    1920
tcctgatgat gcatggttac tcaccactgc gatccccggg aaaacagcat tccaggtatt    1980
agaagaatat cctgattcag gtgaaaatat tgttgatgcg ctggcagtgt tcctgcgccg    2040
gttgcattcg attcctgttt gtaattgtcc ttttaacagc gatcgcgtat ttcgtctcgc    2100
tcaggcgcaa tcacgaatga ataacggttt ggttgatgcg agtgattttg atgacgagcg    2160
taatggctgg cctgttgaac aagtctggaa agaaatgcat aagcttttgc cattctcacc    2220
ggattcagtc gtcactcatg gtgatttctc acttgataac cttatttttg acgaggggaa    2280
attaataggt tgtattgatg ttggacgagt cggaatcgca gaccgatacc aggatcttgc    2340
catcctatgg aactgcctcg gtgagttttc tccttcatta cagaaacggc tttttcaaaa    2400
atatggtatt gataatcctg atatgaataa attgcagttt catttgatgc tcgatgagtt    2460
tttctaatca gaattggtta attggttgta acactggcaa tgtatcgacg gtaaatggaa    2520
tcccatactc ccaacatgtg tacgatctaa cgaaaaattt gatccagtgg atgatggtcc    2580
cgacgatgag acagatttga gcaaactctc gaaagacgtt gtacaatatg aacaagaaat    2640
agaatcgtta gaagcaactt atcatataat catagtggcg ttaacaatta tgggcgtcat    2700
```

-continued

```
attttttaatc tccgttatag tattagtttg ttcctgtgac aaaaataatg accaatataa    2760
gttccataaa ttgctaccgt aaatataaat ccgttaaaat aattaataat taataacgaa    2820
caagtatcaa aagattaaag acttatagct agaatcaatt gagatgtctt cttcagtgga    2880
tgttgatatc tacgatgccg ttagagcatt tttactcagg cactattata acaagagatt    2940
tattgtgtat ggaagaagta acgccatatt acataatata tacaggctat ttacaagatg    3000
cgccgttata ccgttcgatg atatagtacg tactatgcca aatgaatcac gtgttaaaca    3060
atgggtgatg gatacactta atggtataat gatgaatgaa cgcgatgttt ctgtaagcgt    3120
tggcaccgga atactattca tggaaatgtt tttcgattac aataaaaata gtatcaacaa    3180
tcaactaatg tatgatataa ttaatagcgt atctataatt ctagctaatg agagatatag    3240
aagcgctttt aacgacgatg gtatatacat ccgtagaaat atgattaaca agttgtacgg    3300
atacgcatct ctaactacta ttggcacgat cgctggaggt gtttgttatt atctgttgat    3360
gcatctagtt agtttgtata aataattatt tcaatatact agttaaaatt ttaagatttt    3420
aaatgtataa aaaactaata acgtttttat ttgtaatagg tgcattagca tcctattcga    3480
ataatgagta cactccgttt aattctaga                                       3509
```

<210> SEQ ID NO 29
<211> LENGTH: 6209
<212> TYPE: DNA
<213> ORGANISM: Artificial Sequence
<220> FEATURE:
<223> OTHER INFORMATION: F12-13L modification cassette

<400> SEQUENCE: 29

```
ggatccagac aaacaattaa ctattttgtc tctgtttta acacctccac agtttttaat       60
ttctttagta atgaaattat tcacaatatc agtatcttct ttatctacca gagattttac      120
taacttgata accttggctg tctcattcaa tagggtagta atatttgtat gtgtgatatt      180
gatatctttt tgaattgttt cttttagaag tgattctttg atggtgccag catacgaatt      240
acaataatgc agaaactcgg ttaacatgca ggaattatag taagccaatt ccaattgttg      300
cctgtgttgt attagagtgt caatatgagc aatggtgtcc ttgcgtttct ctgatagaat      360
gcgagcagcg attttggcgt tatcatttga cgatatttct ggaatgacga atcctgtttc      420
tactaacttt ttggtaggac aaagtgaaac aatcaagaag atagcttctc ctcctatttg      480
tggaagaaat tgaactcctc tagatgatct actgacgata gtatctcctt gacagatatt      540
ggaccgaatt acagaagtac ctggaatgta aagccctgaa accccctcat tttttaagca      600
gattgttgcc gtaaatcctg cactatgccc aagatagaga gctcctttgg tgaatccatc      660
tctatgtttc agtttaacca agaaacagtc agctggtcta aaatttccat ctctatctaa      720
tacagcatct aacttgatgt caggaactat gaccggttta atgttatatg taacattgag      780
taaatcctta agttcataat catcactgtc atcagttatg tacgatccaa acaatgtttc      840
taccggcata gtggatacga agatgctatc catcagaatg tttccctgat tagtattttc      900
tatatagcta ttcttcttta aacgatttc caaatcagta actatgttca ttttttttagg      960 agtaggacgc ctagccagta tggaagagga ttttctagat cctctcttca acatctttga     1020
tctcgatgga atgcaaaacc ccatagtgaa acaaccaacg ataaaaataa tattgttttt     1080
cactttttat aatttttacca tctgactcat ggattcatta atatctttat aagagctact     1140
aacgtataat tctttataac tgaactgaga tatatacacc ggatctatgg tttccataat     1200
```

```
tgagtaaatg aatgctcggc aataactaat ggcaaatgta taaaacaacg aaattatact   1260
agagttgtta aagttaatat tttctatgag ctgttccaat aaattatttg ttgtgactgc   1320
gttcaagtca taaatcatct tgatactatc cagtaaacag tctttaagtt ctggaatatt   1380
atcatcccat tgtaaagccc ctaattcgac tatcgaatat cctgctctga tagcagtttc   1440
aatatcgacg gacgtcaata ctgtaataaa ggtggtagta ttgtcatcat cgtgataaac   1500
tacgggaata tggtcgttag taggtacggt gactttacac aacgcgatat ataactttcc   1560
ttttgtacca tttttaacgt agttgggacg tcctgcaggg tattgttttg aagaaatgat   1620
atcgagaaca gatttgatac gatatttgtt ggattcctga ttattcacta taatataatc   1680
tagacagata gatggattcga taaatagaga aggtatatcg ttggtaggat aatacatccc   1740
cattccagta ttctcggata ctctattgat gacactagtt aagaacatgt cttctattct   1800
agaaaacgaa aacatcctac atggactcat taaaacttct aacgctcctg attgtgtctc   1860
gaatgcctcg tacaaggatt tcaaggatgc catagattct ttgacctaag tagggataac   1920
agggtaatcg atttattcaa caaagccacg ttgtgtctca aaatctctga tgttacattg   1980
cacaagataa aaatatatca tcatgaacaa taaaactgtc tgcttacata aacagtaata   2040
caaggggtgt tatgagccat attcaacggg aaacgtcttg ctcgaggccg cgattaaatt   2100
ccaacatgga tgctgattta tatgggtata aatgggctcg cgataatgtc gggcaatcag   2160
gtgcgacaat ctatcgattg tatggggaagc ccgatgcgcc agagttgttt ctgaaacatg   2220
gcaaaggtag cgttgccaat gatgttacag atgagatggt cagactaaac tggctgacgg   2280
aatttatgcc tcttccgacc atcaagcatt ttatccgtac tcctgatgat gcatggttac   2340
tcaccactgc gatccccggg aaaacagcat tccaggtatt agaagaatat cctgattcag   2400
gtgaaaatat tgttgatgcg ctggcagtgt tcctgcgccg gttgcattcg attcctgttt   2460
gtaattgtcc ttttaacagc gatcgcgtat ttcgtctcgc tcaggcgcaa tcacgaatga   2520
ataacggttt ggttgatgcg agtgattttg atgacgagcg taatggctgg cctgttgaac   2580
aagtctggaa agaaatgcat aagctttgc cattctcacc ggattcagtc gtcactcatg   2640
gtgatttctc acttgataac cttatttttg acgaggggaa attaataggt tgtattgatg   2700
ttggacgagt cggaatcgca gaccgatacc aggatcttgc catcctatgg aactgcctcg   2760
gtgagttttc tccttcatta cagaaacggc tttttcaaaa atatggtatt gataatcctg   2820
atatgaataa attgcagttt catttgatgc tcgatgagtt tttctaatca gaattggtta   2880
attggttgta acactggcaa tgcctcgtac aaggatttca aggatgccat agattctttg   2940
accaacgatt tagaattgcg tttagcatct gattttttta ttaaatcgaa tggtcggctc   3000
tctggtttgc taccccaatg ataacaatag tcttgtaaag ataaaccgca agaaaattta   3060
tacgcatcca tccaaataac cctagcacca tcggatgata ttaatgtatt attatagatt   3120
ttccatccac aattattggg ccagtatact gttagcaacg gtatatcgaa tagattactc   3180
atgtaaccta ctagaatgat agttcgtgta ctagtcataa tatctttaat ccaatctaag   3240
aaatttaaaa ttagattttt tacactgtta aagttaacaa aggtattacc cggatacgtg   3300
gatatcatat atggcattgg tccattatca gtaatagctc cataaactga tacggcgatg   3360 gttttttatat gtgtttgatc taacgaggaa gaaattcgcg cccacaattc atctctagat   3420
atgtatttaa tatcaaacgg taacacatca atttcgggac gcgtatatgt ttctaaattt   3480
ttaatccaaa tataatgatg acctatatgc cctattatca tactgtcaac tatagtcacac   3540 ctagagaact tacgatacat ctgtttccta taatcgttaa attttacaaa tctataacat   3600
```

-continued

```
gctaaacctt ttgacgacaa ccattcatta atttctgata tggaatctgt attctcgata    3660
ccgtattgtt ctaaagccag tgctatatct ccctgttcgt gggaacgctt tcgtataata    3720
tcgatcaacg gataatctga agtttttgga gaataatatg actcatgatc tatttcgtcc    3780
ataaacaatc tagacatagg aattggaggc gatgatctta attttgtgca atgagtcgtc    3840
aatcctataa cttctaatat tgtaatattc atcatcgaca taacactatc tatgttatca    3900
tcgtatatta gtataccacg gccttcttca tttcgtgcca aaataatata cagtcttaaa    3960
taattacgca atatctcaat agtttcataa ttgttagctg ttttcatcaa ggtttgtatc    4020
ctgtttaaca tgatggcgtt ctataacgtc tctattttct atttttaatt ttttaaattt    4080
ttaacgattt actgtggcta gatacccaat ctctctcaaa tatttttta gcctcgctta    4140 caagctgttt atctatacta ttaaaactga cgaatccgtg attttggtaa tgggttccgt    4200
cgaaatttgc cgaagtgata tgaacatatt cgtcgtcgac tatcaacaat tttgtattat    4260
tctgaatagt gaaaaccttc acagatagat cattttgaac acacaacgcg tctagacttc    4320
tggcggttgc catagaatat acgtcgttct tatcccaatt accaactaga agtctgatct    4380
taactcctct attaatggct gcttctataa tggagttgta aatgtcaggc caatagtagc    4440
tattaccgtc gacacgtgta gtgggaacta tggccaaatg ttcaatatct atactagtct    4500
tagccgactt gagtttatca ataactacat cagtgtctag atctctagaa tatcccaata    4560
ggtgttctgg agaatcagta aagaacactc cacctatagg attcttaata tgatacgcag    4620
tgctaactgg cagacaacaa gccgcagagc ataaattcaa ccatgaattt tttgcgctat    4680
taaaggcttt aaaagtatca aatcttctac gaagatctgt ggccagcggg ggataatcag    4740
aatatacacc taacgtttta atcgtatgta tagatcctcc agtaaatgac gcgtttccta    4800
cataacatct ttcatcatct gacacccaaa aacaaccgag tagtagtccc acattatttt    4860
ttttatctat attaacggtt ataaaattta tatccgggca gtgactttgt agctctccca    4920
gatttctttt ccctcgttca tctagcaaaa ctattatttt aatccctttt tcagatgcct    4980
cttttagttt atcaaaaata agcgcgcccc tagtcgtact cagaggatta caacaaaaag    5040
atgctatgta tatatatttc ttagctagag tgataatttc gttaaaacat tcaaatgttg    5100
ttaaatgatc ggatctaaaa tccatatttt ctggtagtgt ttctaccagc ctacattttg    5160
ctcccgcagg taccggtgca aatggccaca tttagttaac ataaaaactt atacatcctg    5220
ttctatcaac gattctagaa tatcatcggc tatatcgcta aaattttcat caaagtcgac    5280
atcacaacct aactcagtca atatattaag aagttccatg atgtcatctt cgtctatttc    5340
tatatccgta tccattgtag attgttgacc gattatcgag tttaaatcat tactaatact    5400
caatccttca gaatacaatc tgtgtttcat tgtaaattta taggcggtgt atttaagttg    5460
gtagattttc aattatgtat taatatagca acagtagttt ttgctcctcc ttgattctag    5520
catcctcttc attattttct tctacgtaca taagcatgtc caatacgtta gacaacacac    5580
cgacgatggc ggccgccaca gacacgaata tgactaaacc gatgaccatt taaaaacccc    5640
tctctagctt tcacttaaac tgtatcgatc attcttttag cacatgtata atataaaaac    5700
attattctat ttcgaattta ggcttccaaa aatttttcat ccgtaaaccg ataataatat    5760
atatagactt gttaatagtc ggaataaata gattaatgct taaactatca tcatctccac    5820
gattagagat acaatattta cattcttttt gctgtttcga aactttatca atacacgtta    5880
atacaaaccc aggaaggaga tattgaaact gaggctgttg aaaatgaaac ggtgaataca    5940
```

-continued

```
ataattcaga taatgtaaaa tcatgattcc gtattctgat gatattagaa ctgctaatgg    6000
atgtcgatgg tatgtatcta ggagtatcta ttttaacaaa gcatcgattt gctaatatac    6060
aattatcatt ttgattaatt gttattttat tcatattctt aaaaggtttc atatttatca    6120
attcttctac attaaaaatt tccattttta atttatgtag ccccgcaata ctcctcatta    6180
cgtttcattt tttgtctata ataggatcc                                      6209

<210> SEQ ID NO 30
<211> LENGTH: 5828
<212> TYPE: DNA
<213> ORGANISM: Artificial Sequence
<220> FEATURE:
<223> OTHER INFORMATION: pUC57-A33R-rKanI plasmid

<400> SEQUENCE: 30
ggatccaatg ttaaaactac aaaaatgcgt aatgttagcc cgtcctaata ttggtacgtg      60
tctataagtt tggcatagta gaataataga cgtgtttaaa tgccttccga agtttaagaa     120
ttctattaga gtattgcatt ttgatagttt atcacctaca tcatcaaaaa taagtaaaaa     180
gtgtgctgat tttttatgat tttgtgcgac agcaatacat ttttctatgt tacttttagt     240
tcgtatcaga ttatattcta gagattcctg actactaacg aaattaatat gatttggcca     300
aatgtatcca tcataatctg ggttataaac gggtgtaaac aagaatatat gtttatattt     360
tttaactagt gtagaaaaca gagatagtaa atagatagtt tttccagatc cagatcctcc     420
cgttaaaacc attctaaacg gcatttttaa taaattttct cttgaaaatt gttttttcttg    480 gaaacaattc ataattatat ttacagttac taaattaatt tgataataaa tcaaaatatg     540
gaaaactaag gttgttagta gggaggagaa caaagaaggc acatcgtgat ataaataaca     600
tttattatca tgatgacacc agaaaacgac gaagagcaga catctgtgtt ctccgctact     660
gtttacggag acaaaattca gggaaagaat aaacgcaaac gcgtgattgg tctatgtatt     720
agaatatcta tggttatttc actactatct atgattacca tgtccgcgtt tctcatagtg     780
cgcctaaatc aatgcatgtc tgctaacgag gctgctatta ctgacgccgc tgttgccgtt     840
gctgctgcat catctactca tagaaaggtt gcgtctagca ctacgcaata tgatcacaaa     900
gaaagctgta atggtttata ttaccagggt tcttgttata tattacattc agactaccag     960
ttattctcgg atgctaaagc aaattgcact gcggaatcat caacactaag tagggataac    1020
agggtaatcg atttattcaa caaagccacg ttgtgtctca aaatctctga tgttacattg    1080
cacaagataa aaatatatca tcatgaacaa taaaactgtc tgcttacata aacagtaata    1140
caaggggtgt tatgagccat attcaacggg aaacgtcttg ctcgaggccg cgattaaatt    1200
ccaacatgga tgctgattta tatgggtata aatgggctcg cgataatgtc gggcaatcag    1260
gtgcgacaat ctatcgattg tatgggaagc ccgatgcgcc agagttgttt ctgaaacatg    1320
gcaaaggtag cgttgccaat gatgttacag atgagatggt cagactaaac tggctgacgg    1380
aatttatgcc tcttccgacc atcaagcatt ttatccgtac tcctgatgat gcatggttac    1440
tcaccactgc gatccccggg aaaacagcat tccaggtatt agaagaatat cctgattcag    1500
gtgaaaatat tgttgatgcg ctggcagtgt tcctgcgccg gttgcattcg attcctgttt    1560
gtaattgtcc ttttaacagc gatcgcgtat ttcgtctcgc tcaggcgcaa tcacgaatga    1620
ataacggttt ggttgatgcg agtgattttg atgacgagcg taatggctgg cctgttgaac    1680
aagtctggaa agaaatgcat aagctttttgc cattctcacc ggattcagtc gtcactcatg    1740
gtgatttctc acttgataac cttatttttg acgaggggaa attaataggt tgtattgatg    1800
```

-continued

```
ttggacgagt cggaatcgca gaccgatacc aggatcttgc catcctatgg aactgcctcg     1860
gtgagttttc tccttcatta cagaaacggc tttttcaaaa atatggtatt gataatcctg     1920
atatgaataa attgcagttt catttgatgc tcgatgagtt tttctaatca gaattggtta     1980
attggttgta acactggcaa ttctcggatg ctaaagcaaa ttgcactgcg gaatcatcaa     2040
cactacccaa taaatccgat gtcttgatta cctggctcat tgattatgtt gaggatacat     2100
ggggatctga tggtaatcca attacaaaaa ctacatccga ttatcaagat tctgatatat     2160
cacaagaagt tagaaagtat ttttgtgtta aaacaatgaa ctaatattta tttttgtaca     2220
ttaataaatg aaatcgctta atagacaaac tgtaagtagg tttaagaagt tgtcggtgcc     2280
ggccgctata atgatgatac tctcaaccat tattagtggc ataggaacat ttctgcatta     2340
caaagaagaa ctgatgccta gtgcttgcgc caatggatgg atacaatacg ataaacattg     2400
ttatttagat actaacatta aaatgtctac agataatgcg gtttatcagt gtcgtaaatt     2460
acgagctaga ttgcctagac ctgatactag acatctgaga gtattgttta gtatttttta     2520
taaagattat tgggtaagtt taaaaaagac caataataaa tggttagata ttaataatga     2580
taaagatata gatattagta aattaacaaa ttttaaacaa ctaaacagta cgacggatgc     2640
tgaagcgtgt tatatataca agtctggaaa actggttaaa acagtatgta aaagtactca     2700
atctgtacta tgtgttaaaa aattctacaa gtgacaacaa aaaatgaatt aataataagt     2760
cgttaacgta cgccgccatg gacgccgcgt ttgttattac tccaatgggt gtgttgacta     2820
taacagatac attgtatgat gatctcgata tctcaatcat ggactttata ggaccataca     2880
ttataggtaa cataaaaact gtccaaatag atgtacggga tataaaatat tccgacatgc     2940
aaaaatgcta ctttagctat aagggtaaaa tagttcctca ggattctaat gatttggcta     3000
gattcaacat ttatagcatt tgtgccgcat acagatcaaa aaataccatc atcatagcat     3060
gcgactatga tatcatgtta gatatagaag ataaacatca gccattttat ctattcccat     3120
ctattgatgt ttttaacgct acaggatcca tcccaatggc gcgccgagct tggcgtaatc     3180
atggtcatag ctgtttcctg tgtgaaattg ttatccgctc acaattccac acaacatacg     3240
agccggaagc ataaagtgta aagcctgggg tgcctaatga gtgagctaac tcacattaat     3300
tgcgttgcgc tcactgcccg ctttccagtc gggaaacctg tcgtgccagc tgcattaatg     3360
aatcggccaa cgcgcgggga gaggcggttt gcgtattggg cgctcttccg cttcctcgct     3420
cactgactcg ctgcgctcgg tcgttcggct gcggcgagcg gtatcagctc actcaaaggc     3480
ggtaatacgg ttatccacag aatcagggga taacgcagga agaacatgt gagcaaaagg     3540 ccagcaaaag gccaggaacc gtaaaaaggc cgcgttgctg gcgtttttcc ataggctccg     3600 ccccctgac gagcatcaca aaatcacaaa aatcgacgct caagtcagag gtggcgaaac     3660
ccgacaggac tataaagata ccaggcgttt cccctggaa gctccctcgt gcgctctct     3720 gttccgaccc tgccgcttac cggatacctg tccgccttc tcccttcggg aagcgtggcg     3780
ctttctcata gctcacgctg taggtatctc agttcggtgt aggtcgttcg ctccaagctg     3840
ggctgtgtgc acgaaccccc cgttcagccc gaccgctgcg ccttatccgg taactatcgt     3900
cttgagtcca acccggtaag acacgactta tcgccactgg cagcagccac tggtaacagg     3960
attagcagag cgaggtatgt aggcggtgct acagagttct tgaagtggtg gcctaactac     4020
ggctacacta agaacagt atttggtatc tgcgctctgc tgaagccagt taccttcgga     4080
aaaagagttg gtagctcttg atccggcaaa caaaccaccg ctggtagcgg tggttttttt     4140
```

-continued

```
gtttgcaagc agcagattac gcgcagaaaa aaaggatctc aagaagatcc tttgatcttt       4200
tctacggggt ctgacgctca gtggaacgaa aactcacgtt aagggatttt ggtcatgaga       4260
ttatcaaaaa ggatcttcac ctagatcctt ttaaattaaa aatgaagttt taaatcaatc       4320
taaagtatat atgagtaaac ttggtctgac agttaccaat gcttaatcag tgaggcacct       4380
atctcagcga tctgtctatt tcgttcatcc atagttgcct gactccccgt cgtgtagata       4440
actacgatac gggagggctt accatctggc cccagtgctg caatgatacc gcgagaccca       4500
cgctcaccgg ctccagattt atcagcaata aaccagccag ccggaagggc cgagcgcaga       4560
agtggtcctg caactttatc cgcctccatc cagtctatta attgttgccg ggaagctaga       4620
gtaagtagtt cgccagttaa tagtttgcgc aacgttgttg ccattgctac aggcatcgtg       4680
gtgtcacgct cgtcgtttgg tatggcttca ttcagctccg gttcccaacg atcaaggcga       4740
gttacatgat cccccatgtt gtgcaaaaaa gcggttagct ccttcggtcc tccgatcgtt       4800
gtcagaagta agttggccgc agtgttatca ctcatggtta tggcagcact gcataattct       4860
cttactgtca tgccatccgt aagatgcttt tctgtgactg gtgagtactc aaccaagtca       4920
ttctgagaat agtgtatgcg cgaccgagt tgctcttgcc cggcgtcaat acgggataat       4980
accgcgccac atagcagaac tttaaaagtg ctcatcattg gaaaacgttc ttcggggcga       5040
aaactctcaa ggatcttacc gctgttgaga tccagttcga tgtaacccac tcgtgcaccc       5100
aactgatctt cagcatcttt tactttcacc agcgtttctg ggtgagcaaa aacaggaagg       5160
caaaatgccg caaaaaaggg aataagggcg acacggaaat gttgaatact catactcttc       5220 cttttt caat attattgaag catttatcag ggttattgtc tcatgagcgg atacatattt       5280
gaatgtattt agaaaaataa acaaataggg gttccgcgca catttccccg aaaagtgcca       5340
cctgacgtct aagaaaccat tattatcatg acattaacct ataaaaatag gcgtatcacg       5400
aggccctttc gtctcgcgcg tttcggtgat gacggtgaaa acctctgaca catgcagctc       5460
ccggagacgg tcacagcttg tctgtaagcg gatgccggga gcagacaagc ccgtcagggc       5520
gcgtcagcgg gtgttggcgg gtgtcggggc tggcttaact atgcggcatc agagcagatt       5580
gtactgagag tgcaccatat gcggtgtgaa ataccgcaca gatgcgtaag gagaaaatac       5640
cgcatcaggc gccattcgcc attcaggctg cgcaactgtt gggaagggcg atcggtgcgg       5700
gcctcttcgc tattacgcca gctggcgaaa ggggatgtg ctgcaaggcg attaagttgg       5760
gtaacgccag ggtttttcca gtcacgacgt tgtaaaacga cggccagtga attgacgcgt       5820
attgggat                                                                5828
```

<210> SEQ ID NO 31
<211> LENGTH: 5877
<212> TYPE: DNA
<213> ORGANISM: Artificial Sequence
<220> FEATURE:
<223> OTHER INFORMATION: pUC57-A34R-rKanI plasmid

<400> SEQUENCE: 31

```
ggatccagta gggaggagaa caaagaaggc acatcgtgat ataaataaca tttattatca         60
tgatgacacc agaaaacgac gaagagcaga catctgtgtt ctccgctact gtttacggag        120
acaaaattca gggaaagaat aaacgcaaac gcgtgattgg tctatgtatt agaatatcta        180
tggttatttc actactatct atgattacca tgtccgcgtt tctcatagtg cgcctaaatc        240
aatgcatgtc tgctaacgag gctgctatta ctgacgccgc tgttgccgtt gctgctgcat        300
catctactca tagaaaggtt gcgtctagca ctacgcaata tgatcacaaa gaaagctgta        360
```

-continued

```
atggtttata ttaccagggt tcttgttata tattacattc agactaccag ttattctcgg      420
atgctaaagc aaattgcact gcggaatcat caacactacc caataaatcc gatgtcttga      480
ctacctggct cattgattat gttgaggata catggggatc tgatggtaat ccaattacaa      540
aaactacatc caattatcaa gattctgatg tatcacaaga agttagaaag tatttttgtg      600
ttaaaacaat gaactaatat ttatttttgt acattaataa atgaaatcgc ttaatagaca      660
aactgtaagt aggtttaaga agttgtcggt gccggccgct ataatgatga tactctcaac      720
cattattagt ggcataggaa catttctgca ttacaaagaa gaactgatgc ctagtgcttg      780
cgccaatgga tggatacaat acgataaaca ttgttattta gatactaaca ttaaaatgtc      840
tacagataat gcggtttatc agtgtcgtaa attacgagct agattgccta gacctgatac      900
tagacatctg agagtattgt ttagtatttt ttataaagat tattgggtaa gtttaaaaaa      960
gaccaataat aaatggttag atattaataa tgataaagat atagatatta gtaaattaac     1020
aaattttaaa caactaaaca gtacgacgga tgctgaagcg tgttatatat acaagtctgg     1080
aaaacttaag tagggataac agggtaatcg atttattcaa caaagccacg ttgtgtctca     1140
aaatctctga tgttacattg cacaagataa aaatatatca tcatgaacaa taaaactgtc     1200
tgcttacata aacagtaata caaggggtgt tatgagccat attcaacggg aaacgtcttg     1260
ctcgaggccg cgattaaatt ccaacatgga tgctgattta tatgggtata aatgggctcg     1320
cgataatgtc gggcaatcag gtgcgacaat ctatcgattg tatgggaagc ccgatgcgcc     1380
agagttgttt ctgaaacatg gcaaaggtag cgttgccaat gatgttacag atgagatggt     1440
cagactaaac tggctgacgg aatttatgcc tcttccgacc atcaagcatt ttatccgtac     1500
tcctgatgat gcatggttac tcaccactgc gatccccggg aaaacagcat tccaggtatt     1560
agaagaatat cctgattcag gtgaaaatat tgttgatgcg ctggcagtgt tcctgcgccg     1620
gttgcattcg attcctgttt gtaattgtcc ttttaacagc gatcgcgtat ttcgtctcgc     1680
tcaggcgcaa tcacgaatga taacggtttg gttgatgcga gtgattttg atgacgagcg     1740 taatggctgg cctgttgaac aagtctggaa agaaatgcat aagctttgc cattctcacc     1800 ggattcagtc gtcactcatg gtgatttctc acttgataac cttattttg acgaggggaa     1860 attaataggt tgtattgatg ttggacgagt cggaatcgca gaccgatacc aggatcttgc     1920
catcctatgg aactgcctcg gtgagttttc tccttcatta cagaaacggc tttttcaaaa     1980
atatggtatt gataatcctg atatgaataa attgcagttt catttgatgc tcgatgagtt     2040
tttctaatca gaattggtta attggttgta acactggcaa cgacggatgc tgaagcgtgt     2100
tatatataca agtctggaaa actggttgaa cagtatgtaa aagtactcaa tctgtactat     2160
gtgttaaaaa attctacaag tgacaacaaa aaatgaatta ataataagtc gttaacgtac     2220
gccgccatgg acgccgcgtt tgttattact ccaatgggtg tgttgactat aacagataca     2280
ttgtatgatg atctcgatat ctcaatcatg gactttatag gaccatacat tataggtaac     2340
ataaaaactg tccaaataga tgtacgggat ataaaatatt ccgacatgca aaaatgctac     2400
tttagctata agggtaaaat agttcctcag gattctaatg atttggctag attcaacatt     2460
tatagcattt gtgccgcata cagatcaaaa aataccatca tcatagcatg cgactatgat     2520
atcatgttag atatagaaga taaacatcag ccattttatc tattcccatc tattgatgtt     2580
tttaacgcta caatcataga agcgtataac ctgtatacag ctggagatta tcatctaatc     2640
atcaatcctt cagataatct gaaaatgaaa ttgtcgttta attcttcatt ctgcatatca     2700
```

-continued

```
gacggcaatg gatggatcat aattgatggg aaatgcaata gtaatttttt atcataaaag    2760
ttgtaaagta aataataaaa caataaatat tgaactagta gtacgtatat tgagcaatca    2820
gaaatgatgc tggtacctct tatcacggtg accgtagttg cgggaacaat attagtatgt    2880
tatatattat atatttgtag gaaaaagata cgtactgtct ataatgacaa taaaattatc    2940
atgacaaaat taaaaaagat aaagagttct aattccagca aatctagtaa atcaactgat    3000
agcgaatcag actgggagga tcactgtagt gctatggaac aaaacaatga cgtagataat    3060
atttctagga atgagatatt ggacgatgat agcttcgctg gtagtttaat atgggataac    3120
gaatccaatg ttatagcgcc tagcacagaa cacatttacg atagtgttgc tggaagcacg    3180
ctgctaataa atggatccat cccaatggcg cgccgagctt ggcgtaatca tggtcatagc    3240
tgtttcctgt gtgaaattgt tatccgctca caattccaca caacatacga gccggaagca    3300
taaagtgtaa agcctggggt gcctaatgag tgagctaact cacattaatt gcgttgcgct    3360
cactgcccgc tttccagtcg ggaaacctgt cgtgccagct gcattaatga atcggccaac    3420
gcgcggggag aggcggtttg cgtattgggc gctcttccgc ttcctcgctc actgactcgc    3480
tgcgctcggt cgttcggctg cggcgagcgg tatcagctca ctcaaaggcg gtaatacggt    3540
tatccacaga atcaggggat aacgcaggaa agaacatgtg agcaaaaggc cagcaaaagg    3600
ccaggaaccg taaaaaggcc gcgttgctgg cgtttttcca taggctccgc ccccctgacg    3660
agcatcacaa aatcacaaaa atcgacgctc aagtcagagg tggcgaaacc cgacaggact    3720
ataaagatac caggcgtttc cccctggaag ctccctcgtg cgctctcctg ttccgaccct    3780
gccgcttacc ggatacctgt ccgcctttct cccttcggga agcgtggcgc tttctcatag    3840
ctcacgctgt aggtatctca gttcggtgta ggtcgttcgc tccaagctgg gctgtgtgca    3900
cgaacccccc gttcagcccg accgctgcgc cttatccggt aactatcgtc ttgagtccaa    3960
cccggtaaga cacgacttat cgccactggc agcagccact ggtaacagga ttagcagagc    4020
gaggtatgta ggcggtgcta cagagttctt gaagtggtgg cctaactacg gctacactag    4080
aagaacagta tttggtatct gcgctctgct gaagccagtt accttcggaa aaagagttgg    4140
tagctcttga tccggcaaac aaaccaccgc tggtagcggt ggtttttttg tttgcaagca    4200
gcagattacg cgcagaaaaa aaggatctca agaagatcct ttgatctttt ctacggggtc    4260
tgacgctcag tggaacgaaa actcacgtta agggattttg gtcatgagat tatcaaaaag    4320
gatcttcacc tagatccttt taaattaaaa atgaagtttt aaatcaatct aaagtatata    4380
tgagtaaact tggtctgaca gttaccaatg cttaatcagt gaggcaccta tctcagcgat    4440
ctgtctattt cgttcatcca tagttgcctg actccccgtc gtgtagataa ctacgatacg    4500
ggagggctta ccatctggcc ccagtgctgc aatgataccg cgagacccac gctcaccggc    4560
tccagattta tcagcaataa accagccagc cggaagggcc gagcgcagaa gtggtcctgc    4620
aactttatcc gcctccatcc agtctattaa ttgttgccgg gaagctagag taagtagttc    4680
gccagttaat agtttgcgca acgttgttgc cattgctaca ggcatcgtgg tgtcacgctc    4740
gtcgtttggt atggcttcat tcagctccgg ttcccaacga tcaaggcgag ttacatgatc    4800
ccccatgttg tgcaaaaaag cggttagctc cttcggtcct ccgatcgttg tcagaagtaa    4860
gttggccgca gtgttatcac tcatggttat ggcagcactg cataattctc ttactgtcat    4920
gccatccgta agatgctttt ctgtgactgg tgagtactca accaagtcat tctgagaata    4980
gtgtatgcgg cgaccgagtt gctcttgccc ggcgtcaata cggataataa ccgcgccaca    5040
tagcagaact ttaaaagtgc tcatcattgg aaaacgttct tcggggcgaa aactctcaag    5100
```

```
gatcttaccg ctgttgagat ccagttcgat gtaacccact cgtgcaccca actgatcttc    5160
agcatctttt actttcacca gcgtttctgg gtgagcaaaa acaggaaggc aaaatgccgc    5220
aaaaaaggga ataagggcga cacggaaatg ttgaatactc atactcttcc tttttcaata    5280
ttattgaagc atttatcagg gttattgtct catgagcgga tacatatttg aatgtattta    5340
gaaaaataaa caaatagggg ttccgcgcac atttccccga aaagtgccac ctgacgtcta    5400
agaaaccatt attatcatga cattaaccta taaaaatagg cgtatcacga ggccctttcg    5460
tctcgcgcgt ttcggtgatg acggtgaaaa cctctgacac atgcagctcc cggagacggt    5520
cacagcttgt ctgtaagcgg atgccgggag cagacaagcc cgtcagggcg cgtcagcggg    5580
tgttggcggg tgtcggggct ggcttaacta tgcggcatca gagcagattg tactgagagt    5640
gcaccatatg cggtgtgaaa taccgcacag atgcgtaagg agaaaatacc gcatcaggcg    5700
ccattcgcca ttcaggctgc gcaactgttg ggaagggcga tcggtgcggg cctcttcgct    5760
attacgccag ctggcgaaag ggggatgtgc tgcaaggcga ttaagttggg taacgccagg    5820
gttttcccag tcacgacgtt gtaaaacgac ggccagtgaa ttgacgcgta ttgggat      5877
```

```
<210> SEQ ID NO 32
<211> LENGTH: 5768
<212> TYPE: DNA
<213> ORGANISM: Artificial Sequence
<220> FEATURE:
<223> OTHER INFORMATION: pUC57-A36R-rKanI plasmid

<400> SEQUENCE: 32
```

```
ggatcctaac aaattttaaa caactaaaca gtacgacgga tgctgaagcg tgttatatat      60
acaagtctgg aaaactggtt aaaacagtat gtaaaagtac tcaatctgta ctatgtgtta     120
aaaaattcta caagtgacaa caaaaaatga attaataata agtcgttaac gtacgccgcc     180
atggacgccg cgtttgttat tactccaatg ggtgtgttga ctataacaga tacattgtat     240
gatgatctcg atatctcaat catggacttt ataggaccat acattatagg taacataaaa     300
actgtccaaa tagatgtacg ggatataaaa tattccgaca tgcaaaaatg ctactttagc     360
tataagggta aaatagttcc tcaggattct aatgatttgg ctagattcaa catttatagc     420
atttgtgccg catacagatc aaaaaatacc atcatcatag catgcgacta tgatatcatg     480
ttagatatag aagataaaca tcagccattt tatctattcc catctattga tgttttttaac     540 gctacaatca tagaagcgta taacctgtat acagctggag attatcatct aatcatcaat     600
ccttcagata atctgaaaat gaaattgtcg tttaattctt cattctgcat atcagacggc     660
aatggatgga tcataattga tgggaaatgc aatagtaatt ttttatcata aaagttgtaa     720
agtaaataat aaaacaataa atattgaact agtagtacgt atattgagca atcagaaatg     780
atgctggtac ctcttatcac ggtgaccgta gttgcgggaa caatattagt atgttatata     840
ttatatattt gtaggaaaaa gatacgtact gtctataatg acaataaaat tatcatgaca     900
aaattaaaaa agataaagag ttctaattcc agcaaatcta gtaaatcaac tgatagcgaa     960
tcagactggg aggatcactg tagtgctatg gaacaaaaca atgacgtaag tagggataac    1020
agggtaatcg atttattcaa caaagccacg ttgtgtctca aatctctga  tgttacattg    1080 cacaagataa aaatatatca tcatgaacaa taaaactgtc tgcttacata aacagtaata    1140 caagggggtgt tatgagccat attcaacggg aaacgtcttg ctcgaggccg cgattaaatt    1200
ccaacatgga tgctgattta tatgggtata aatgggctcg cgataatgtc gggcaatcag    1260
```

-continued

```
gtgcgacaat ctatcgattg tatgggaagc ccgatgcgcc agagttgttt ctgaaacatg    1320
gcaaaggtag cgttgccaat gatgttacag atgagatggt cagactaaac tggctgacgg    1380
aatttatgcc tcttccgacc atcaagcatt ttatccgtac tcctgatgat gcatggttac    1440
tcaccactgc gatccccggg aaaacagcat tccaggtatt agaagaatat cctgattcag    1500
gtgaaaatat tgttgatgcg ctggcagtgt tcctgcgccg gttgcattcg attcctgttt    1560
gtaattgtcc ttttaacagc gatcgcgtat ttcgtctcgc tcaggcgcaa tcacgaatga    1620
ataacggttt ggttgatgcg agtgattttg atgacgagcg taatggctgg cctgttgaac    1680
aagtctggaa agaaatgcat aagcttttgc cattctcacc ggattcagtc gtcactcatg    1740
gtgatttctc acttgataac cttatttttg acgaggggaa attaataggt tgtattgatg    1800
ttggacgagt cggaatcgca gaccgatacc aggatcttgc catcctatgg aactgcctcg    1860
gtgagttttc tccttcatta cagaaacggc tttttcaaaa atatggtatt gataatcctg    1920
atatgaataa attgcagttt catttgatgc tcgatgagtt tttctaatca gaattggtta    1980
attggttgta acactggcaa gactgggagg atcactgtag tgctatggaa caaaacaatg    2040
acgtagataa tatttctagg aatgagatat tggacgatga tagcttcgct ggtagtttaa    2100
tatgggataa cgaatccaat gttatggcgc ctagcacaga acacatttac gatagtgttg    2160
ctggaagcac gctgctaata aataatgatc gtaatgaaca gactatttat cagaacacta    2220
cagtagtaat taatgaaacg gagactgtta aagtacttaa tgaagatacc aaacagaatc    2280
ctaactattc atccaatcct ttcgtaaatt ataataaaac cagtatttgt agcaagtcaa    2340
atccgtttat tacagaactt aacaataaat ttagtgagaa taatccgttt agacgagcac    2400
atagcgatga ttatcttaat aagcaagaac aagatcatga acacgatgat atagaatcat    2460
cggtcgtatc attggtgtga ttagtttcct ttttataaaa ttgaagtaat atttagtatt    2520
attgctgccg tcacgttgta caaatggaga tattccctgt attcggcatt tctaaaatta    2580 gcaatttat tgctaataat gactgtagat attatataga tacagaacat caaaaaatta    2640
tatctgatga gatcaataga cagatggatg aaacggtact tcttaccaac atcttaagcg    2700
tagaagttgt aaatgacaat gagatgtacc atcttattcc tcatagatta tcgacgatta    2760
tactctgtat tagttctgtc ggaggatgtg ttatctctat agataatgac atcaatgaca    2820
aaaatattct aacatttccc attgatcatg ctgtaatcat atccccactg agtaaatgtg    2880
tcgtagttag caagggtcct acaaccatat tggttgttaa agcggatata cctagcaaac    2940
gattggtaac atcgtttaca aacgacatac tatatgtaaa caatctgtca ctgattaatt    3000
atttgccgtt gtctgtattc attattagac gagtcaccga ctatttggat agacgcatat    3060
gcgatcagat atttgctaat aatggatcca tcccaatggc gcgccgagct ggcgtaatc    3120 atggtcatag ctgtttcctg tgtgaaattg ttatccgctc acaattccac acaacatacg    3180
agccggaagc ataaagtgta aagcctgggg tgcctaatga gtgagctaac tcacattaat    3240
tgcgttgcgc tcactgcccg ctttccagtc gggaaacctg tcgtgccagc tgcattaatg    3300
aatcggccaa cgcgcgggga gaggcggttt gcgtattggg cgctcttccg cttcctcgct    3360
cactgactcg ctgcgctcgg tcgttcggct gcggcgagcg gtatcagctc actcaaaggc    3420
ggtaatacgg ttatccacag aatcagggga taacgcagga agaacatgt gagcaaaagg    3480 ccagcaaaag gccaggaacc gtaaaaaggc cgcgttgctg gcgtttttcc ataggctccg    3540
cccccctgac gagcatcaca aaaatcacaaa aatcgacgct caagtcagag gtggcgaaac    3600
ccgacaggac tataaagata ccaggcgttt cccccctggaa gctccctcgt gcgctctcct    3660
```

-continued

```
gttccgaccc tgccgcttac cggatacctg tccgcctttc tcccttcggg aagcgtggcg    3720
ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg gcctaactac    3960
ggctacacta gaagaacagt atttggtatc tgcgctctgc tgaagccagt taccttcgga    4020
aaaagagttg gtagctcttg atccggcaaa caaaccaccg ctggtagcgg tggtttttt    4080 gtttgcaagc agcagattac gcgcagaaaa aaaggatctc aagaagatcc tttgatcttt    4140
tctacggggt ctgacgctca gtggaacgaa aactcacgtt aagggatttt ggtcatgaga    4200
ttatcaaaaa ggatcttcac ctagatcctt ttaaattaaa aatgaagttt taaatcaatc    4260
taaagtatat atgagtaaac ttggtctgac agttaccaat gcttaatcag tgaggcacct    4320
atctcagcga tctgtctatt tcgttcatcc atagttgcct gactccccgt cgtgtagata    4380
actacgatac gggagggctt accatctggc cccagtgctg caatgatacc gcgagaccca    4440
cgctcaccgg ctccagattt atcagcaata aaccagccag ccggaagggc cgagcgcaga    4500
agtggtcctg caactttatc cgcctccatc cagtctatta attgttgccg ggaagctaga    4560
gtaagtagtt cgccagttaa tagtttgcgc aacgttgttg ccattgctac aggcatcgtg    4620
gtgtcacgct cgtcgtttgg tatggcttca ttcagctccg gttcccaacg atcaaggcga    4680
gttacatgat cccccatgtt gtgcaaaaaa gcggttagct ccttcggtcc tccgatcgtt    4740
gtcagaagta agttggccgc agtgttatca ctcatggtta tggcagcact gcataattct    4800
cttactgtca tgccatccgt aagatgcttt tctgtgactg gtgagtactc aaccaagtca    4860
ttctgagaat agtgtatgcg gcgaccgagt tgctcttgcc cggcgtcaat acgggataat    4920
accgcgccac atagcagaac tttaaaagtg ctcatcattg gaaaacgttc ttcggggcga    4980
aaactctcaa ggatcttacc gctgttgaga tccagttcga tgtaacccac tcgtgcaccc    5040
aactgatctt cagcatcttt tactttcacc agcgtttctg ggtgagcaaa aacaggaagg    5100
caaaatgccg caaaaaaggg aataagggcg acacggaaat gttgaatact catactcttc    5160 cttttcaat attattgaag catttatcag ggttattgtc tcatgagcgg atacatattt    5220
gaatgtattt agaaaaataa acaaataggg gttccgcgca catttccccg aaaagtgcca    5280
cctgacgtct aagaaaccat tattatcatg acattaacct ataaaaatag gcgtatcacg    5340
aggccctttc gtctcgcgcg tttcggtgat gacggtgaaa acctctgaca catgcagctc    5400
ccggagacgg tcacagcttg tctgtaagcg gatgccggga gcagacaagc ccgtcagggc    5460
gcgtcagcgg gtgttggcgg gtgtcggggc tggcttaact atgcggcatc agagcagatt    5520
gtactgagag tgcaccatat gcggtgtgaa ataccgcaca gatgcgtaag gagaaaatac    5580
cgcatcaggc gccattcgcc attcaggctg cgcaactgtt gggaagggcg atcggtgcgg    5640
gcctcttcgc tattacgcca gctggcgaaa gggggatgtg ctgcaaggcg attaagttgg    5700
gtaacgccag ggttttccca gtcacgacgt tgtaaaacga cggccagtga attgacgcgt    5760
attgggat                                                                5768
```

<210> SEQ ID NO 33
<211> LENGTH: 8361
<212> TYPE: DNA
<213> ORGANISM: Artificial Sequence
<220> FEATURE:

<223> OTHER INFORMATION: pUC57-A33-34-36R-rKanI plasmid

<400> SEQUENCE: 33

```
ggatccgatt tggttgtatt ggggaaggta acaattaatg atctaaagat gatgctattt        60
tacatggatt tatcatatca tggagtgaca agtagtggag caatttacaa attgggatcg       120
tctatcgata gactttctct aaataggact attgttacaa aagttaataa taattataat       180
tatgatgata catttttttga cgacgatgat tgatcgctat tgcacaattt tgttttttta       240
ctttctaata tagcgtttag attctttttc atgtgcgaat attgatttac taaaatatct       300
atgtttaact tttgttctat aacgtcctta tcggcggtat cggtacatat acgtaattca       360
ccttcacaaa atacggagtc ttcgataata atagccaatc gattattgga tctagctgtc       420
tgtatcatat tcaacatgtt taatatatcc tttcgtttcc cctttacagg catcgatcgt       480
agcatatttt ccgcgtctga tatggaaatg ttaaaactac aaaaatgcgt aatgttagcc       540
cgtcctaata ttggtacgtg tctataagtt tggcatagta gaataataga cgtgtttaaa       600
tgccttccga agtttaagaa ttctattaga gtattgcatt ttgatagttt atcacctaca       660
tcatcaaaaa taagtaaaaa gtgtgctgat tttttatgat tttgtgcgac agcaatacat       720
ttttctatgt tactttttagt tcgtatcaga ttatattcta gagattcctg actactaacg       780
aaattaatat gatttggcca aatgtatcca tcataatctg ggttataaac gggtgtaaac       840
aagaatatat gtttatattt tttaactagt gtagaaaaca gagatagtaa atagatagtt       900
tttccagatc cagatcctcc cgttaaaacc attctaaacg gcatttttaa taaattttct       960
cttgaaaatt gttttttcttg gaaacaattc ataattatat ttacagttac taaattaatt      1020
tgataataaa tcaaaatatg gaaaactaag gttgttagta gggaggagaa caaagaaggc      1080
acatcgtgat ataaataaca tttattatca tgatgacacc agaaaacgac gaagagcaga      1140
catctgtgtt ctccgctact gtttacggag acaaaattca gggaaagaat aaacgcaaac      1200
gcgtgattgg tctatgtatt agaatatcta tggttatttc actactatct atgattacca      1260
tgtccgcgtt tctcatagtg cgcctaaatc aatgcatgtc tgctaacgag gctgctatta      1320
ctgacgccgc tgttgccgtt gctgctgcat catctactca tagaaaggtt gcgtctagca      1380
ctacgcaata tgatcacaaa gaaagctgta atggtttata ttaccagggt tcttgttata      1440
tattacattc agactaccag ttattctcgg atgctaaagc aaattgcact gcggaatcat      1500
caacactacc caataaatcc gatgtcttga ttacctggct cattgattat gttgaggata      1560 catgggatc tgatggtaat ccaattacaa aaactacatc cgattatcaa gattctgata      1620
tatcacaaga agttagaaag tatttttgtg ttaaaacaat gaactaatat ttattttgt      1680 acattaataa atgaaatcgc ttaatagaca aactgtaagt aggtttaaga agttgtcggt      1740
gccggccgct ataatgatga tactctcaac cattattagt ggcataggaa catttctgca      1800
ttacaaagaa gaactgatgc ctagtgcttg cgccaatgga tggatacaat acgataaaca      1860
ttgttatcta gataccaaca ttaaaatgtc tacagataat gcggtttatc agtgtcgtaa      1920
attacgagct agattgccta gacctgatac tagacatctg agagtattgt ttagtatttt      1980
ttataaagat tattgggtaa gtttaaaaaa gaccaataat aaatggttag atattaataa      2040
tgataaagat atagatatta gtaaattaac aaattttaaa caactaaaca gtacgacgga      2100
tgctgaagcg tgttatatat acaagtctgg aaaactggtt gaacagtatg taaaagtact      2160
caatctgtac tatgtgttaa aaaattctac aagtgacaac aaaaaatgaa ttaataataa      2220
gtcgttaacg tacgccgcca tggacgccgc gtttgttatt actccaatgg gtgtgttgac      2280
```

-continued

```
tataacagat acattgtatg atgatctcga tatctcaatc atggactta taggaccata    2340 cattataggt aacataaaaa ctgtccaaat agatgtacgg gatataaaat attccgacat    2400
gcaaaaatgc tactttagct ataagggtaa aatagttcct caggattcta atgatttggc    2460
tagattcaac atttatagca tttgtgccgc atacagatca aaaaatacca tcatcatagc    2520
atgcgactat gatatcatgt tagatataga agataaacat cagccatttt atctattccc    2580
atctattgat gttttaacg ctacaatcat agaagcgtat aacctgtata cagctggaga    2640
ttatcataag tagggataac agggtaatcg atttattcaa caaagccacg ttgtgtctca    2700
aaatctctga tgttacattg cacaagataa aaatatatca tcatgaacaa taaaactgtc    2760
tgcttacata aacagtaata caagggggtgt tatgagccat attcaacggg aaacgtcttg    2820
ctcgaggccg cgattaaatt ccaacatgga tgctgattta tatgggtata aatgggctcg    2880
cgataatgtc gggcaatcag gtgcgacaat ctatcgattg tatgggaagc ccgatgcgcc    2940
agagttgttt ctgaaacatg gcaaaggtag cgttgccaat gatgttacag atgagatggt    3000
cagactaaac tggctgacgg aatttatgcc tcttccgacc atcaagcatt ttatccgtac    3060
tcctgatgat gcatggttac tcaccactgc gatccccggg aaaacagcat tccaggtatt    3120
agaagaatat cctgattcag gtgaaaatat tgttgatgcg ctggcagtgt tcctgcgccg    3180
gttgcattcg attcctgttt gtaattgtcc ttttaacagc gatcgcgtat ttcgtctcgc    3240
tcaggcgcaa tcacgaatga ataacggttt ggttgatgcg agtgattttg atgacgagcg    3300
taatggctgg cctgttgaac aagtctggaa agaaatgcat aagcttttgc cattctcacc    3360
ggattcagtc gtcactcatg gtgatttctc acttgataac cttattttg acgaggggaa    3420 attaataggt tgtattgatg ttggacgagt cggaatcgca gaccgatacc aggatcttgc    3480
catcctatgg aactgcctcg gtgagttttc tccttcatta cagaaacggc ttttttcaaaa    3540 atatggtatt gataatcctg atatgaataa attgcagttt catttgatgc tcgatgagtt    3600
tttctaatca gaattggtta attggttgta acactggcaa caatcataga agcgtataac    3660
ctgtatacag ctggagatta tcatctaatc atcaatcctt cagataatct gaaaatgaaa    3720
ttgtcgttta attcttcatt ctgcatatca gacggcaatg gatggatcat aattgatggg    3780
aaatgcaata gtaatttttt atcataaaag ttgtaaagta aataataaaa caataaatat    3840
tgaactagta gtacgtatat tgagcaatca gaaatgatgc tggtacctct tatcacggtg    3900
accgtagttg cgggaacaat attagtatgt tatatattat atatttgtag gaaaaagata    3960
cgtactgtct ataatgacaa taaaattatc atgacaaaat taaaaaagat aaagagttct    4020
aattccagca aatctagtaa atcaactgat agcgaatcag actgggagga tcactgtagt    4080
gctatggaac aaaacaatga cgtagataat atttctagga atgagatatt ggacgatgat    4140
agcttcgctg gtagtttaat atgggataac gaatccaatg ttatggcgcc tagcacagaa    4200
cacatttacg atagtgttgc tggaagcacg ctgctaataa ataatgatcg taatgaacag    4260
actatttatc agaacactac agtagtaatt aatgaaacgg agactgttaa agtacttaat    4320
gaagatacca aacagaatcc taactattca tccaatcctt tcgtaaatta taataaaacc    4380
agtatttgta gcaagtcaaa tccgtttatt acagaactta acaataaatt tagtgagaat    4440 aatccgtta gacgagcaca tagcgatgat tatcttaata agcaagaaca agatcatgaa    4500
cacgatgata tagaatcatc ggtcgtatca ttggtgtgat tagtttcctt tttataaaat    4560
tgaagtaata tttagtatta ttgctgccgt cacgttgtac aaatggagat attccctgta    4620
```

-continued

```
ttcggcattt ctaaaattag caatttatt gctaataatg actgtagata ttatatagat    4680
acagaacatc aaaaaattat atctgatgag atcaatagac agatggatga aacggtactt    4740
cttaccaaca tcttaagcgt agaagttgta aatgacaatg agatgtacca tcttattcct    4800
catagattat cgacgattat actctgtatt agttctgtcg gaggatgtgt tatctctata    4860
gataatgaca tcaatgacaa aaatattcta acatttccca ttgatcatgc tgtaatcata    4920
tccccactga gtaaatgtgt cgtagttagc aagggtccta caaccatatt ggttgttaaa    4980
gcggatatac ctagcaaacg attggtaaca tcgtttacaa acgacatact atatgtaaac    5040
aatctgtcac tgattaatta tttgccgttg tctgtattca ttattagacg agtcaccgac    5100
tatttggata gacgcatatg cgatcagata tttgctaata ataagtggta ttccattata    5160
accatcgacg ataagcaata tcctattcca tcaaactgta taggtatgtc ctctgccaag    5220
tacataaatt ctagcatcga gcaagatact ttaatccatg tttgtaacct cgagcatccg    5280
ttcgactcag tatacaaaaa aatgcagtcg tacaattctc tacctatcaa ggaacaaata    5340
ttgtacggta gaattgataa tataaatatg agcattagta tttctgtgga ttaatagatt    5400
tctagtatgg ggatcattaa tcatctctaa tctctaaata cctcataaaa cgaaaaaaaa    5460
gctattatca aatactgtac ggaatggatt cattctcttc tctttttatg aaactctgtt    5520
gtatatctac tgataaaact ggaagcaaaa aatctgataa aaagaataag aataagatca    5580
aggattatat ggaacacgat tattataaaa taacaatagt tcctggttcc tcttccacgt    5640
ctactagctc gtggtattat acacatgcct agtaatggat ccatcccaat ggcgcgccga    5700
gcttggcgta atcatggtca tagctgtttc ctgtgtgaaa ttgttatccg ctcacaattc    5760
cacacaacat acgagccgga agcataaagt gtaaagcctg gggtgcctaa tgagtgagct    5820
aactcacatt aattgcgttg cgctcactgc ccgctttcca gtcgggaaac ctgtcgtgcc    5880
agctgcatta atgaatcggc caacgcgcgg ggagaggcgg tttgcgtatt gggcgctctt    5940
ccgcttcctc gctcactgac tcgctgcgct cggtcgttcg gctgcggcga gcggtatcag    6000
ctcactcaaa ggcggtaata cggttatcca cagaatcagg ggataacgca ggaaagaaca    6060
tgtgagcaaa aggccagcaa aaggccagga accgtaaaaa ggccgcgttg ctggcgtttt    6120
tccataggct ccgcccccct gacgagcatc acaaaatcac aaaaatcgac gctcaagtca    6180
gaggtggcga aacccgacag gactataaag ataccaggcg tttccccctg gaagctccct    6240
cgtgcgctct cctgttccga ccctgccgct taccggatac ctgtccgcct ttctcccttc    6300
gggaagcgtg cgctttctc atagctcacg ctgtaggtat ctcagttcgg tgtaggtcgt    6360
tcgctccaag ctgggctgtg tgcacgaacc ccccgttcag cccgaccgct gcgccttatc    6420
cggtaactat cgtcttgagt ccaacccggt aagacacgac ttatcgccac tggcagcagc    6480
cactggtaac aggattagca gagcgaggta tgtaggcggt gctacagagt tcttgaagtg    6540
gtggcctaac tacggctaca ctagaagaac agtatttggt atctgcgctc tgctgaagcc    6600
agttaccttc ggaaaaagag ttggtagctc ttgatccggc aaacaaacca ccgctggtag    6660
cggtggtttt tttgtttgca agcagcagat tacgcgcaga aaaaaggat ctcaagaaga    6720 tcctttgatc ttttctacgg ggtctgacgc tcagtggaac gaaaactcac gttaagggat    6780
tttggtcatg agattatcaa aaaggatctt cacctagatc cttttaaatt aaaaatgaag    6840
ttttaaatca atctaaagta tatatgagta aacttggtct gacagttacc aatgcttaat    6900
cagtgaggca cctatctcag cgatctgtct atttcgttca tccatagttg cctgactccc    6960
cgtcgtgtag ataactacga tacgggaggg cttaccatct ggccccagtg ctgcaatgat    7020
```

```
accgcgagac ccacgctcac cggctccaga tttatcagca ataaaccagc cagccggaag    7080
ggccgagcgc agaagtggtc ctgcaacttt atccgcctcc atccagtcta ttaattgttg    7140
ccgggaagct agagtaagta gttcgccagt taatagtttg cgcaacgttg ttgccattgc    7200
tacaggcatc gtggtgtcac gctcgtcgtt tggtatggct tcattcagct ccggttccca    7260
acgatcaagg cgagttacat gatcccccat gttgtgcaaa aaagcggtta gctccttcgg    7320
tcctccgatc gttgtcagaa gtaagttggc cgcagtgtta tcactcatgg ttatggcagc    7380
actgcataat tctcttactg tcatgccatc cgtaagatgc ttttctgtga ctggtgagta    7440
ctcaaccaag tcattctgag aatagtgtat gcggcgaccg agttgctctt gcccggcgtc    7500
aatacgggat aataccgcgc cacatagcag aactttaaaa gtgctcatca ttggaaaacg    7560
ttcttcgggg cgaaaactct caaggatctt accgctgttg agatccagtt cgatgtaacc    7620
cactcgtgca cccaactgat cttcagcatc ttttactttc accagcgttt ctgggtgagc    7680
aaaaacagga aggcaaaatg ccgcaaaaaa gggaataagg gcgacacgga aatgttgaat    7740
actcatactc ttcctttttc aatattattg aagcatttat cagggttatt gtctcatgag    7800
cggatacata tttgaatgta tttagaaaaa taaacaaata ggggttccgc gcacatttcc    7860
ccgaaaagtg ccacctgacg tctaagaaac cattattatc atgacattaa cctataaaaa    7920
taggcgtatc acgaggccct ttcgtctcgc gcgtttcggt gatgacggtg aaaacctctg    7980
acacatgcag ctcccggaga cggtcacagc ttgtctgtaa gcggatgccg ggagcagaca    8040
agcccgtcag ggcgcgtcag cgggtgttgg cgggtgtcgg ggctggctta actatgcggc    8100
atcagagcag attgtactga gagtgcacca tatgcggtgt gaaataccgc acagatgcgt    8160
aaggagaaaa taccgcatca ggcgccattc gccattcagg ctgcgcaact gttgggaagg    8220
gcgatcggtg cgggcctctt cgctattacg ccagctggcg aaagggggat gtgctgcaag    8280
gcgattaagt tgggtaacgc cagggttttc ccagtcacga cgttgtaaaa cgacggccag    8340
tgaattgacg cgtattggga t                                              8361
```

```
<210> SEQ ID NO 34
<211> LENGTH: 6563
<212> TYPE: DNA
<213> ORGANISM: Artificial Sequence
<220> FEATURE:
<223> OTHER INFORMATION: pUC57-A56R-rKanI plasmid

<400> SEQUENCE: 34
ggatcctgat atcttcacgt agatataggt gtagtttcgc agtggccgtc ctggataata      60
ttatttatat gatgggtgga tatgatcagt ccccgtatag aagttcaaag gttatagcgt     120
acaatacatg tacaaattct tggatatatg atataccaga gctaaaatat cctcgttcta     180
attgtggggg actggctgat gacgaataca tttattgtat aggcggcata cgcgatcagg     240
attcatcgtt gacatctagt attgatagat ggaagccatc aaaaccatat ggcagaagt     300 atgctaaaat gcgcgaacca aaatgtgata tggggttgc gatgttaaac ggattaatat     360
atgtcatggg tggaatcgtt aaaggtgaca cgtgtaccga cgcactagag agtttatcag     420 aagatggat gatgaagcat caacgtcttc aataaaaat gtccaatatg tcgacgattg     480
ttcatgatgg caagatttat atatctggag gttacaacaa tagtagtgta gttaatgtaa     540
tatcgaatct agtccttagc tataattcga tatatgatga atggaccaaa ttatcatcat     600
taaacattcc tagaattaat cccgctctat ggtcagcgca taataaatta tatgtaggag     660
```

-continued

```
gaggaatatc tgatgatgtt cgaactaata catctgagac atacgacaaa gaaaaagatt       720
gttggacatt ggataatggt cacgtgttac cacgcaatta tataatgtat aaatgcgaac       780
cgattaaaca taaatatcca ttggaaaaaa cacagtacac gaatgatttt ctaaagtatt       840
tggaaagttt tataggtagt tgatagaaca aaatacataa ttttgtaaaa ataaatcact       900
ttttatacta atatgacacg attaccaata cttttgttac taatatcatt agtatacgct       960
acaccttttc ctcagacatc taaaaaaata ggtgatgatg caactctatc atgtaatcga      1020
aataatacaa atgactacgt tgttatgagt gcttggtata aggagcccaa ttccattatt      1080
cttttagctg ctaaaagcga cgtcttgtat tttgataatt ataccaagga taaaatatct      1140
tacgactctc catacgatga tctagttaca actatcacaa ttaaatcatt gactgctaga      1200
gatgccggta cttatgtatg tgcattcttt atgacatcga ctacaaatga cactgataaa      1260
gtagattatg aagaatactc cacagagttg attgtaaata cagatagtga atcgactata      1320
gacataatac tatctggatc tacacattca ccggaaacta gttctgagaa acctgaggat      1380
atagataatt ttaattgctc gtcggtattc gaaatcgcga ctccggaacc aattactgat      1440
aatgtagaag atcatacaga caccgtcaca tacactagtg atagcattaa tacagtaagt      1500
gcatcataag tagggataac agggtaatcg atttattcaa caaagccacg ttgtgtctca      1560
aaatctctga tgttacattg cacaagataa aaatatatca tcatgaacaa taaaactgtc      1620
tgcttacata aacagtaata caagggggtgt tatgagccat attcaacggg aaacgtcttg      1680
ctcgaggccg cgattaaatt ccaacatgga tgctgattta tatgggtata aatgggctcg      1740
cgataatgtc gggcaatcag gtgcgacaat ctatcgattg tatgggaagc ccgatgcgcc      1800
agagttgttt ctgaaacatg gcaaaggtag cgttgccaat gatgttacag atgagatggt      1860
cagactaaac tggctgacgg aatttatgcc tcttccgacc atcaagcatt ttatccgtac      1920
tcctgatgat gcatggttac tcaccactgc gatccccggg aaaacagcat tccaggtatt      1980
agaagaatat cctgattcag gtgaaaatat tgttgatgcg ctggcagtgt tcctgcgccg      2040
gttgcattcg attcctgttt gtaattgtcc ttttaacagc gatcgcgtat ttcgtctcgc      2100
tcaggcgcaa tcacgaatga ataacggttt ggttgatgcg agtgattttg atgacgagcg      2160
taatggctgg cctgttgaac aagtctggaa agaaatgcat aagcttttgc cattctcacc      2220
ggattcagtc gtcactcatg gtgatttctc acttgataac cttattttg acgaggggaa      2280 attaataggt tgtattgatg ttggacgagt cggaatcgca gaccgatacc aggatcttgc      2340
catcctatgg aactgcctcg gtgagttttc tccttcatta cagaaacggc ttttttcaaaa     2400 atatggtatt gataatcctg atatgaataa attgcagttt catttgatgc tcgatgagtt      2460
tttctaatca gaattggtta attggttgta acactggcac cgtcacatac actagtgata      2520
gcattaatac agtaagtgca tcatctggag aatccacaac agacgagact ccggaaccaa      2580
ttactgataa agaagaagat catacagtca cagacactgt ctcatacact acagtaagta      2640
catcatctgg aattgtcact actaaatcaa ccaccgatga tgcggatctt tatgatacgt      2700
acaatgataa tgatacagta ccaccaacta ctgtaggcgg tagtacaacc tctattagca      2760
attataaaac caaggacttt gtagaaatat ttggtattac cgcattaatt atattgtcgg      2820
ccgtggcaat attctgtatt acgtattata tatataataa acgttcacgt aaatacaaaa      2880
cagagaacaa agtctagatt tttgacttac ataaatgtct gggatagtaa aatctatcat      2940
attgagcgga ccatctggtt taggaaagac agccatagcc aaaagactat gggaatatat      3000
ttggatttgt ggtgtcccat accactagat ttcctcgtcc tatggaacga gaaggtgtcg      3060
```

-continued

```
attaccatta cgttaacaga gaggccatct ggaagggaat agccgccgga aactttctag    3120
aacatactga gttttaggga aatatttacg gaacttctaa aactgctgtg aatacagcgg    3180
ctattaataa tcgtatttgt gtgatggatc taaacatcga tggcgttaga agtcttaaaa    3240
atacgtacct aatgccttac tcggtgtata taagacctac ctctcttaaa atggttgaga    3300
ccaagcttcg tcgtagaaac actgaagcgg atgatgagat tcatcgtcgt gtgatgttgg    3360
caaaaactga catggatgag gcaggtgaag ccggtctatt cgacactatt attattgaag    3420
atgatgtgaa tttagcatat agtaagttaa ttcagatact acaggaccgt attagaatgt    3480
attttaacac taattagaga cttaagactt aaaacttgat aattaataat ataactcgtt    3540
tttatatgtg tctatttcaa cgtctaatgt attagttaaa tattaaaact taccacgtaa    3600
aacttaaaat ttaaaatgat atttcattga cagatagatc acacattatg aactttcaag    3660
gacttgtgtt aactgacaat tgcaaaaatc aatgggtcgt tggaccatta ataggaaaag    3720
gtggattcgg tagtatttat actactaatg acaataatta tgtagtaaaa atagagccca    3780
aagctaacgg atcattattt accgaacagg cattttatac tagagtactt aaaccatccg    3840
ttatcgaaga atggaaaaaa tctcacaata taaagcacgg atccatccca atggcgcgcc    3900
gagcttggcg taatcatggt catagctgtt tcctgtgtga aattgttatc cgctcacaat    3960
tccacacaac atacgagccg gaagcataaa gtgtaaagcc tggggtgcct aatgagtgag    4020
ctaactcaca ttaattgcgt tgcgctcact gcccgctttc cagtcgggaa acctgtcgtg    4080
ccagctgcat taatgaatcg gccaacgcgc ggggagaggc ggtttgcgta ttgggcgctc    4140
ttccgcttcc tcgctcactg actcgctgcg ctcggtcgtt cggctgcggc gagcggtatc    4200
agctcactca aaggcggtaa tacggttatc cacagaatca ggggataacg caggaaagaa    4260
catgtgagca aaaggccagc aaaaggccag gaaccgtaaa aaggccgcgt tgctggcgtt    4320
tttccatagg ctccgccccc ctgacgagca tcacaaaatc acaaaaatcg acgctcaagt    4380
cagaggtggc gaaacccgac aggactataa agataccagg cgtttccccc tggaagctcc    4440
ctcgtgcgct ctcctgttcc gaccctgccg cttaccggat acctgtccgc ctttctccct    4500
tcgggaagcg tggcgctttc tcatagctca cgctgtaggt atctcagttc ggtgtaggtc    4560
gttcgctcca agctgggctg tgtgcacgaa ccccccgttc agcccgaccg ctgcgcctta    4620
tccggtaact atcgtcttga gtccaacccg gtaagacacg acttatcgcc actggcagca    4680
gccactggta acaggattag cagagcgagg tatgtaggcg gtgctacaga gttcttgaag    4740
tggtggccta actacggcta cactagaaga acagtatttg gtatctgcgc tctgctgaag    4800
ccagttacct tcggaaaaag agttggtagc tcttgatccg gcaaacaaac caccgctggt    4860
agcggtggtt tttttgtttg caagcagcag attacgcgca gaaaaaaagg atctcaagaa    4920
gatcctttga tcttttctac ggggtctgac gctcagtgga acgaaaactc acgttaaggg    4980
attttggtca tgagattatc aaaaaggatc ttcacctaga tccttttaaa ttaaaaatga    5040
agttttaaat caatctaaag tatatatgag taaacttggt ctgacagtta ccaatgctta    5100
atcagtgagg cacctatctc agcgatctgt ctatttcgtt catccatagt tgcctgactc    5160
cccgtcgtgt agataactac gatacgggag ggcttaccat ctggccccag tgctgcaatg    5220
ataccgcgag acccacgctc accggctcca gatttatcag caataaacca gccagccgga    5280
agggccgagc gcagaagtgg tcctgcaact ttatccgcct ccatccagtc tattaattgt    5340
tgccgggaag ctagagtaag tagttcgcca gttaatagtt tgcgcaacgt tgttgccatt    5400
```

-continued

```
gctacaggca tcgtggtgtc acgctcgtcg tttggtatgg cttcattcag ctccggttcc    5460
caacgatcaa ggcgagttac atgatccccc atgttgtgca aaaaagcggt tagctccttc    5520
ggtcctccga tcgttgtcag aagtaagttg gccgcagtgt tatcactcat ggttatggca    5580
gcactgcata attctcttac tgtcatgcca tccgtaagat gctttctgt gactggtgag      5640 tactcaacca agtcattctg agaatagtgt atgcggcgac cgagttgctc ttgcccggcg    5700
tcaatacggg ataataccgc gccacatagc agaactttaa aagtgctcat cattggaaaa    5760
cgttcttcgg ggcgaaaact ctcaaggatc ttaccgctgt tgagatccag ttcgatgtaa    5820
cccactcgtg cacccaactg atcttcagca tctttactt tcaccagcgt ttctgggtga      5880
gcaaaaacag gaaggcaaaa tgccgcaaaa aagggaataa gggcgacacg gaaatgttga    5940
atactcatac tcttcctttt tcaatattat tgaagcattt atcagggtta ttgtctcatg    6000
agcggataca tatttgaatg tatttagaaa aataaacaaa taggggttcc gcgcacattt    6060
ccccgaaaag tgccacctga cgtctaagaa accattatta tcatgacatt aacctataaa    6120
aataggcgta tcacgaggcc ctttcgtctc gcgcgtttcg gtgatgacgg tgaaaacctc    6180
tgacacatgc agctcccgga cacggtcaca gcttgtctgt aagcggatgc cgggagcaga    6240
caagcccgtc agggcgcgtc agcgggtgtt ggcgggtgtc ggggctggct taactatgcg    6300
gcatcagagc agattgtact gagagtgcac catatgcggt gtgaaatacc gcacagatgc    6360
gtaaggagaa aataccgcat caggcgccat tcgccattca ggctgcgcaa ctgttgggaa    6420
gggcgatcgg tgcgggcctc ttcgctatta cgccagctgg cgaagggggg atgtgctgca    6480
aggcgattaa gttgggtaac gccagggttt tcccagtcac gacgttgtaa aacgacggcc    6540
agtgaattga cgcgtattgg gat                                            6563
```

<210> SEQ ID NO 35
<211> LENGTH: 6188
<212> TYPE: DNA
<213> ORGANISM: Artificial Sequence
<220> FEATURE:
<223> OTHER INFORMATION: pUC57-B5R-rKanI plasmid

<400> SEQUENCE: 35

```
tctagaatat taactatcgt actatataca acgaaacatc tatttacgac gctgtcagtt      60
ataatgcgta taatacgttg gtctatctat taaacaaaaa tggtgatttt gagacgatta     120
ctactagtgg atgtacatgt atttcggaag cagtcgcaaa caacaacaaa ataataatgg     180
aagtactatt gtctaaacga ccatctttga aaattatgat acagtctatg atagcaatta     240
ctaaacataa acagcataat gcagatttat tgaaaatgtg tataaaatat actgcgtgta     300
tgaccgatta tgatactctt atagatgtac agtcgctaca gcaatataaa tggtatattt     360
taagatgttt cgatgaaata gatatcatga agagatgtta tataaaaaat aaaactgtat     420
tccaattagt tttttgtatc aaagacatta atactttaat gagatacggt aaacatcctt     480
ctttcgtgaa gtgcactagt ctcgacgtat acggaagtcg tgtacgtaat atcatagcat     540
ctattagata tcgtcagaga ttaattagtc tattatccaa gaagctggat gcgggagata     600
aatggtcgtt tttcctaac gaaataaaat ataaaatatt ggaaaacttt aacgataacg     660
aactatccac atatctaaaa atcttataaa cattattaaa atataaaatc taagtggata     720
aaatcacact acatcattgt ttcctttag tgctcgacag tgtatactat ttttaacgct      780
cataaataaa aatgaaaacg atttccgttg ttacgttgtt atgcgtacta cctgctgttg     840
tttattcaac atgtactgta cccactatga ataacgctaa attaacgtct accgaaacat     900
```

-continued

```
cgtttaatga taaacagaaa gttacattta catgtgatca gggatatcat tctttggatc      960
caaatgctgt ctgtgaaaca gataaatgga aatacgaaaa tccatgcaag aaaatgtgca     1020
cagtttctga ttatgtctct gaattatatg ataagccatt atacgaagtg aattccacca     1080
tgacactaag ttgcaacggc gaaacaaaat attttcgttg cgaagaaaaa aatggaaata     1140
cttcttggaa tgatactgtt acgtgtccta atgcggaatg tcaacctctt caattagaac     1200
acggatcgtg tcaaccagtt aaagaaaaat actcatttgg ggaatatatg actatcaact     1260
gtgatgttgg atatgaggtt attggtgctt cgtacataag ttgtacagct aattcttgga     1320
atgttattcc atcatgtcaa caaaaatgtg atataccgtc tctatctaac ggattaattt     1380
ccggatctac attttctatc ggtggcgtta tacatcttag ttgtaaaagt ggtttttatac    1440 taacggggtc tccatcatcc acatgtatcg acggtaaatg gaatcccata ctcccaacat     1500
gtgtactaag tagggataac agggtaatcg atttattcaa caaagccacg ttgtgtctca     1560
aaatctctga tgttacattg cacaagataa aaatatatca tcatgaacaa taaaactgtc     1620
tgcttacata aacagtaata caaggggtgt tatgagccat attcaacggg aaacgtcttg     1680
ctcgaggccg cgattaaatt ccaacatgga tgctgattta tatgggtata aatgggctcg     1740
cgataatgtc gggcaatcag gtgcgacaat ctatcgattg tatgggaagc ccgatgcgcc     1800
agagttgttt ctgaaacatg gcaaaggtag cgttgccaat gatgttacag atgagatggt     1860
cagactaaac tggctgacgg aatttatgcc tcttccgacc atcaagcatt ttatccgtac     1920
tcctgatgat gcatggttac tcaccactgc gatccccggg aaaacagcat tccaggtatt     1980
agaagaatat cctgattcag gtgaaaatat tgttgatgcg ctggcagtgt tcctgcgccg     2040
gttgcattcg attcctgttt gtaattgtcc ttttaacagc gatcgcgtat ttcgtctcgc     2100
tcaggcgcaa tcacgaatga ataacggttt ggttgatgcg agtgattttg atgacgagcg     2160
taatggctgg cctgttgaac aagtctggaa agaaatgcat aagcttttgc cattctcacc     2220
ggattcagtc gtcactcatg gtgatttctc acttgataac cttattttg acgaggggaa      2280 attaataggt tgtattgatg ttggacgagt cggaatcgca gaccgatacc aggatcttgc     2340
catcctatgg aactgcctcg gtgagttttc tccttcatta cagaaacggc tttttcaaaa     2400
atatggtatt gataatcctg atatgaataa attgcagttt catttgatgc tcgatgagtt     2460
tttctaatca gaattggtta attggttgta acactggcaa tgtatcgacg gtaaatggaa     2520
tcccatactc ccaacatgtg tacgatctaa cgaaaaattt gatccagtgg atgatggtcc     2580
cgacgatgag acagatttga gcaaactctc gaaagacgtt gtacaatatg aacaagaaat     2640
agaatcgtta gaagcaactt atcatataat catagtggcg ttaacaatta tgggcgtcat     2700 attttaatc tccgttatag tattagtttg ttcctgtgac aaaaataatg accaatataa      2760
gttccataaa ttgctaccgt aaatataaat ccgttaaaat aattaataat taataacgaa     2820
caagtatcaa aagattaaag acttatagct agaatcaatt gagatgtctt cttcagtgga     2880
tgttgatatc tacgatgccg ttagagcatt tttactcagg cactattata acaagagatt     2940
tattgtgtat ggaagaagta acgccatatt acataatata tacaggctat ttacaagatg     3000
cgccgttata ccgttcgatg atatagtacg tactatgcca aatgaatcac gtgttaaaca     3060
atgggtgatg gatacactta atggtataat gatgaatgaa cgcgatgttt ctgtaagcgt     3120
tggcaccgga atactattca tggaaatgtt tttcgattac aataaaaata gtatcaacaa     3180
tcaactaatg tatgatataa ttaatagcgt atctataatt ctagctaatg agagatatag     3240
```

-continued

```
aagcgctttt aacgacgatg gtatatacat ccgtagaaat atgattaaca agttgtacgg    3300
atacgcatct ctaactacta ttggcacgat cgctggaggt gtttgttatt atctgttgat    3360
gcatctagtt agtttgtata aataattatt tcaatatact agttaaaatt ttaagatttt    3420
aaatgtataa aaaactaata acgtttttat ttgtaatagg tgcattagca tcctattcga    3480
ataatgagta cactccgttt aattctagaa tcccaatggc gcgccgagct tggcgtaatc    3540
atggtcatag ctgtttcctg tgtgaaattg ttatccgctc acaattccac acaacatacg    3600
agccggaagc ataaagtgta aagcctgggg tgcctaatga gtgagctaac tcacattaat    3660
tgcgttgcgc tcactgcccg ctttccagtc gggaaacctg tcgtgccagc tgcattaatg    3720
aatcggccaa cgcgcgggga gaggcggttt gcgtattggg cgctcttccg cttcctcgct    3780
cactgactcg ctgcgctcgg tcgttcggct gcggcgagcg gtatcagctc actcaaaggc    3840
ggtaatacgg ttatccacag aatcagggga taacgcagga aagaacatgt gagcaaaagg    3900
ccagcaaaag gccaggaacc gtaaaaaggc cgcgttgctg gcgtttttcc ataggctccg    3960
cccccctgac gagcatcaca aaatcacaaa aatcgacgct caagtcagag gtggcgaaac    4020
ccgacaggac tataaagata ccaggcgttt cccccctggaa gctccctcgt gcgctctcct    4080
gttccgaccc tgccgcttac cggatacctg tccgcctttc tcccttcggg aagcgtggcg    4140
ctttctcata gctcacgctg taggtatctc agttcggtgt aggtcgttcg ctccaagctg    4200
ggctgtgtgc acgaacccccc cgttcagccc gaccgctgcg ccttatccgg taactatcgt    4260
cttgagtcca acccggtaag acacgactta tcgccactgg cagcagccac tggtaacagg    4320
attagcagag cgaggtatgt aggcggtgct acagagttct tgaagtggtg gcctaactac    4380
ggctacacta agaacagt atttggtatc tgcgctctgc tgaagccagt taccttcgga    4440
aaaagagttg gtagctcttg atccggcaaa caaaccaccg ctggtagcgg tggtttttt    4500 gtttgcaagc agcagattac gcgcagaaaa aaaggatctc aagaagatcc tttgatcttt    4560
tctacggggt ctgacgctca gtggaacgaa aactcacgtt aagggatttt ggtcatgaga    4620
ttatcaaaaa ggatcttcac ctagatcctt ttaaattaaa aatgaagttt taaatcaatc    4680
taaagtatat atgagtaaac ttggtctgac agttaccaat gcttaatcag tgaggcacct    4740
atctcagcga tctgtctatt tcgttcatcc atagttgcct gactccccgt cgtgtagata    4800
actacgatac gggagggctt accatctggc cccagtgctg caatgatacc gcgagaccca    4860
cgctcaccgg ctccagattt atcagcaata aaccagccag ccggaagggc cgagcgcaga    4920
agtggtcctg caactttatc cgcctccatc cagtctatta attgttgccg ggaagctaga    4980
gtaagtagtt cgccagttaa tagtttgcgc aacgttgttg ccattgctac aggcatcgtg    5040
gtgtcacgct cgtcgtttgg tatggcttca ttcagctccg gttcccaacg atcaaggcga    5100
gttacatgat cccccatgtt gtgcaaaaaa gcggttagct ccttcggtcc tccgatcgtt    5160
gtcagaagta agttggccgc agtgttatca ctcatggtta tggcagcact gcataattct    5220
cttactgtca tgccatccgt aagatgcttt tctgtgactg gtgagtactc aaccaagtca    5280
ttctgagaat agtgtatgcg cgaccgagt tgctcttgcc cggcgtcaat acgggataat    5340
accgcgccac atagcagaac tttaaaagtg ctcatcattg gaaaacgttc ttcggggcga    5400
aaactctcaa ggatcttacc gctgttgaga tccagttcga tgtaacccac tcgtgcaccc    5460
aactgatctt cagcatcttt tactttcacc agcgtttctg ggtgagcaaa aacaggaagg    5520
caaaatgccg caaaaaaggg aataagggcg acacggaaat gttgaatact catactcttc    5580
ctttttcaat attattgaag catttatcag ggttattgtc tcatgagcgg atacatattt    5640
```

```
gaatgtattt agaaaaataa acaaataggg gttccgcgca catttccccg aaaagtgcca    5700
cctgacgtct aagaaaccat tattatcatg acattaacct ataaaaatag gcgtatcacg    5760 aggcccttttc gtctcgcgcg tttcggtgat gacggtgaaa acctctgaca catgcagctc    5820
ccggagacgg tcacagcttg tctgtaagcg gatgccggga gcagacaagc ccgtcagggc    5880
gcgtcagcgg gtgttggcgg gtgtcggggc tggcttaact atgcggcatc agagcagatt    5940
gtactgagag tgcaccatat gcggtgtgaa ataccgcaca gatgcgtaag gagaaaatac    6000
cgcatcaggc gccattcgcc attcaggctg cgcaactgtt gggaagggcg atcggtgcgg    6060
gcctcttcgc tattacgcca gctggcgaaa gggggatgtg ctgcaaggcg attaagttgg    6120
gtaacgccag ggttttccca gtcacgacgt tgtaaaacga cggccagtga attgacgcgt    6180
attgggat                                                             6188
```

<210> SEQ ID NO 36
<211> LENGTH: 6200
<212> TYPE: DNA
<213> ORGANISM: Artificial Sequence
<220> FEATURE:
<223> OTHER INFORMATION: pUC57-F12-13L-rKanI plasmid

<400> SEQUENCE: 36

```
ggatccagac aaacaattaa ctattttgtc tctgttttta acacctccac agtttttaat     60
ttctttagta atgaaattat tcacaatatc agtatcttct ttatctacca gagattttac    120
taacttgata accttggctg tctcattcaa tagggtagta atatttgtat gtgtgatatt    180
gatatctttt tgaattgttt cttttagaag tgattctttg atggtgccag catacgaatt    240
acaataatgc agaaactcgg ttaacatgca ggaattatag taagccaatt ccaattgttg    300
cctgtgttgt attagagtgt caatatgagc aatggtgtcc ttgcgtttct ctgatagaat    360
gcgagcagcg attttggcgt tatcatttga cgatatttct ggaatgacga atcctgtttc    420
tactaacttt ttggtaggac aaagtgaaac aatcaagaag atagcttctc ctcctatttg    480
tggaagaaat tgaactcctc tagatgatct actgacgata gtatctcctt gacagatatt    540
ggaccgaatt acagaagtac ctggaatgta aagccctgaa accccctcat tttttaagca    600
gattgttgcc gtaaatcctg cactatgccc aagatagaga gctcctttgg tgaatccatc    660
tctatgtttc agtttaacca agaaacagtc agctggtcta aaatttccat ctctatctaa    720
tacagcatct aacttgatgt caggaactat gaccggttta atgttatatg taacattgag    780
taaatcctta agttcataat catcactgtc atcagttatg tacgatccaa acaatgtttc    840
taccggcata gtggatacga agatgctatc catcagaatg tttccctgat tagtattttc    900
tatatagcta ttcttcttta aacgattttc caaatcagta actatgttca ttttttttagg    960 agtaggacgc ctagccagta tggaagagga ttttctagat cctctcttca acatctttga   1020
tctcgatgga atgcaaaacc ccatagtgaa acaaccaacg ataaaaataa tattgttttt   1080 cacttttttat aatttttacca tctgactcat ggattcatta atatctttat aagagctact   1140
aacgtataat tctttataac tgaactgaga tatatacacc ggatctatgg tttccataat   1200
tgagtaaatg aatgctcggc aataactaat ggcaaatgta taaaacaacg aaattatact   1260
agagttgtta aagttaatat tttctatgag ctgttccaat aaattatttg ttgtgactgc   1320
gttcaagtca taaatcatct tgatactatc cagtaaacag tctttaagtt ctggaatatt   1380
atcatcccat tgtaaagccc ctaattcgac tatcgaatat cctgctctga tagcagtttc   1440
```

-continued

```
aatatcgacg gacgtcaata ctgtaataaa ggtggtagta ttgtcatcat cgtgataaac    1500
tacgggaata tggtcgttag taggtacggt gactttacac aacgcgatat ataactttcc    1560
ttttgtacca ttttttaacgt agttgggacg tcctgcaggg tattgttttg aagaaatgat    1620
atcgagaaca gatttgatac gatatttgtt ggattcctga ttattcacta taatataatc    1680
tagacagata gatggattcga taaatagaga aggtatatcg ttggtaggat aatacatccc    1740
cattccagta ttctcggata ctctattgat gacactagtt aagaacatgt cttctattct    1800
agaaaacgaa aacatcctac atggactcat taaaacttct aacgctcctg attgtgtctc    1860
gaatgcctcg tacaaggatt tcaaggatgc catagattct ttgacctaag tagggataac    1920
agggtaatcg atttattcaa caaagccacg ttgtgtctca aaatctctga tgttacattg    1980
cacaagataa aaatatatca tcatgaacaa taaaactgtc tgcttacata aacagtaata    2040
caaggggtgt tatgagccat attcaacggg aaacgtcttg ctcgaggccg cgattaaatt    2100
ccaacatgga tgctgattta tatgggtata aatgggctcg cgataatgtc gggcaatcag    2160
gtgcgacaat ctatcgattg tatgggaagc ccgatgcgcc agagttgttt ctgaaacatg    2220
gcaaaggtag cgttgccaat gatgttacag atgagatggt cagactaaac tggctgacgg    2280
aatttatgcc tcttccgacc atcaagcatt ttatccgtac tcctgatgat gcatggttac    2340
tcaccactgc gatccccggg aaaacagcat tccaggtatt agaagaatat cctgattcag    2400
gtgaaaatat tgttgatgcg ctggcagtgt tcctgcgccg gttgcattcg attcctgttt    2460
gtaattgtcc ttttaacagc gatcgcgtat ttcgtctcgc tcaggcgcaa tcacgaatga    2520
ataacggttt ggttgatgcg agtgattttg atgacgagcg taatggctgg cctgttgaac    2580
aagtctggaa agaaatgcat aagcttttgc cattctcacc ggattcagtc gtcactcatg    2640
gtgatttctc acttgataac cttatttttg acgaggggaa attaataggt tgtattgatg    2700
ttggacgagt cggaatcgca gaccgatacc aggatcttgc catcctatgg aactgcctcg    2760
gtgagttttc tccttcatta cagaaacggc tttttcaaaa atatggtatt gataatcctg    2820
atatgaataa attgcagttt catttgatgc tcgatgagtt tttctaatca gaattggtta    2880
attggttgta acactggcaa tgcctcgtac aaggatttca aggatgccat agattctttg    2940
accaacgatt tagaattgcg tttagcatct gattttttta ttaaatcgaa tggtcggctc    3000
tctggtttgc taccccaatg ataacaatag tcttgtaaag ataaaccgca agaaaattta    3060
tacgcatcca tccaaataac cctagcacca tcggatgata ttaatgtatt attatagatt    3120
ttccatccac aattattggg ccagtatact gttagcaacg gtatatcgaa tagattactc    3180
atgtaaccta ctagaatgat agttcgtgta ctagtcataa tatctttaat ccaatctaag    3240
aaatttaaaa ttagattttt tacactgtta aagttaacaa aggtattacc cggatacgtg    3300
gatatcatat atggcattgg tccattatca gtaatagctc cataaactga tacggcgatg    3360
gtttttatat gtgtttgatc taacgaggaa gaaattcgcg cccacaattc atctctagat    3420
atgtatttaa tatcaaacgg taacacatca atttcgggac gcgtatatgt ttctaaattt    3480
ttaatccaaa tataatgatg acctatatgc cctattatca tactgtcaac tatagtacac    3540
ctagagaact tacgatacat ctgtttccta taatcgttaa attttacaaa tctataacat    3600
gctaaacctt ttgacgacaa ccattcatta atttctgata tggaatctgt attctcgata    3660
ccgtattgtt ctaaagccag tgctatatct ccctgttcgt gggaacgctt tcgtataata    3720
tcgatcaacg gataatctga agtttttgga gaataatatg actcatgatc tatttcgtcc    3780
ataaacaatc tagacatagg aattggaggc gatgatctta attttgtgca atgagtcgtc    3840
```

-continued

```
aatcctataa cttctaatat tgtaatattc atcatcgaca taacactatc tatgttatca    3900
tcgtatatta gtataccacg gccttcttca tttcgtgcca aaataatata cagtcttaaa    3960
taattacgca atatctcaat agtttcataa ttgttagctg ttttcatcaa ggtttgtatc    4020
ctgtttaaca tgatggcgtt ctataacgtc tctattttct attttttaatt ttttaaattt    4080 ttaacgattt actgtggcta gatacccaat ctctctcaaa tattttttta gcctcgctta    4140
caagctgttt atctatacta ttaaaactga cgaatccgtg attttggtaa tgggttccgt    4200
cgaaatttgc cgaagtgata tgaacatatt cgtcgtcgac tatcaacaat tttgtattat    4260
tctgaatagt gaaaaccttc acagatagat cattttgaac acacaacgcg tctagacttc    4320
tggcggttgc catagaatat acgtcgttct tatcccaatt accaactaga agtctgatct    4380
taactcctct attaatggct gcttctataa tggagttgta aatgtcaggc caatagtagc    4440
tattaccgtc gacacgtgta gtgggaacta tggccaaatg ttcaatatct atactagtct    4500
tagccgactt gagtttatca ataactacat cagtgtctag atctctagaa tatcccaata    4560
ggtgttctgg agaatcagta aagaacactc cacctatagg attcttaata tgatacgcag    4620
tgctaactgg cagacaacaa gccgcagagc ataaattcaa ccatgaattt tttgcgctat    4680
taaaggcttt aaaagtatca aatcttctac gaagatctgt ggccagcggg ggataatcag    4740
aatatacacc taacgtttta atcgtatgta tagatcctcc agtaaatgac gcgtttccta    4800
cataacatct ttcatcatct gacacccaaa aacaaccgag tagtagtccc acattatttt    4860
ttttatctat attaacggtt ataaaattta tatccgggca gtgactttgt agctctccca    4920
gatttctttt ccctcgttca tctagcaaaa ctattatttt aatccctttt tcagatgcct    4980
cttttagttt atcaaaaata agcgcgcccc tagtcgtact cagaggatta caacaaaaag    5040
atgctatgta tatatatttc ttagctagag tgataatttc gttaaaacat tcaaatgttg    5100
ttaaatgatc ggatctaaaa tccatatttt ctggtagtgt ttctaccagc ctacattttg    5160
ctcccgcagg taccggtgca aatggccaca tttagttaac ataaaaactt atacatcctg    5220
ttctatcaac gattctagaa tatcatcggc tatatcgcta aaattttcat caaagtcgac    5280
atcacaacct aactcagtca atatattaag aagttccatg atgtcatctt cgtctatttc    5340
tatatccgta tccattgtag attgttgacc gattatcgag tttaaatcat tactaatact    5400
caatccttca gaatacaatc tgtgtttcat tgtaaattta taggcggtgt atttaagttg    5460
gtagattttc aattatgtat taatatagca acagtagttt ttgctcctcc ttgattctag    5520
catcctcttc attattttct tctacgtaca taagcatgtc caatacgtta gacaacacac    5580
cgacgatggc ggccgccaca gacacgaata tgactaaacc gatgaccatt taaaaacccc    5640
tctctagctt tcacttaaac tgtatcgatc attcttttag cacatgtata atataaaaac    5700
attattctat ttcgaattta ggcttccaaa aatttttcat ccgtaaaccg ataataatat    5760
atatagactt gttaatagtc ggaataaata gattaatgct taaactatca tcatctccac    5820
gattagagat acaatattta cattcttttt gctgtttcga aactttatca atacacgtta    5880
atacaaaccc aggaaggaga tattgaaact gaggctgttg aaaatgaaac ggtgaataca    5940
ataattcaga taatgtaaaa tcatgattcc gtattctgat gatattagaa ctgctaatgg    6000
atgtcgatgg tatgtatcta ggagtatcta ttttaacaaa gcatcgattt gctaatatac    6060
aattatcatt ttgattaatt gttattttat tcatattctt aaaaggtttc atatttatca    6120
attcttctac attaaaaatt tccattttta atttatgtag ccccgcaata ctcctcatta    6180
```

-continued cgtttcattt tttgtctata                                                      6200

<210> SEQ ID NO 37
<211> LENGTH: 20
<212> TYPE: DNA
<213> ORGANISM: Artificial Sequence
<220> FEATURE:
<223> OTHER INFORMATION: B5R modification-proving primer Fw

<400> SEQUENCE: 37
atccaagaag ctggatgcgg                                                      20

<210> SEQ ID NO 38
<211> LENGTH: 20
<212> TYPE: DNA
<213> ORGANISM: Artificial Sequence
<220> FEATURE:
<223> OTHER INFORMATION: B5R modification-proving primer Re

<400> SEQUENCE: 38
tggatgatgg agaccccgtt                                                      20

<210> SEQ ID NO 39
<211> LENGTH: 21
<212> TYPE: DNA
<213> ORGANISM: Artificial Sequence
<220> FEATURE:
<223> OTHER INFORMATION: C11R deletion-proving primer Fw

<400> SEQUENCE: 39
agaaccagct gctccatgat t                                                    21

<210> SEQ ID NO 40
<211> LENGTH: 20
<212> TYPE: DNA
<213> ORGANISM: Artificial Sequence
<220> FEATURE:
<223> OTHER INFORMATION: C11R deletion-proving primer Re

<400> SEQUENCE: 40
gatacggaac cacccactgt                                                      20

<210> SEQ ID NO 41
<211> LENGTH: 20
<212> TYPE: DNA
<213> ORGANISM: Artificial Sequence
<220> FEATURE:
<223> OTHER INFORMATION: O1L deletion-proving primer Fw

<400> SEQUENCE: 41
tgtcaacgga ccccaacatc                                                      20

<210> SEQ ID NO 42
<211> LENGTH: 20
<212> TYPE: DNA
<213> ORGANISM: Artificial Sequence
<220> FEATURE:
<223> OTHER INFORMATION: O1L deletion-proving primer Re

<400> SEQUENCE: 42
acatggacgc attgggtgat                                                      20

<210> SEQ ID NO 43
<211> LENGTH: 22
<212> TYPE: DNA
<213> ORGANISM: Artificial Sequence -continued

```
<220> FEATURE:
<223> OTHER INFORMATION: F4L deletion-proving primer Fw

<400> SEQUENCE: 43
caaggtctag acaaaccctc gt                                          22

<210> SEQ ID NO 44
<211> LENGTH: 20
<212> TYPE: DNA
<213> ORGANISM: Artificial Sequence
<220> FEATURE:
<223> OTHER INFORMATION: F4L deletion-proving primer Re

<400> SEQUENCE: 44
gcttcccaca acaatctcgc                                             20

<210> SEQ ID NO 45
<211> LENGTH: 20
<212> TYPE: DNA
<213> ORGANISM: Artificial Sequence
<220> FEATURE:
<223> OTHER INFORMATION: A33R modification-proving primer Fw

<400> SEQUENCE: 45
aggttgcgtc tagcactacg                                             20

<210> SEQ ID NO 46
<211> LENGTH: 20
<212> TYPE: DNA
<213> ORGANISM: Artificial Sequence
<220> FEATURE:
<223> OTHER INFORMATION: A33R modification-proving primer Re

<400> SEQUENCE: 46
tgtatccatc cattggcgca                                             20

<210> SEQ ID NO 47
<211> LENGTH: 20
<212> TYPE: DNA
<213> ORGANISM: Artificial Sequence
<220> FEATURE:
<223> OTHER INFORMATION: A34R modification-proving primer Fw

<400> SEQUENCE: 47
aagcaaattg cactgcggaa                                             20

<210> SEQ ID NO 48
<211> LENGTH: 20
<212> TYPE: DNA
<213> ORGANISM: Artificial Sequence
<220> FEATURE:
<223> OTHER INFORMATION: A34R modification-proving primer Re

<400> SEQUENCE: 48
cggtcaccgt gataagaggt                                             20

<210> SEQ ID NO 49
<211> LENGTH: 20
<212> TYPE: DNA
<213> ORGANISM: Artificial Sequence
<220> FEATURE:
<223> OTHER INFORMATION: A36R modification-proving primer Fw

<400> SEQUENCE: 49
agacggcaat ggatggatca                                             20
```

-continued

```
<210> SEQ ID NO 50
<211> LENGTH: 20
<212> TYPE: DNA
<213> ORGANISM: Artificial Sequence
<220> FEATURE:
<223> OTHER INFORMATION: A36R modification-proving primer Re

<400> SEQUENCE: 50
tacaacgtga cggcagcaat                                                     20

<210> SEQ ID NO 51
<211> LENGTH: 20
<212> TYPE: DNA
<213> ORGANISM: Artificial Sequence
<220> FEATURE:
<223> OTHER INFORMATION: A56R modification-proving primer Fw

<400> SEQUENCE: 51
aatcccgctc tatggtcagc                                                     20

<210> SEQ ID NO 52
<211> LENGTH: 20
<212> TYPE: DNA
<213> ORGANISM: Artificial Sequence
<220> FEATURE:
<223> OTHER INFORMATION: A56R modification-proving primer Re

<400> SEQUENCE: 52
agaaagtttc cggcggctat                                                     20

<210> SEQ ID NO 53
<211> LENGTH: 20
<212> TYPE: DNA
<213> ORGANISM: Artificial Sequence
<220> FEATURE:
<223> OTHER INFORMATION: B5R modification-proving primer Fw

<400> SEQUENCE: 53
tgcgtactac ctgctgttgt                                                     20

<210> SEQ ID NO 54
<211> LENGTH: 20
<212> TYPE: DNA
<213> ORGANISM: Artificial Sequence
<220> FEATURE:
<223> OTHER INFORMATION: B5R modification-proving primer Re

<400> SEQUENCE: 54
aaatgctcta acggcatcgt                                                     20

<210> SEQ ID NO 55
<211> LENGTH: 24
<212> TYPE: DNA
<213> ORGANISM: Artificial Sequence
<220> FEATURE:
<223> OTHER INFORMATION: F12-13L modification-proving primer Fw

<400> SEQUENCE: 55
tggatacgaa gatgctatcc atca                                                24

<210> SEQ ID NO 56
<211> LENGTH: 20
<212> TYPE: DNA
<213> ORGANISM: Artificial Sequence
<220> FEATURE:
<223> OTHER INFORMATION: F12-13L modification-proving primer Re
```

-continued

```
<400> SEQUENCE: 56
ccaattccta tgtctagatt                                          20

<210> SEQ ID NO 57
<211> LENGTH: 20
<212> TYPE: DNA
<213> ORGANISM: Artificial Sequence
<220> FEATURE:
<223> OTHER INFORMATION: A56R modification-proving primer Fw

<400> SEQUENCE: 57
tctccatacg atgatctagt                                          20

<210> SEQ ID NO 58
<211> LENGTH: 20
<212> TYPE: DNA
<213> ORGANISM: Artificial Sequence
<220> FEATURE:
<223> OTHER INFORMATION: F12-13L modification-proving primer Fw

<400> SEQUENCE: 58
tgtactagtc ataatatctt                                          20

<210> SEQ ID NO 59
<211> LENGTH: 20
<212> TYPE: DNA
<213> ORGANISM: Artificial Sequence
<220> FEATURE:
<223> OTHER INFORMATION: F12-13L modification-proving primer Fw

<400> SEQUENCE: 59
aatctagaca taggaattgg                                          20

<210> SEQ ID NO 60
<211> LENGTH: 20
<212> TYPE: DNA
<213> ORGANISM: Artificial Sequence
<220> FEATURE:
<223> OTHER INFORMATION: F12-13L modification-proving primer Fw

<400> SEQUENCE: 60
ctctattaat ggctgcttct                                          20

<210> SEQ ID NO 61
<211> LENGTH: 23
<212> TYPE: DNA
<213> ORGANISM: Artificial Sequence
<220> FEATURE:
<223> OTHER INFORMATION: BACgfp synthesis primer Fw

<400> SEQUENCE: 61
cgggactatg gacgcatgat aag                                      23

<210> SEQ ID NO 62
<211> LENGTH: 23
<212> TYPE: DNA
<213> ORGANISM: Artificial Sequence
<220> FEATURE:
<223> OTHER INFORMATION: BACgfp synthesis primer Re

<400> SEQUENCE: 62
aaatccgccg tactaggttc att                                      23

<210> SEQ ID NO 63
```

```
<211> LENGTH: 4209
<212> TYPE: DNA
<213> ORGANISM: Artificial Sequence
<220> FEATURE:
<223> OTHER INFORMATION: RLuc expression cassette

<400> SEQUENCE: 63
acattgcttt aaaatggacg gcgctaacaa ctgtcatacg agtattaatg gatagcggac      60
tagtcaataa ggaattaatt ttaccatttg tcattgtctt aacccattcg ttgattagtt     120
cctttgtttg gttagcatta ttaaagttta cagtttgaaa atcgtctttt attttttgta     180
ggaaggaggc atggaactcg atactatcgc taccgtatat tttatttgcg gtagctagtg     240
tcgcacaata cggaatatct acgtccatgt cattattgtc atcgggtgta ttctcattca     300
tattctctat atattttgat agttgttcag ctgtagaacc agctgctcca tgatttagaa     360
tagataaagt agataaaata gaaactggag aaatcaaaac attttcatcc gtgtgtttta     420
agattagttc tttaaagata tccatggtat agaccaaaca ataacgataa cgatatatat     480
cataaataaa taatgttaaa ttttagttta tgtttgtacc ccgtattcat acttaacaaa     540
ttggtattgc gtacacaatc aatcatatta cataccatta ataatgcaag cataaaaaat     600
cgttagtaga tgtttctaaa tataggtcc gtaagcaaag aatataagaa tgaagcggta      660
atgataaaat caattgttat ctaaaatgat catactcatt tattttattc tattatatta     720
acacatacat ttttaacagc aacacattca atattgtatt gttatttta tattatttac       780 acaattaaca atatattatt agtttatatt actgaattaa taatataaaa ttcccaatct     840
tgtcataaac acacactgag aaacagcata aacacaaaat ccatcaaaat tattgttcat     900
ttttgagaac tcgctcaacg aacgatttga tatattttcc catttcatca ggtgcatctt     960
cttgcgaaaa atgaagacct tttactttga caaattcagt attaggaaac ttcttggcac    1020
cttcaacaat agcattggaa aagaatcctg ggtccgattc aataaacatt tttggtaaat    1080
catcacttgc acgtagataa gcattataat tcctaacaat ttgtacaacg tcaggtttac    1140 cacctttac taacgggatt tcacgaggcc atgataatgt tggacgacga acttcacctt     1200
tctcttttgc cagtgttaca accaattaac caattctgat tagaaaaact catcgagcat    1260
caaatgaaac tgcaatttat tcatatcagg attatcaata ccatatttt gaaaaagccg      1320 tttctgtaat gaaggagaaa actcaccgag gcagttccat aggatggcaa gatcctggta    1380
tcggtctgcg attccgactc gtccaacatc aatacaacct attaatttcc cctcgtcaaa    1440
aataaggtta tcaagtgaga atcaccatg agtgacgact gaatccggtg agaatggcaa      1500
aagcttatgc atttctttcc agacttgttc aacaggccag ccattacgct cgtcatcaaa    1560
atcactcgca tcaaccaaac cgttattcat tcgtgattgc gcctgagcga cgaaaatac      1620 gcgatcgctg ttaaaaggac aattacaaac aggaatcgaa tgcaaccggc gcaggaacac    1680
tgccagcgca tcaacaatat tttcacctga atcaggatat tcttctaata cctggaatgc    1740
tgttttcccg gggatcgcag tggtgagtaa ccatgcatca tcaggagtac ggataaaatg    1800
cttgatggtc ggaagaggca taaattccgt cagccagttt agtctgacca tctcatctgt    1860
aacatcattg gcaacgctac ctttgccatg tttcagaaac aactctggcg catcgggctt    1920
cccatacaat cgatagattg tcgcacctga ttgcccgaca ttatcgcgag cccatttata    1980
cccatataaa tcagcatcca tgttggaatt taatcgcggc ctcgagcaag acgtttcccg    2040
ttgaatatgg ctcataacac cccttgtatt actgtttatg taagcagaca gttttattgt    2100
tcatgatgat atatttttat cttgtgcaat gtaacatcag agattttgag acacaacgtg    2160
```

```
gctttgttga ataaatcgat taccctgtta tccctactta gccatgataa tgttggacga      2220
cgaacttcac ctttctcttt gaatggttca agatatgctg caaattcttc tggttctaac      2280
tttctcatga tttttgatgg caacatggtt tccacgaaga agttattctc caaaaccatt      2340
ttttctcctt cttcagattt gatcaacgca atatcttctt caatatcagg ccattcatcc      2400
catgattcaa tcacatctac tacactttca gcgtgaacta ttgctttgat cttatcttga      2460
tgctcatagc tataatgaaa tgccaaacaa gcaccccaat catggccgac aaaaatgatc      2520
ttctttggta aattaagaag ttcaaaccat gcagtaagat atttgtaatg atcaagtaac      2580
ctataagaac cattaccaga tttgcctgat ttgcccatac caataaggtc tggtataata      2640
caccgcgcta ctggctcaat atgtggcaca acatgtcgcc ataaataaga agaggccgcg      2700
ttaccatgta aaaaaataac agcattttct gcatgttttt ctgaatcata ataattaata      2760
aatgaatcaa gaacattcat ttgtttacat ctggcccacc actgcggacc agttatcatc      2820
cgtttccttt gttctggatc ataaactttc gaagtcatgg tggcgaccgg tgctagcgta      2880
ccagaccgcc acggcttacg gcaataatgc ctttccattg ttcagaaggc atcagtcggc      2940
ttgcgagttt acgtgcatgg atctgcaaca tgtcccaggt gacgatgtat ttttcgctca      3000
tgtgaagtgt cccagcctgt ttatctacgg cttaaaaagt gttcgagggg aaaataggtt      3060
gcgcgagatt atagagatcc gtcactgttc tttatgatct acttccttac cgtgcaataa      3120
attagaatat attttctact tttacgagaa attaattatt gtatttatta tttatgggtg      3180
aaaaacttac tataaaaagc gggtgggttt ggaattagtg atcagtttat gtatatcgca      3240
actaccggca tatggctatt cgacatcgag aacattaccc acatgataag agattgtatc      3300
agtttcgtag tcttgagtat tggtattact atatagtata tgtcgggaat tcatcgatgt      3360
agactatcaa cgttcagaaa acccaaacac tacaacgtca tatatcccat ctcccggtat      3420
tatgcttgta ttagtaggca ttattattat tacgtgttgt ctattatctg tttataggtt      3480
cactcgacga actaaactac ttatacaaga tatggttgtg ccataatttt tataaatttt      3540
ttttatgagt attttttacaa aaatgtataa agtgtatgtc ttatgtatat ttataaaaat      3600
gctaaatatg cgatgtatct atgttatttg tatttatcta aacaataacct ctacctctag      3660 atattataca aaaatttttt atttcagcat attaaagtaa aatctagtta ccttgaaaat      3720
gaatacagtg ggtggttccg tatcaccagt aagaacataa tagtcgaata cagtatccga      3780
ttgagatttt gcatacaata ctagtctaga aagaaatttg taatcatttt ctgtgacggg      3840
agtccatata tctgtatcat cgtctagttt atcagtgtcc catgctatat tcctgttatc      3900
atcattagtt aatgaaaata actctcgtgc ttcagaaaag tcaaatattg tatccataca      3960
tacatctcca aaactatcgc ttatacgttt atctttaacg ataccctatac ctagatggtt      4020 atttactaac agacattttc cagatctatt gactataact cctatagttt ccacatcaac      4080
caagtaatga tcatctattg ttatataaca ataacataac tcttttccat ttttatcagt      4140
atgtatatct atatcaacgt cgtcgttgta gtgaatagta gtcattgatc tattatatga      4200
aacggatat                                                             4209
```

ONCOLYTIC VACCINIA VIRUS

TECHNICAL FIELD

The present invention relates to an oncolytic vaccinia virus that can be intravenously administered and has the features of improving safety by restricting a virus replication in normal cells by impairing the functions of vaccinia virus growth factor (VGF), extracellular signal-regulated kinase (ERK)-activating protein, and ribonucleotide reductase (RNR), and improving virus production in tumor cells and in host cells used for industrial production by changing an amino acid residue(s) of a protein(s) involving formation of virions of extracellular enveloped virus (EEV) of vaccinia virus. The vaccinia virus of the present invention has improved virus safety and productivity, and can be effectively used as an anticancer agent.

BACKGROUND ART

A Mitogen-activated protein kinase-Dependent Recombinant Vaccinia Virus (MD-RVV) has been disclosed as an oncolytic vaccinia virus in which both genes encoding vaccinia virus growth factor (hereinafter, also referred to as "VGF") and O1L protein, which is a protein that activates extracellular signal-regulated kinase (hereinafter, also referred to as "ERK") are deleted to restrict growth in normal cells, however specifically proliferate in cancer cells, thereby damaging the cancer cells (Patent Document 1).

The vaccinia virus utilizes the epidermal growth factor (hereinafter, also referred to as "EGF") receptor signaling pathway to promote the spread of the virus through rapid and direct motility of infected cells (Non-Patent Document 1). C11R protein, a vaccinia virus growth factor (VGF) that is highly homologous to EGF and is secreted at an early stage of vaccinia virus infection, binds to an EGF receptor on infected cells and surrounding cells to transduce a signal through the MAP kinase cascade (Ras/Raf/MEK/ERK metabolic pathway). In addition, the O1L protein of vaccinia virus constitutively activates extracellular signal-regulated kinase (ERK) in infected cells and promotes the pathogenicity of the virus (Non-Patent Document 2). The C11R and O1L deficient virus (MD-RVV) lowers viral growth because ERK cannot be activated in normal cells. In cancer cells with abnormally activated ERK pathways, however, the inactivated virus ERK activation function is complemented, and the virus proliferates and becomes an oncolytic virus that destroys the cancer cells (Patent Document 1).

In order to reduce virus toxicity, disclosed is an oncolytic virus using a poxvirus in which the ribonucleotide reductase encoded in the viral genome is inactivated (Patent Document 2).

It is well known that a point mutation at amino acid position K151 of the A34R polypeptide of vaccinia virus improves the production of extracellular enveloped virus (Non-Patent Document 3 and Patent Document 3).

PRIOR ART DOCUMENTS

Patent Documents

Patent Document 1: JP-A-2015-076422
Patent Document 2: JP-A-2011-504104
Patent Document 3: JP-A-2006-506974

Non-Patent Documents

Non-Patent Document 1: Beerli C., et al., Nature Microbiology, 4(2), 216-225, 2019

Non-Patent Document 2: Schweneker, M., et al., Journal of Virology, 86(4), 2323-2336, 2012
Non-Patent Document 3: Blasco, R., et al., Journal of Virology, 67(6), 3319-3325, 1993
Non-Patent Document 4: Downs-Canner, S., et al., Molecular Therapy, 24(8), 1492-1501, 2016
Non-Patent Document 5: Loren, K., et al., Clinical Cancer Research, 23(19), 5696-5702, 2017
Non-Patent Document 6: McIntosh A. A., Smith G. L., Journal of Virology, 70(1), 272-281, 1996
Non-Patent Document 7: Ferguson M. S., et al., Advances in Virology, 2012, 805629, 2012
Non-Patent Document 8: Badrinath N, et al., International Journal of Nanomedicine, 11, 4835-4847, 2016
Non-Patent Document 9: Bernet J., et al., Journal of Biosciences, 28(3), 249-264, 2003
Non-Patent Document 10: Dehaven B. C., et al., Journal of General Virology, 92, 1971-1980, 2011
Non-Patent Document 11: Chung, C.-S., Journal of Virology, 72(2), 1577-1585, 1998
Non-Patent Document 12: Gammon, D. B., et al., PLOS Pathogens, 6(7), e1000984, 2010
Non-Patent Document 13: Aye Y., et al., Oncogene, 34(16), 2011-2021, 2015
Non-Patent Document 14: Engstroem Y., et al., The Journal of Biological Chemistry, 260(16), 9114-9116, 1985
Non-Patent Document 15: Torii, S., et al., Cancer Science, 97(8), 697-702, 2006

SUMMARY OF THE INVENTION

Problems to be Solved by the Invention

Oncolytic vaccinia viruses are expected to be effective not only for treatment of a primary tumor by intratumoral administration but also for systemic micrometastasis by systemic administration using an intravenous injection. However, in a previous clinical trial in which an oncolytic vaccinia virus was administered intravenously, adverse effects associated with virus excretion were observed along with results suggesting efficacy (Non-Patent Document 4; Non-Patent Document 5). Further improvement in the safety of the oncolytic virus has been sought.

On the other hand, oncolytic viruses that have been genetically modified to suppress the virus proliferation in normal cells to improve safety are different from their parent strain virus before genetic modification in cancer cells and host cells used for industrial production. In comparison, it is often accompanied by a decrease in virus proliferation, and there is a concern about a decrease in efficacy and productivity. Thus, it has been desired to improve the safety of the virus as well as the productivity.

However, for improved efficacy and productivity, it is useful to modify the gene(s) encoding the extracellular enveloped virus (EEV)-related protein(s) to increase the proportion of EEV. However, the increase in EEV production involves virus toxicity (Non-Patent Document 6).

Previously reported clinical trial data about intravenous administration of oncolytic viruses have shown that the viruses can be safely and systemically delivered with limited toxicity, however there are individual differences in efficacy. Such incompleteness has been found. This is mainly because at the dose and dosage regimen that have been confirmed to be safe, the virus is rapidly cleared from the circulation before it reaches its target. This phenomenon occurs primarily due to neutralizing antibodies, complement activation, antiviral cytokines, and endogenous tissue macrophages, with non-specific uptake by other tissues such as the lung, liver and spleen (Non-Patent Document 7). Among the oncolytic viruses, vaccinia virus has become a focus of preclinical and clinical studies due to its many favorable properties (Non-Patent Document 8). Some oncolytic vaccinia viruses have been clinically tested by intravenous administration. The vaccinia virus complement regulatory protein secreted by vaccinia virus (hereinafter also referred to as "VCP") binds and inactivates complements C4b and C3b, thereby inhibiting the classical and alternative pathways of complement activation (Non-Patent Document 9). In addition, the vaccinia virus in the EEV form incorporates a host protein in its membrane, which protein can prevent complement activation, and the EEV protein A56R also fixes the secreted VCP to protect it from complement attacks (Non-Patent Document 10).

The vaccinia virus does not have a specific receptor. Here, glycosaminoglycans, such as heparan sulfate, which are ubiquitously present in all tissues primarily including a connective tissue of animals, mediate the interaction between the vaccinia virus and host cells. The virus fuses directly with the plasma membrane and enters a tumor cell by endocytosis (Non-Patent Document 11). Thus, oncolytic vaccinia viruses do not exhibit cell preference specific to the organ, and should have a therapeutic effect on a wide range of cancer types. On the other hand, upon treatment by intravenous administration, systemic side effects due to viral growth become a problem. In order to solve this problem, it is necessary to strictly restrict the intracellular viral replication that occurs after the vaccinia virus infects normal cells and invades them. In general, since the effective range and the toxic range of each anticancer drug are close to each other, adverse effects occur at the dose and dosage regimen expected to be effective.

Solutions to the Problems

The vaccinia virus genome has a gene encoding ribonucleotide reductase (hereinafter also referred to as "RNR"), which is a rate-limiting enzyme in DNA synthesis and includes I4L (large subunit; RRM1) and F4L (small subunit; RRM2). F4L is required for efficient replication in cultured cells and virus toxicity in mice (Non-Patent Document 12). Meanwhile, elevated RNR expression in cells is characteristic of many cancers, and as a result of investigating RNR gene expression in human cancers by using the ONCOMINE database, RRM2 was ranked in top 10% among genes most overexpressed in 73 of 168 cancers analyzed (Non-Patent Document 13). In addition, RNR activity in mammals is cell cycle-dependent, and the protein level of RRM1 are constant throughout the cell cycle, while RRM2 is expressed in the G1/S phase during DNA replication, and cell cycle-dependent enzyme activity is regulated by the level of RRM2 (Non-Patent Document 14). By contrast, the progression of the cell cycle from G1 phase to S phase is triggered by the activated ERK pathway (Non-Patent Document 15). Accordingly, the vaccinia virus with inhibited F4L functions can replicate using cell-derived RRM2 in cancer cells where the cells are actively proliferating. In normal cells, however, the expression level of RRM2 is low, so that viral replication is restricted. Further deletion of F4L from MD-RVV in which the functions of C11R and O1L are inhibited significantly suppresses viral growth in normal cells and further improves safety.

It is predicted that oncolytic viruses, which are growth-restricted viruses that cannot proliferate in normal cells and can selectively grow in target cancer cells, tend to have a less growth potential than parental viruses even in tumor cells and host cells used for industrial production. The oncolytic vaccinia virus, from which the F4L gene as well as the above-mentioned C11R and o1L genes have been deleted, complements ERK and RNR which are required for viral replication, by using enzymes in the highly replicative cancer cells, so that the virus can replicate.

As a method of further complementing productivity of a virus that lacks the functions of ERK and RNR related to cell proliferation, the present inventors have focused on a virion formation-related molecule(s) expressed during the late phase of virus life cycle while complementing the ERK and RNR activities by using enzymes derived from cancer cells. Here, there are four different forms of virion of vaccinia virus (including intracellular mature virus (hereinafter, also referred to as "IMV"), intracellular enveloped virus (hereinafter, also referred to as "IEV"), cell-associated enveloped virus (hereinafter, also referred to as "CEV"), and extracellular enveloped virus (hereinafter, also referred to as "EEV")). The genes encoding the seven different proteins (A33R, A34R, A36R, A56R, B5R, F12L, and F13L) that are components of EEV may be replaced with the corresponding genes of another vaccinia virus strain having a high EEV productivity. This has been found to improve viral productivity and make intravenous administration safe. Then, the present invention has been completed.

The present invention provides the following [1] to [20].

[1] A vaccinia virus deficient in functions of vaccinia virus growth factor (VGF), extracellular signal-regulated kinase (ERK)-activating protein, and ribonucleotide reductase (RNR).

[2] The virus according to [1], which is a growth-restricted virus having improved safety, wherein the virus does not replicate in a normal cell and can selectively replicate in a proliferating cell.

[3] The virus according to [1] or [2], wherein all or part of regions of each of C11R, O1L, and F4L genes have been deleted or modified, and the functions of these gene products have been inactivated.

[4] A growth-restricted vaccinia virus deficient in functions of vaccinia virus growth factor (VGF), extracellular signal-regulated kinase (ERK)-activating protein, and ribonucleotide reductase (RNR), wherein a gene(s) encoding extracellular enveloped virus (EEV)-related protein(s) is replaced by a corresponding gene(s) of another vaccinia virus strain having a high EEV productivity, and wherein the virus does not replicate in a normal cell and can selectively replicate in a proliferating cell, thereby having improved safety and productivity.

[5] The virus according to [4], wherein all or part of regions of each of C11R, O1L, and F4L genes have been deleted or modified to inactivate the functions of these gene products.

[6] The virus according to [4] or [5], wherein the gene(s) encoding the extracellular enveloped virus (EEV)-related protein(s) is one or more genes selected from the group consisting of A33R, A34R, A36R, A56R, B5R, F12L, and F13L, and has been replaced by a corresponding gene(s) of another vaccinia virus strain having a high EEV productivity.

[7] The virus according to [4] or [5], wherein the genes encoding the extracellular enveloped virus (EEV)-related proteins are A33R, A36R, A56R, B5R, F12L, and F13L, and have been replaced by corresponding genes of another vaccinia virus strain having a high EEV productivity.

[8] The virus according to [4] or [5], wherein the genes encoding the extracellular enveloped virus (EEV)-related proteins are A33R, A34R, A36R, A56R, B5R, F12L, and F13L, and have been replaced by corresponding genes of another vaccinia virus strain having a high EEV productivity.

[9] The virus according to any one of [4] to [8], wherein another vaccinia virus strain having a high EEV productivity is IHD-J strain or IHD-W strain.

[10] A pharmaceutical composition for treating a cancer, comprising the virus according to any one of [1] to [9].

[11] The pharmaceutical composition according to [10], which is for intravenous administration, intraperitoneal administration, or intratumoral administration.

[12] A growth-restricted vaccinia virus vector, which is the virus according to any one of [1] to [9] into which a foreign DNA has been introduced.

[13] The vector according to [12], wherein the foreign DNA is a gene encoding a cancer-specific antigen, an immune response regulator, or a protein with affinity for a cancer cell surface antigen. [14] A growth-restricted vaccinia virus having improved productivity, wherein a DNA sequence(s) of a gene(s) encoding extracellular enveloped virus (EEV)-related protein(s) of the growth-restricted vaccinia virus has been replaced by a DNA sequence(s) of a corresponding gene(s) of another vaccinia virus strain having a high EEV productivity, and wherein the growth-restricted vaccinia virus does not replicate in a normal cell, and can selectively replicate in a proliferating cell.

[15] The virus according to [14], wherein the gene(s) encoding the extracellular enveloped virus (EEV)-related protein(s) is one or more genes selected from the group consisting of A33R, A34R, A36R, A56R, B5R, F12L, and F13L.

[16] The virus according to [14], wherein the genes encoding the extracellular enveloped virus (EEV)-related proteins are A33R, A36R, A56R, B5R, F12L, and F13L genes.

[17] The virus according to [14], wherein the genes encoding the extracellular enveloped virus (EEV)-related proteins are A33R, A34R, A36R, A56R, B5R, F12L, and F13L genes.

[18] The virus according to any one of [14] to [17], wherein another vaccinia virus strain having a high EEV productivity is IHD-J strain or IHD-W strain.

[19] A pharmaceutical composition for treating a cancer, comprising the virus according to any one of [14] to [18].

[20] A growth-restricted vaccinia virus vector, which is the virus according to any one of 14 to 18 into which a foreign DNA has been introduced.

[21] The vector according to [20], wherein the foreign DNA is a gene encoding a cancer-specific antigen, an immune response regulator, or a protein with affinity for a cancer cell surface antigen.

The present invention further provides the following [22] to [26].

[22] A method of improving productivity of a growth-restricted vaccinia virus, comprising:

replacing a DNA sequence(s) of a gene(s) encoding an extracellular enveloped virus (EEV)-related protein(s) of the growth-restricted vaccinia virus by a DNA sequence(s) of a corresponding gene(s) of another vaccinia virus strain having a high EEV productivity, wherein the growth-restricted vaccinia virus does not replicate in a normal cell, and can selectively replicate in a proliferating cell.

[23] The method according to [22], wherein the gene(s) encoding the extracellular enveloped virus (EEV)-related protein(s) is one or more genes selected from the group consisting of A33R, A34R, A36R, A56R, B5R, F12L, and F13L.

[24] The method according to [22], wherein the genes encoding the extracellular enveloped virus (EEV)-related proteins are A33R, A36R, A56R, B5R, F12L, and F13L genes.

[25] The method according to [22], wherein the genes encoding the extracellular enveloped virus (EEV)-related proteins are A33R, A34R, A36R, A56R, B5R, F12L, and F13L genes.

[26] The method according to [22], wherein another vaccinia virus strain having a high EEV productivity is IHD-J strain or IHD-W strain.

Effects of the Invention

The present invention can provide an intravenously administrable oncolytic vaccinia virus with improved productivity by impairing the functions of vaccinia virus-derived VGF, ERK and RNR so as to remarkably suppress viral growth in normal cells, thereby improving safety, and by replacing a gene(s) encoding an EEV-related protein(s) of the virus by a corresponding gene(s) of another vaccinia virus strain with a high EEV productivity. The virus can be effectively used as a novel anticancer agent.

BRIEF DESCRIPTION OF THE DRAWINGS

FIG. 1 is a diagram showing the structure of each exemplary recombinant vaccinia virus of the present invention.

FIG. 3 is a graph showing the effects of F4L-deficient modified virus on the cytotoxicity in cancer cells or normal cells. A: HeLa (human cervical carcinoma cells); B: NHDF (normal human dermal fibroblasts).

FIG. 7 is a graph showing the effects of modification of EEV-related proteins on productivity in HeLa cells using a serum-containing medium. Modification is based on (A) MD-RVV and (B) a virus lacking the F4L gene of MD-RVV.

FIG. 8 is a graph showing the effects of modification of EEV-related proteins on productivity in HeLa cells using a chemically-defined culture medium. A: Culture supernatant virus; B: Intracellular virus.

FIG. 9 is a chart showing viral symptom scores of peritoneally metastasized human pancreatic cancer mice after intraperitoneal administration of an RNR gene-deficient virus.

FIG. 10 is a chart showing the survival rates of peritoneally metastasized human pancreatic cancer mice after intraperitoneal administration of an RNR gene-deficient virus.

FIG. 11 is a chart showing viral symptom scores of peritoneally metastasized human pancreatic cancer mice after intraperitoneal administration of an RNR gene-deficient virus.

FIG. 12 is a chart showing the survival rates of peritoneally metastasized human pancreatic cancer mice after intraperitoneal administration of an RNR gene-deficient virus.

FIG. 13 is a chart showing viral symptom scores of orthotopically transplanted human pancreatic cancer mice after intravenous administration of an RNR gene-deficient virus.

FIG. 14 is a chart showing the survival rates of orthotopically transplanted human pancreatic cancer mice after intravenous administration of an RNR gene-deficient virus.

FIG. 15 is a graph showing the tumor volume in subcutaneously transplanted human pancreatic cancer mice after intratumoral administration of an RNR gene-deficient virus.

EMBODIMENTS OF THE INVENTION

The gene nomenclature used herein is those used for the vaccinia virus Copenhagen strain and is also used for homologous genes in other poxvirus families, unless otherwise specified.

The oncolytic virus of the present invention can be prepared as a recombinant vaccinia virus by modifying the vaccinia virus genome. Examples of the parent strain vaccinia virus include Copenhagen, Western Reserve, Lister, LC16mO, LC16m8, TianTan, or Wyeth.

Such a vaccinia virus genome can be modified using, for example, the genome of LC16m8 vaccinia virus, which is a smallpox vaccine strain that has been administered to the human body (Morikawa, S., et al., Journal of General Virology, 79 (18), 11873-11891, 2005). The attenuated strain LC16m8 has a reduced efficiency of virus infection and transmission due to a mutation in the B5R gene, which encodes one of the EEV components of its parent strain LC16mO. It is desirable that the vaccinia virus of the present invention, the replication capacity of which is restricted in normal cells, proliferates and spreads markedly in cancer cells and exhibits strong cytotoxicity.

Thus, for the construction of the oncolytic vaccinia virus, LC16mO or a virus obtained by changing the B5R gene of the LC16m8 virus genome to the DNA sequence of the B5R region of the LC16mO virus may be used.

Figure 2:
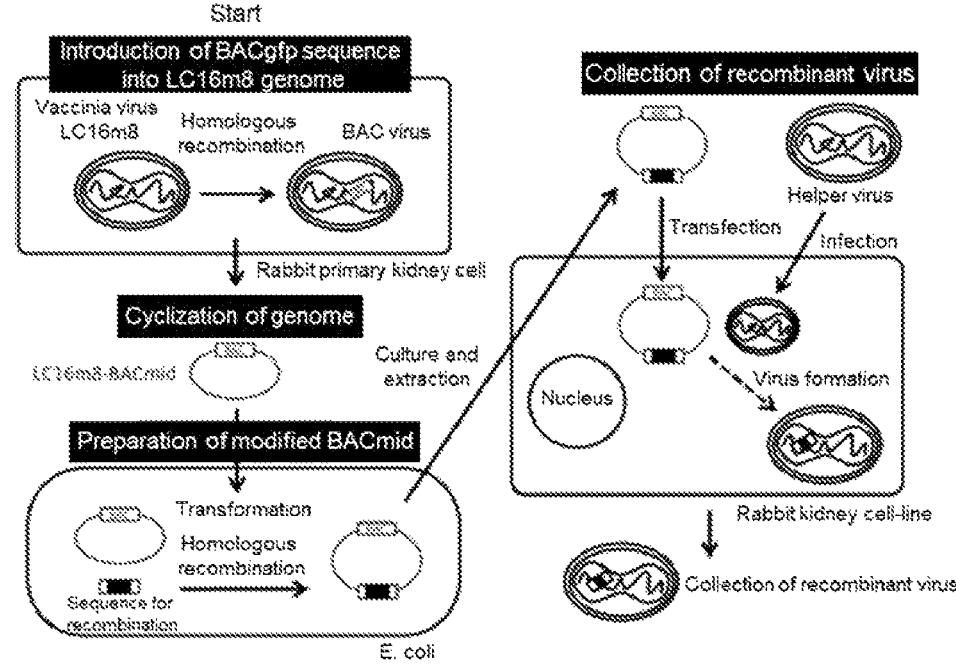
FIG. 2 is a diagram illustrating how to produce an exemplary recombinant vaccinia virus of the present invention.

The vaccinia virus genome can be modified by homologous recombination using a vector. An isolated plasmid containing the modified DNA gene sequence is transfected into cultured cells with vaccinia virus infection. Recombination between the homologous viral DNA of the plasmid and the viral genome produces a modified virus due to the presence of the modified DNA sequence. A Bacterial Artificial Chromosome (BAC) system may be used to modify the vaccinia virus DNA. The BAC system involves a method in which the viral genome having the BACgfp sequence integrated is retained in *Escherichia coli,* and the viral genome is recombined by making use of genetics of *Escherichia coli* (FIG. 2).

The present invention makes it possible to obtain a growth-restricted vaccinia virus that can selectively replicate in proliferating cells and has improved safety by impairing the functions of VGF, ERK-activating protein, and RNR.

The gene encoding VGF is C11R, the gene encoding the O1L protein, which is an ERK-activating protein, is O1L, and the gene encoding RRM2, which is a small subunit of RNR, is F4L. By modifying these genes in the vaccinia virus genome, the functions of VGF, ERK activating protein, and RNR can be impaired.

Deficiency in the functions of VGF, O1L protein, and RRM2 in the vaccinia virus means that the C11R, O1L, and F4L genes are not expressed, or even if they are expressed, the expressed proteins fail to retain the normal functions of VGF, O1L protein, and RRM2. In order to impair the functions of VGF, O1L protein and RRM2, all or part(s) of the C11R, O1L, and F4L genes may be deleted. In addition, each gene may be mutated by nucleotide substitution, deletion, or addition so that neither normal VGF, protein, nor RRM2 can be expressed. In addition, a foreign gene may be inserted into the C11R, O1L, or F4L gene. The foreign gene may be inserted, or the gene may be deleted or mutated by, for example, publicly-known homologous recombination or site-specific mutagenesis. In the present invention, when a normal gene product is not expressed due to a deletion or mutation of the gene, it can be said that the gene is deleted. Deficiency in the C11R, O1L, or F4L gene can be checked by PCR using a primer pair that specifically amplifies each gene.

Further, in addition to impairment of the functions of VGF, ERK-activating protein, and RNR, the gene(s) encoding the EEV-related protein(s) is replaced by the corresponding gene(s) of another vaccinia virus strain having a high EEV productivity. This can improve productivity of a restricted-proliferation vaccinia virus with improved safety.

The gene(s) encoding the EEV-related protein(s) to be modified may be at least one of the genes encoding the seven different proteins (A33R, A34R, A36R, A56R, B5R, F12L, and F13L) that are components of EEV. For example, the productivity of the vaccinia virus can be improved by modifying the gene encoding A34R. It is preferable to modify all of A33R, A36R, A56R, B5R, F12L, and F13L, and it is more preferable to modify all of A33R, A34R, A36R, A56R, B5R, F12L, and F13L.

Examples of the vaccinia virus from which the DNA sequence(s) used to modify the gene(s) encoding the EEV-related protein(s) is derived include, but are not limited to, IHD-J or IHD-W.

In the present invention, in order to improve productivity, a growth-restricted vaccinia virus of interest is obtained by replacing the gene(s) encoding the EEV-related protein(s) by the corresponding gene(s) of another vaccinia virus strain having a high EEV productivity. This vaccinia virus is not particularly limited as long as the growth-restricted vaccinia virus does not replicate in normal cells, and can selectively replicate in proliferating cells. Preferable examples of such a growth-restricted vaccinia virus include, but are not limited to, the above growth-restricted vaccinia virus of the present invention, which has improved safety by impairing the functions of VGF, ERK-activating protein, and RNR. For example, even the virus lacking C11R and O1L (MD-RVV) can have improved productivity by replacing the gene(s) encoding the EEV-related protein(s) by the corresponding gene(s) of another vaccinia virus strain having a high EEV productivity.

FIG. 1 illustrates the modified vaccinia viruses produced according to the present invention.

"LC16m8-B5RmO" is a virus in which the B5R gene of LC16m8 is modified to the DNA sequence of the B5R gene of its parent virus, LC16mO. "MD-RVV" is a virus lacking the C11R and O1L genes of the LC16m8-B5RmO virus.

"MD-RVV-ΔRR" is a virus in which the F4L gene of MD-RVV virus is deleted.

"MD-RVV-A34R" is a virus in which the A34R gene of MD-RVV is replaced with the DNA sequence of the A34R gene of the IHD-J vaccinia virus strain.

"MD-RVV-ΔRR-A34R" is a virus in which the A34R gene of MD-RVV-ΔRR virus is replaced with the DNA sequence of the A34R gene of the IHD-J vaccinia virus strain. "MD-RVV-EEV6" is a virus in which the A33R, A36R, A56R, B5R, F12L, and F13L genes of the MD-RVV virus are replaced with the DNA sequences of the A33R, A36R, A56R, B5R, F12L, and F13L genes of the IHD-J vaccinia virus strain, respectively.

"MD-RVV-ΔRR-EEV6" is a virus in which the A33R, A36R, A56R, B5R, F12L, and F13L genes of the MD-RVV-ΔRR virus are replaced with the DNA sequences of the A33R, A36R, A56R, B5R, F12L, and F13L genes of the IHD-J vaccinia virus strain, respectively.

"MD-RVV-EEV7" is a virus in which the A33R, A34R, A36R, A56R, B5R, F12L, and F13L genes of the MD-RVV virus are replaced with the DNA sequences of the A33R, A34R, A36R, A56R, B5R, F12L, and F13L genes of the IHD-J vaccinia virus strain, respectively. "MD-RVV-ΔRR-EEV7" is a virus in which the A33R, A34R, A36R, A56R, B5R, F12L, and F13L genes of the MD-RVV-ΔRR virus are replaced by the DNA sequences of A33R, A34R, A36R, A56R, B5R, F12L, and F13L genes of the IHD-J vaccinia virus strain, respectively.

As used herein, the "proliferating cell(s)" means a cell(s) having a higher proliferative function than a normal cell(s), and examples thereof include, but are not limited to, a cancer cell(s) or a malignant tumor cell(s).

The growth-restricted vaccinia virus of the present invention can be used in both tumor cells and host cells used for industrial production. The tumor cells mainly mean malignant tumor cells and have the same meaning as cancer cells. Examples of the target cancer cell(s) when classified by an organ of origin include, but are not particularly limited to, a cancer cell(s) of any cancer type such as lung cancer, pancreatic cancer, ovarian cancer, skin cancer, gastric cancer, liver cancer, colon cancer, anal/rectal cancer, esophageal cancer, uterine cancer, breast cancer, bladder cancer, prostate cancer, esophageal cancer, brain/nerve tumor, lymphoma/leukemia, bone/osteosarcoma, smooth muscle myoma, or striated muscle myoma. Examples of the host cells used for industrial production include mammalian cells (e.g., Vero, GL37, CHO, HeLa, MRC-5, huGK-14) used for the production of vaccines or biomedicines.

The growth-restricted vaccinia virus of the present invention can be produced as a pharmaceutical composition by any pharmaceutical method for administering the virus into the body of a mammal including humans. For example, mammalian cells cultured in a bioreactor are used as a host to inoculate and culture the virus of the present invention. Then, the virus of interest is extracted from the cell culture medium, and purified. After that, for example, a pharmaceutically acceptable salt, is added to produce a preparation.

The pharmaceutical composition containing the growth-restricted vaccinia virus of the present invention comprises a pharmaceutically effective amount of the growth-restricted vaccinia virus of the present invention as an active ingredient, and may be in the form of a sterile aqueous or non-aqueous solution, a suspension, or an emulsion. Further, the pharmaceutical composition optionally comprises, for instance, a pharmaceutically acceptable diluent, aid, or carrier (e.g., a salt, a buffer, an adjuvant). The administration method is not particularly limited and the pharmaceutical composition can be administered in vivo using a method known to those skilled in the art. Examples include an intratumoral, intravenous, arterial, intraperitoneal, intracutaneous, subcutaneous, intramuscular, intraventricular, intrathoracic, intraspinal, intraepidermal, or mucosal surface injection. Preferred is intravenous, intraperitoneal, or intratumoral administration. Preferably, the pharmaceutical composition is administered systemically by intravenous administration. In the present invention, systemic oncolytic virus therapy by intravenous administration can be conducted to treat not only primary tumors but also micrometastatic cancers. The effective dose may be determined, if appropriate, depending on the age, gender, health, body weight, etc., of each subject. The effective dose for human adults is not limited and is, for example, about $10^6$-$10^{11}$ plaque-forming units (PFU) and preferably $10^8$-$10^9$ plaque-forming units (PFU) per dosing.

Cells infected with a vaccinia virus produce four viral forms that play distinct roles in the viral life cycle. IMV is the most abundant form of virus, suitable for mediating transmission between hosts due to its physically robust nature. However, IMV is not very suitable for the spread in a host due to its susceptibility to complements and antibodies. IEV acts as an intermediate between IMV and CEV/EEV, ensuring up-take of EEV-specific proteins, transporting virions to the cell surface using microtubules, and covering IMV particles with additional membranes and host proteins to decrease the susceptibility to antibodies and complements. This can widen the range of host receptors that can bind to the vaccinia virus. CEV is required to induce the formation of actin tails from the lower part of virions on the cell surface and promote efficient intercellular transport of the virus. Eventually, EEV is released from the cell surface and mediates the spread of infection in the host (Smith G. L., Journal of General Virology, 83 (Pt 12), 2915-2931, 2002). A virus preparation in the EEV form is desirable for the oncolytic vaccinia virus used for intravenous administration. However, since the morphology of virions changes continuously during the life cycle of the virus, not only EEV released into the culture supernatant during virus culture but also virions such as IMV leaked from cells destroyed by viral proliferation are mixed. From the viewpoint of productivity and physical stability, it is difficult to separate only EEV for production. Thus, modification of EEV-related molecule(s) can contribute to improved efficacy and productivity of the oncolytic virus preparation including various virion forms.

Fragments of cancer cells destroyed by oncolytic viruses are predicted to induce an antitumor immune response specific to autologous cancer. Various viral vectors incorporating genes for cancer-specific antigens and/or immune response regulators have been studied as cancer vaccines. The vaccinia virus has a relatively large viral genome allowing for insertion of the entire gene of the antigenic protein and has an ability to replicate in the cytoplasm rather than in the nucleus of the infected cell. Accordingly, the risk of integration of a genetic material into the genome of the host cell is minimized. Thus, the vaccinia virus is excellent as a viral vector. MVA strain of attenuated vaccinia virus, which has extremely low proliferation capacity in mammalian cells, has been used as a safe viral vector. Oncolytic viruses are attenuated viruses, the growth of which is significantly restricted in normal cells. Use of each oncolytic virus as a viral vector is advantageous in inducing an antitumor immune response (Guo, Z. S., et al., Journal for ImmunoTherapy of Cancer, 7 (1), 6, 2019). The oncolytic vaccinia virus of the present invention can also be used as a vector having a gene insertion. The inserted gene and the insertion site are not particularly limited. For example, there is a method of inserting a gene for a cancer-specific antigen, an immune response regulator, or a protein with affinity for a cancer cell surface antigen into or near the C11R, O1L, or F4L gene, the gene functions of which are to be impaired in the present invention, or into or near an EEV-related gene(s).

The oncolytic virus according to the present invention has improved safety and productivity by deleting C11R, O1L and F4L from the vaccinia virus genome and further substituting the amino acid sequences of a plurality of EEV-related proteins with the amino acid sequences of the IHD-J strain.

Next, the present invention will be described in more detail with reference to Examples. However, the present invention is not limited to these Examples.

EXAMPLE 1

Production of Growth-Restricted Vaccinia Virus by Modifying Genome of Vaccine Strain Vaccinia Virus The genome of LC16m8 vaccinia virus, a smallpox vaccine strain that had been administered to the human body, (Morikawa, S., et al., Journal of General Virology, 79 (18), 11873-11891, 2005) was modified to produce recombinant vaccinia viruses (FIG. 1).

1. Construction of Construct LC16m8-BACmid

The vaccinia virus genome was modified using the BAC system (see FIG. 2). By homologous recombination in cell culture, a BAC virus in which a BACgfp sequence was inserted into the genome of the vaccinia virus LC16m8 strain was prepared, and the BAC virus genome was cyclized to construct LC16m8-BACmid. As the first step, an insertion plasmid (pUC-VVTK-BAC-EGFP) for introducing the BACgfp sequence as a marker into LC16m8 was constructed. The specific method included amplification of TK1 using TK1 primer Fw (SEQ ID NO: 1) and TK1 primer Re (SEQ ID NO: 2) while using the vaccinia virus LC16m8 strain genome (GenBank: AY678275.1) as a template, and amplification of TK2 using the strain genome as a template and TK2 primer Fw (SEQ ID NO: 3) and TK2 primer Re (SEQ ID NO: 4). The TK1 was digested with restriction enzymes KpnI and PacI and the TK2 was digested with restriction enzymes XbaI and PacI. Thereafter, each fragment of interest was purified from an agarose gel.

Next, a pUC119 plasmid (GenBank: U07650.1) was digested with restriction enzymes KpnI and XbaI, and purified. Then, the above two fragments were inserted into the KpnI/XbaI site of the alkaline phosphatase-treated plasmid to construct pUC119-TK1-2. Next, the pUCIDT-KAN-op7.5+EGFP plasmid (SEQ ID NO: 5) was artificially synthesized, digested with a restriction enzyme PacI, and purified. Subsequently, the pUC119-TK1-2 was digested with a restriction enzyme PacI, purified, and then ligated into the PacI site of the alkaline phosphatase-treated plasmid to construct pUC-VVTK-op7.5+EGFP plasmid. Further, a plasmid, in which the pBeloBAC11 sequence (GenBank: CVU51113.1) was inserted into a pBSII plasmid (GenBank: U25267.1), was digested with a restriction enzyme NotI and then purified from an agarose gel. The resulting plasmid was ligated into the NotI site of a plasmid prepared by digesting pUC-VVTK-op7.5+EGFP with a restriction enzyme NotI, purifying, and treating it with alkaline phosphatase. In this way, pUC-VVTK-BAC-EGFP plasmid was constructed.

Next, the following describes how to introduce the BACgfp sequence into the LC16m8 genome. Primary rabbit kidney cells (PRK) were infected with the vaccinia virus LC16m8 strain at MOI=10, and then cultured for 1 h to recover the cells. The recovered cells were suspended in HeBS buffer, and the pUC-VVTK-BAC-EGFP plasmid linearized with a restriction enzyme HindIII was added and then electroporated. The electroporation solution was serially diluted, and PRK, which had been cultured on a 96-well plate, was infected therewith and cultured. Then, the expression of green fluorescent protein (GFP) was observed under a fluorescence microscope. Those having a fluorescence-positive plaque or cytopathic effect (CPE) in wells with a high dilution ratio were selected. The cells of each selected well were collected, sonicated, and centrifuged. Then, the supernatant was obtained as a virus (LC16m8-BACgfp) in which the BACgfp sequence was inserted into LC16m8.

Further, LC16m8-BACmid was constructed by cyclization of the LC16m8-BACgfp genome and cloning into *Escherichia coli* as follows. PRK infected with LC16m8-BACgfp at MOI=5 was transfected with the pCAGGS-Cre plasmid (self-prepared) by using a transfection reagent. Subsequently, LC16m8-BACmid was extracted as a circularized viral genome, and then electroporated into *Escherichia coli* GS1783 (WO2014077096A1). The electroporation solution was cultured on a CG agar medium supplemented with chloramphenicol. After that, *Escherichia coli* carrying LC16m8-BACmid was selected using, as a marker, chloramphenicol resistance in the BACgfp sequence. Finally, each clone of interest was stocked in glycerol.

2. Construction of Modified BACmid

Each modified BACmid was prepared using LC16m8-BACmid as a template. Prepared in advance from cultured cells was a BACgfp-removal sequence cassette (SEQ ID NO: 6) subsequently required for recovering a recombinant virus from which the BACgfp sequence had been removed. How to prepare the BACgfp-removal sequence cassette was as follows. A pUC119 plasmid (GenBank: U07650.1) was digested with restriction enzymes HincII and BamHI, purified, and treated with alkaline phosphatase. Here, a pBSII plasmid (GenBank: U25267.1) was ligated with the pBelo-BAC11 sequence (GenBank: CVU51113.1) to give a plasmid. This plasmid was digested with a restriction enzyme XbaI and purified to give a fragment. This fragment was digested with restriction enzymes ScaI and BglII, and purified. The resulting fragment was ligated with the above plasmid to construct pUC119-pBeloSB. Further, the pUC119-pBeloSB was digested with a restriction enzyme NruI and purified (pUC119-pBeloSB/NruI/elution). Next, by using the vaccinia virus LC16m8 strain genome (GenBank: AY678275.1) as a template, the TK region was amplified using TK primer Fw (SEQ ID NO: 7) and TK primer Re (SEQ ID NO: 8). In addition, by using pEPkan-S plasmid (Addgene) as a template, PCR was performed using kanamycin primer 1Fw (SEQ ID NO: 9) and kanamycin primer 1Re (SEQ ID NO: 10) to amplify the kanamycin resistance gene. The above two PCR products were purified. Three fragments including the pUC119-pBeloSB/NruI/elution were reacted using an In-Fusion HD Cloning Kit (Takara). Then, the reaction solution was introduced into *Escherichia coli* JM109 (Takara). After the reaction, the resulting bacteria were plated on a CG agar medium supplemented with ampicillin, kanamycin, and chloramphenicol to obtain a clone carrying the plasmid of interest (pUC119-BAC-SBTKdup). The pUC119-BAC-SBTKdup plasmid was extracted from the cultured *Escherichia coli,* digested with restriction enzymes PstI and KpnI, and purified to prepare pUC119-BAC-SBTKdup/PstI/KpnI/elution as a BACgfp-removal sequence cassette (SEQ ID NO: 6).

B5R Modification Cassette:

In order to prepare a recombinant virus of interest, an expression cassette of a gene to be modified was prepared by the following protocol. Although the LC16m8 strain is an attenuated virus as a safe vaccine strain, it is desirable to use the LC16mO strain, which is a highly proliferative parent strain in cultured cells, in view of the efficacy of the oncolytic virus. LC16m8 is known to produce an incomplete B5R protein by frameshifting due to a single nucleotide deletion (guanine deletion) in the B5R gene sequence (Morikawa, S., et al., Journal of General Virology, 79(18), 11873-11891, 2005). Then, in order to construct a BACmid in which the B5R gene sequence of LC16m8-BACmid was changed to the sequence of LC16mO having a complete B5R gene sequence, a B5R modification cassette (SEQ ID NO: 11) was prepared by the following protocol. In the B5R gene sequence of LC16mO, about 1 kb each upstream or downstream from the above guanine, totaling 2132 bp, was artificially synthesized to construct pUCFk-B5RmO (SEQ ID NO: 12). This DNA was digested with a restriction enzyme EcoRI, purified, and then treated with alkaline phosphatase (pUCFk-B5RmO/EcoRI/elution/BAP). In addition, PCR was performed using the pEPkan-S plasmid (Addgene) as a template and kanamycin primer 2Fw (SEQ ID NO: 13) and kanamycin primer 2Re (SEQ ID NO: 14) to amplify the kanamycin resistance gene. The post-amplification product was purified, digested with a restriction enzyme EcoRI, and purified to prepare rKanI/EcoRI/elution. Then, pUCFk-B5RmO-rKanI was constructed by ligating the pUCFk-B5RmO/EcoRI/elution/BAP and the rKanI/EcoRI/elution. The pUCFk-B5RmO-rKanI was digested with restriction enzymes XbaI and DraI and then purified to prepare pUCFk-B5RmO-rKanI/XbaI/DraI/elution. This was used as a B5R modification cassette (SEQ ID NO: 11) for modification of the BACmid.

C11R-Deficient Cassette:

A C11R-deficient cassette (SEQ ID NO: 15) was prepared in order to recover a virus lacking the VGF functions. A sequence lacking 255 bp from the start codon of the C11R gene sequence to the restriction enzyme AccI site and about 1 kb fragments before the sequence and after the site were artificially synthesized to construct pUC57-ΔVGF (SEQ ID NO: 16). The pUC57-ΔVGF was digested with a restriction enzyme AccI, purified, and treated with alkaline phosphatase to prepare pUC57-ΔVGF/AccI/elution/BAP. By using the pEPkan-S plasmid (Addgene) as a template, the kanamycin resistance gene was amplified by PCR using kanamycin primer 3Fw (SEQ ID NO: 17) and kanamycin primer 3Re (SEQ ID NO: 18), purified from an agarose gel, and then cloned into a TOPO vector (Invitrogen). The reaction solution was introduced into *Escherichia coli* JM109 (Takara), and a plasmid was extracted from the resulting colonies to produce TOPO-rKanI. The TOPO-rKanI was digested with a restriction enzyme AccI, purified, digested with a restriction enzyme ScaI, and purified from an agarose gel to prepare rKanI/AccI/ScaI/elution. Then, pUC57-ΔVGF-rKanI was constructed by ligating the pUC57-ΔVGF/AccI/elution/BAP and the rKanI/AccI/ScaI/elution. The pUC57-ΔVGF-rKanI was digested with a restriction enzyme ScaI, and further digested with restriction enzymes BamHI and EcoRI. The resulting fragment was purified from an agarose gel, and used as a C11R-deficient cassette (SEQ ID NO: 15) for modification of the BACmid.

O1L-Deficient Cassette:

An O1L-deficient cassette (SEQ ID NO: 19) was prepared in order to recover a virus lacking the O1L functions. A 1049 bp sequence from the start codon of the O1L gene sequence to the restriction enzyme XbaI site was deleted. Next, a sequence in which the kanamycin resistance gene sequence (Addgene) was inserted at 50 bp immediately after the XbaI site was artificially synthesized. In this way, pUC57-ΔO1L-rKanI (SEQ ID NO: 20) was constructed. The pUC57-ΔO1L-rKanI was digested with restriction enzymes ScaI and EcoRI. The resulting fragment was purified from an agarose gel, and used as an O1L-deficient cassette (SEQ ID NO: 19) for modification of the BACmid.

F4L-Deficient Cassette:

A F4L-deficient cassette (SEQ ID NO: 21) was prepared in order to recover a virus lacking the RNR functions. A 765 bp sequence from the start codon of the F4L gene sequence to the EcoRI site was deleted. Next, a sequence in which the kanamycin resistance gene sequence (Addgene) was inserted at 50 bp immediately after the EcoRI site was artificially synthesized. In this way, pUC57-ΔF4L-rKanI (SEQ ID NO: 22) was constructed. The pUC57-ΔF4L-rKanI was digested with restriction enzymes BamHI and HindIII. The resulting fragment was purified from an agarose gel, and used as an F4L-deficient cassette (SEQ ID NO: 21) for modification of the BACmid.

Envelope Modification Cassettes:

To recover a virus obtained in which an EEV-related gene(s) was replaced by the DNA sequence(s) of IHD-J strain or IHD-W strain, each of A33R modification cassette (SEQ ID NO: 23), A34R modification cassette (SEQ ID NO: 24), A36R modification cassette (SEQ ID NO: 25), A33-34-36R modification cassette (SEQ ID NO: 26), A56R modification cassette (SEQ ID NO: 27), B5R modification cassette (SEQ ID NO: 28), or F12-13L modification cassette (SEQ ID NO: 29) was prepared. The specific method included: providing each gene sequence derived from IHD-J strain or IHD-W strain; artificially synthesizing a sequence in which the kanamycin resistance gene sequence (Addgene) was inserted at 50 bp immediately after a specific site; and constructing pUC57-A33R-rKanI (SEQ ID NO: 30), pUC57-A34R-rKanI (SEQ ID NO: 31), pUC57-A36R-rKanI (SEQ ID NO: 32), pUC57-A33-34-36R-rKanI (SEQ ID NO: 33), pUC57-A56R-rKanI (SEQ ID NO: 34), pUC57-B5R-rKanI (SEQ ID NO: 35), or pUC57-F12-13L-rKanI (SEQ ID NO: 36). The pUC57-B5R-rKanI (SEQ ID NO: 35) was digested with restriction enzymes XbaI and BglI. The other constructs were each digested with restriction enzymes BamHI and BglI. Each construct was purified from an agarose gel and used as an envelope modification cassette for modification of each BACmid.

Construction of LC16m8-B5RmO-BACmid:

Construction of LC16m8-B5RmO-BACmid is described below. *Escherichia coli* carrying the above LC16m8-BACmid was cultured, and electroporated with the B5R modification cassette (SEQ ID NO: 11). The electroporation solution was cultured on CG agar medium supplemented with chloramphenicol and kanamycin. Each clone having the cassette introduced was selected by using kanamycin resistance in the cassette as a marker. Further, the kanamycin resistance gene was removed. Then, each clone of interest was obtained by using chloramphenicol resistance given in the BACgfp sequence. A gene fragment of interest was amplified by PCR using a primer pair (SEQ ID NO: 37 and SEQ ID NO: 38), and purified. Then, the nucleotide sequence was analyzed using a sequencing primer (SEQ ID NO: 37). This verified that the obtained clone was the desired modified BACmid (LC16m8-B5RmO-BACmid).

Other modified BACmids were also prepared by substantially the same protocol as above. The band size was checked by PCR using a primer pair specific to the corresponding modification. Each primer pair specific to the corresponding modification was as follows.

C11R deficiency check primer Fw (SEQ ID NO: 39) and C11R deficiency check primer Re (SEQ ID NO: 40);

O1L deficiency check primer Fw (SEQ ID NO: 41) and O1L deficiency check primer Re (SEQ ID NO: 42);

F4L deficiency check primer Fw (SEQ ID NO: 43) and F4L deficiency check primer Re (SEQ ID NO: 44);

A33R modification check primer Fw (SEQ ID NO: 45) and A33R modification check primer Re (SEQ ID NO: 46);

A34R modification check primer Fw (SEQ ID NO: 47) and A34R modification check primer Re (SEQ ID NO: 48);

A36R modification check primer Fw (SEQ ID NO: 49) and A36R modification check primer Re (SEQ ID NO: 50);

A56R modification check primer Fw (SEQ ID NO: 51) and A56R modification check primer Re (SEQ ID NO: 52);

B5R modification check primer Fw (SEQ ID NO: 53) and B5R modification check primer Re (SEQ ID NO: 54); and F12-13L modification check primer Fw (SEQ ID NO: 55) and F12-13L modification check primer Re (SEQ ID NO: 56).

Further, after genome purification, each modification check sequencing primer [A33R modification (SEQ ID NO: 45), A34R modification (SEQ ID NO: 47), A36R modification (SEQ ID NO: 49), A56R modification (SEQ ID NO: 51, SEQ ID NO: 57), B5R modification (SEQ ID NO: 53), or F12-13L modification (SEQ ID NO: 55, SEQ ID NO: 58, SEQ ID NO: 59, SEQ ID NO: 60)] was used for nucleotide sequence analysis to confirm the obtained clone was the desired modified BACmid (MD-RVV-BACmid, MD-RVV-ΔRR-BACmid, MD-RVV-EEV7-BACmid, MD-RVV-EEV6-BACmid, MD-RVV-A34R-BACmid, MD-RVV-ΔRR-EEV7-BACmid, MD-RVV-ΔRR -EEV6-BACmid, or MD-RVV-ΔRR-A34R-BACmid).

A BACgfp-removal sequence cassette (SBTKdup sequence) (SEQ ID NO: 6) was introduced into each modified BACmid in a similar manner. The band size was checked by PCR using a primer pair (BACgfp synthesis primer Fw (SEQ ID NO: 61) and BACgfp synthesis primer Re (SEQ ID NO: 62)). The PCR product was purified and the nucleotide sequence was analyzed using a sequencing primer (SEQ ID NO: 61). Each obtained clone was confirmed to be the desired modified BACmid (MD-RVV-SBTKdup-BACmid, MD-RVV-ΔRR-SBTKdup-BACmid, MD-RVV-EEV7-SBTKdup-BACmid, MD-RVV-EEV6-SBTKdup-BACmid, MD-RVV-A34R-SBTKdup-BACmid, MD-RVV-ΔRR-EEV7-SBTKdup-BACmid, MD-RVV-ΔRR-EEV6-SBTKdup-BACmid, or MD-RVV-ΔRR-A34R-SBTKdup-BACmid).

3. Extraction of Viral Genome

Each BACmid-derived virus, which has a BACgfp-removal sequence cassette, is designed so that BACgfp can be removed while cultured cells are subcultured. Using the above-mentioned BAC virus (LC16m8-BACgfp) as a helper virus, a virus derived from LC16m8-B5RmO-SBTKdup-BACmid was recovered from RK13 cells. RK13 cells cultured on a 6-well plate were inoculated with LC16m8-BACgfp as a helper virus at MOI=1. After culturing for 1 h, the virus was removed and a new culture medium was added. Next, the LC16m8-B5RmO-SBTKdup-BACmid and a transfection reagent were mixed. The mixture was reacted for 15 min, added to cells, and cultured overnight at 37° C. GFP expression was checked under a fluorescence microscope. Then, cells were harvested from a well having a high proportion of GFP fluorescence-negative plaques, frozen and thawed, sonicated, centrifuged to give the supernatant as a virus liquid. The virus liquid was serially diluted with culture medium, inoculated into RK13 cells cultured on a 96-well plate, and cultured at 37° C. for two nights. Then, cells were harvested from a well having a high proportion of GFP fluorescence-negative plaques under a fluorescence microscope, frozen and thawed, sonicated, and centrifuged to give the supernatant as a virus liquid. This procedure was repeated, and virus purification was completed when all the viral plaques in the RK13 cells became fluorescently negative for two consecutive times. The recovered virus was inoculated into RK13 cells cultured on a 6-well plate, and cultured at 37° C. for two nights. After that, the virus genome was extracted using a genome extraction kit. By using the extracted viral genome as a template, PCR was performed using a primer pair (SEQ ID NO: 61 and SEQ ID NO: 62) to verify, from the band size, removal of the BACgfp sequence. Further, the PCR product was purified, and the nucleotide sequence was analyzed using the BACgfp removal check primer (SEQ ID NO: 61) and the B5R guanine insertion check primer (SEQ ID NO: 37). This analysis verified removal of the sequence from the BACgfp sequence insertion site and further insertion of a nucleotide (guanine) at the specific site in the B5R gene sequence, which nucleotide is deleted in LC16m8. The resulting product was used as LC16m8-B5RmO.

Substantially the same protocol as above and LC16m8-BACgfp as a helper virus were used to produce a virus derived from MD-RVV-SBTKdup-BACmid, MD-RVV-ΔRR-SBTKdup-BACmid, MD-RVV-EEV7-SBTKdup-BACmid, MD-RVV-EEV6-SBTKdup-BACmid, MD-RVV-A34R-SBTKdup-BACmid, MD-RVV-ΔRR-EEV7-SBTKdup-BACmid, MD-RVV-ΔRR-EEV6-SBTKdup-BACmid, or MD-RVV-ΔRR-A34R-SBTKdup-BACmid. PCR using the genome extracted therefrom as a template and a specific primer pair was performed to check the band size. Each specific primer pair was as follows.

C11R deficiency check primer Fw (SEQ ID NO: 39) and C11R deficiency check primer Re (SEQ ID NO: 40);

O1L deficiency check primer Fw (SEQ ID NO: 41) and O1L deficiency check primer Re (SEQ ID NO: 42);

F4L deficiency check primer Fw (SEQ ID NO: 43) and F4L deficiency check primer Re (SEQ ID NO: 44);

A33R modification check primer Fw (SEQ ID NO: 45) and A33R modification check primer Re (SEQ ID NO: 46);

A34R modification check primer Fw (SEQ ID NO: 47) and A34R modification check primer Re (SEQ ID NO: 48);

A36R modification check primer Fw (SEQ ID NO: 49) and A36R modification check primer Re (SEQ ID NO: 50);

A56R modification check primer Fw (SEQ ID NO: 51) and A56R modification check primer Re (SEQ ID NO: 52);

B5R modification check primer Fw (SEQ ID NO: 53) and B5R modification check primer Re (SEQ ID NO: 54); and F12-13L modification check primer Fw (SEQ ID NO: 55) and F12-13L modification check primer Re (SEQ ID NO: 56); and BACgfp synthesis primer Fw (SEQ ID NO: 61) and BACgfp synthesis primer Re (SEQ ID NO: 62).

Furthermore, each PCR product was purified and the nucleotide sequence was analyzed using each modification check sequencing primer [A33R modification (SEQ ID NO: 45), A34R modification (SEQ ID NO: 47), A36R modification (SEQ ID NO: 49), A56R modification (SEQ ID NO: 51, SEQ ID NO: 57), B5R modification (SEQ ID NO: 53), F12-13L modification (SEQ ID NO: 55, SEQ ID NO: 58, SEQ ID NO: 59, SEQ ID NO: 60), or BACgfp removal (SEQ ID NO: 61)]. This analysis verified that the obtained each clone was a desired recombinant virus (MD-RVV, MD-RVV-ΔRR, MD-RVV-EEV7, MD-RVV-EEV6, MD-RVV-A34R, MD-RVV-ΔRR-EEV7, MD-RVV-ΔRR-EEV6, or MD-RVV-ΔRR-A34R).

EXAMPLE 2

Decrease in Cytotoxicity in Normal Cells by RNR Gene Deficiency

Cultured cells derived from cancer cells or normal cells were infected with MD-RVV, an oncolytic vaccinia virus lacking the C11R and O1L genes, or its EEV-related gene-modified viruses, or their modified viruses lacking the F4L gene encoding a small subunit of ribonucleotide reductase (RNR) and was present in their viral genomes. Then, the cytotoxicity was evaluated using a Cell Counting Kit-8 (DOJINDO LABORATORIES). Cancer cells (human cervical carcinoma-derived cell line: HeLa cells) and normal cells (normal human dermal fibroblasts: NHDF) were seeded on a 96-well plate and subjected to adhesion culture in a serum-containing medium. Next, the respective cells were cultured serum-starvedly in a serum-free medium and inoculated with a low level ($0.8\times10^6$ PFU/mL) or a high level ($4.0\times10^6$ PFU/mL) of each virus selected from LC16m8-B5RmO, MD-RVV, MD-RVV-ΔRR, MD-RVV-ΔRR-A34R, MD-RVV-ΔRR-EEV6, or MD-RVV-ΔRR-EEV7. After 72 h, a cell counting kit was used to quantify the cell viability of each virus inoculation group while the absorbance of the control group without virus inoculation was set to 100%. The results are shown in FIG. 3. All the viruses used here showed similar cytotoxicity to cancer cells (FIG. 3A), however the virus toxicity to the normal cells was significantly reduced in the F4L gene-deficient virus (ΔRR) (FIG. 3B).

EXAMPLE 3

Figure 4:
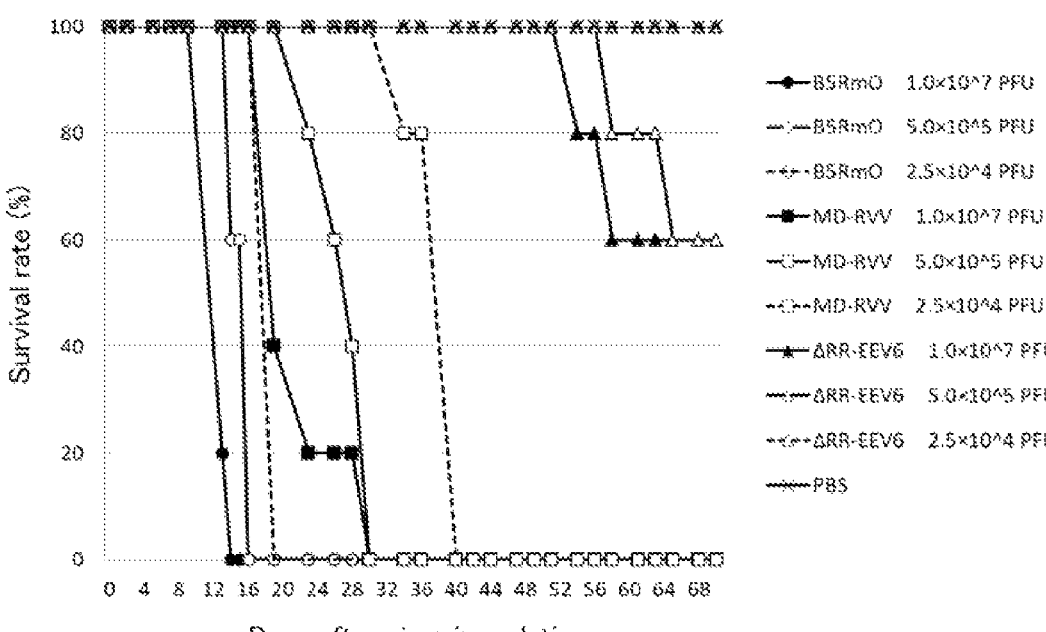
FIG. 4 is a chart showing the survival rates of immunodeficient mice intravenously administered with F4L-deficient modified viruses.
Figure 5:
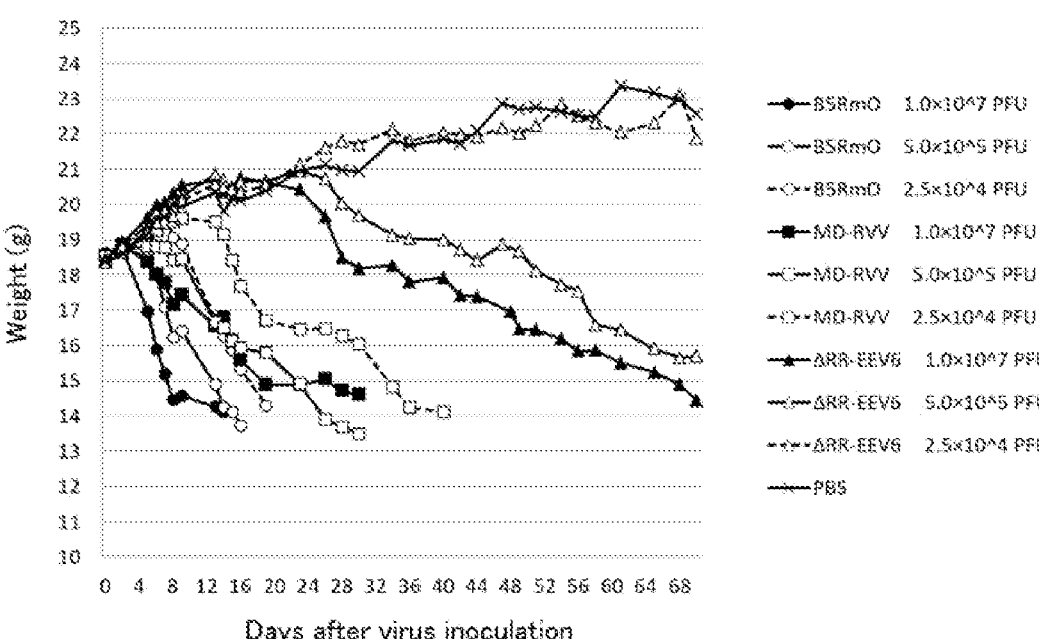
FIG. 5 is a chart showing body weight changes in immunodeficient mice intravenously administered with F4L-deficient modified viruses.
Figure 6:
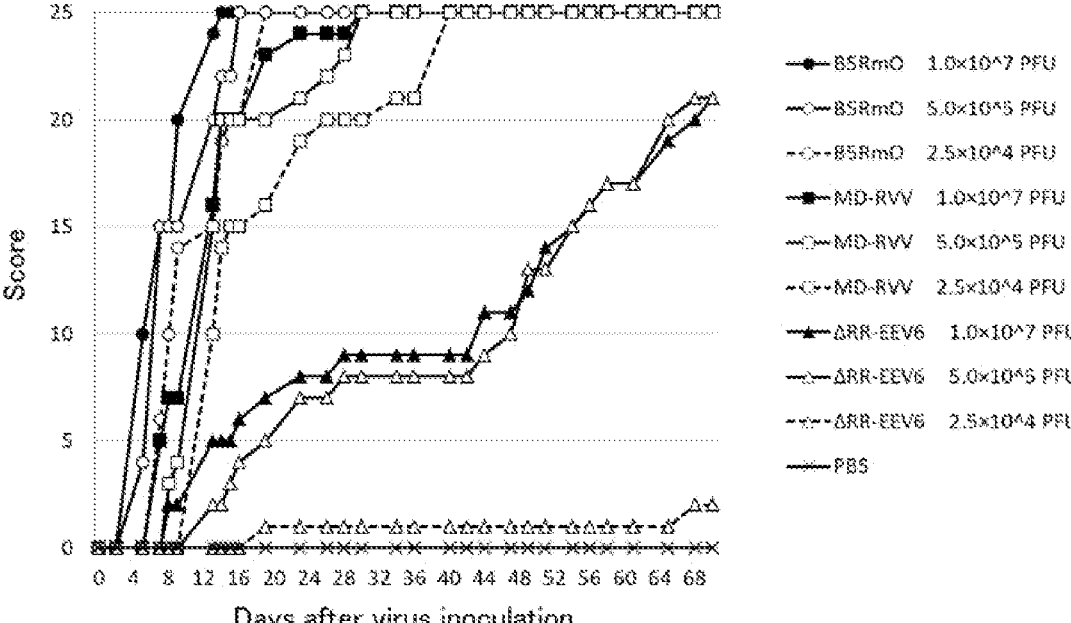
FIG. 6 is a chart showing changes in the state of immunodeficient mice intravenously administered with F4L-deficient modified viruses.

Decrease in Virus Toxicity After Intravenous Administration to Immunodeficient Mice by RNR Gene Deficiency Immunodeficient mice (SCID mice, 5 weeks old, female, 5 in each group) were given LC16m8-B5RmO, MD-RVV, MD-RVV-ΔRR-EEV6 at $2.5\times10^4$, $5\times10^5$, or $1\times10^7$ PFU/0.1 mL. The dose was intravenously administered to the mice, and the number of survivors, the body weight, and the viral symptom score were recorded. The viral symptom score is up to 5 points as follows: 0 points: no symptoms; 1 point: 1-2 smallpox lesions; 2 points: 3-4 smallpox lesions; 3 points: many smallpox lesions, a rough coat, piloerection; 4 Points: dyspnea, dying; and 5 points: death. The results are shown in FIGS. 4 to 6. In the LC16m8-B5RmO and MD-RVV administration groups, animals in all dose groups died by 19 and 40 days after virus administration, respectively. However, for MD-RVV-ΔRR-EEV6, 3 out of 5 animals in the high-dose and medium-dose groups survived until 71 days when the observation was completed. In addition, all animals were alive in the low-dose group (FIG. 4). It was observed that both viruses caused a weight loss in a dose-dependent manner. The degree of weight loss was greater in the order from MD-RVV-ΔRR-EEV6 to MD-RVV to LC16m8-B5RmO (smaller to greater) (FIG. 5). The viral symptom score also depended on the dose and became higher in the order from MD-RVV-ΔRR-EEV6 to MD-RVV to LC16m8-B5RmO (lower to higher) (FIG. 6).

EXAMPLE 4

Increase in Productivity in Cancer Cells by Modifying EEV-Related Protein(s)

HeLa cells were seeded on a 24-well plate and subjected to adherent culture in a serum-containing culture medium. Next, the cells were inoculated with MD-RVV, MD-RVV-A34R, MD-RVV-EEV6, MD-RVV-EEV7, MD-RVV-ΔRR, MD-RVV-ΔRR-A34R, MD-RVV-ΔRR-EEV6, or MD-RVV-ΔRR-EEV7 at MOI=1. After culturing for 1 h, the virus was removed and a fresh serum-containing culture medium was added. The culture medium was collected after 16, 24, 32, or 48 h to obtain each virus in the culture supernatant. The recovered virus was serially diluted, inoculated into RK13 cells cultured on a 6-well plate, and cultured for 1 h. Then, the virus was removed, and a methylcellulose medium was newly added. After culturing at 37° C. for 72 h, plaques were counted to calculate the infectivity titer. The results are shown in FIG. 7. This demonstrated that, compared with an EEV-related protein(s) was modified in MD-RVV (FIG. 7A) or the virus lacking the F4L gene in MD-RVV (FIG. 7B), any of the modified viruses exhibited a tendency of increasing the amount of production of each virus in the culture supernatant throughout the culturing period. In particular, the greater the number of modifications of EEV-related proteins, the greater the effect.

In addition, HeLa cells were seeded on a 24-well plate and subjected to adherent culture in a serum-containing culture medium. Next, the cells were cultured in a chemically defined culture medium and inoculated with LC16m8-B5RmO, MD-RVV-ΔRR, MD-RVV-ΔRR-A34R, MD-RVV-ΔRR-EEV6, or MD-RVV-ΔRR-EEV7 at MOI=0.01. After culturing for 1 h, the virus was removed and a fresh chemically defined culture medium was added. The culture medium was collected after 48 h to obtain each virus in the culture supernatant. Further, the cells were collected, frozen and thawed, sonicated, and centrifuged to obtain an intracellular virus in the supernatant. The recovered virus was serially diluted, inoculated into RK13 cells cultured on a 6-well plate, and cultured for 1 h. Then, the virus was removed, and a methylcellulose medium was newly added. After culturing at 37° C. for 72 h, plaques were counted to calculate the infectivity titer. The results are shown in FIG. 8. Modification of the EEV-related protein(s) caused a tendency to regain the virus production decreased due to the deletion of the RNR gene in both the culture supernatant virus (FIG. 8A) and the intracellular virus (FIG. 8B). In particular, the greater the number of modifications of EEV-related proteins, the greater the effect.

EXAMPLE 5

Effects of RNR Gene-Deficient Virus Intraperitoneally Administered to Peritoneally Metastasized Human Pancreatic Cancer Mice It was checked whether the RNR gene-deficient virus elicited a survival-prolonging effect on peritoneally metastasized model mice when administered intraperitoneally. For this purpose, peritoneally metastasized human pancreatic cancer mice were established by transplanting $3\times10^6$ human pancreatic cancer BxPC3-Luc cells into the abdominal cavity of each immunodeficient mouse (SCID mice, 6 weeks old, female). Then, 21 days later, MD-RVV or MD-RVV-ΔRR-EEV6 ($10^5$ PFU/0.1 mL) was intraperitoneally administered to the mice. In addition, PBS (0.1 mL) was intraperitoneally administered to the virus-non-administration group as a control the same 21 days later. After administration, the virus toxicity and the number of survivors were recorded. In addition, the virus toxicity was determined by scoring the symptoms with a maximum of 5 points as follows: 0 points: no symptoms; 1 point: 1-2 smallpox (pox) lesions; 2 points: 3-4 smallpox (pox) lesions; 3 points: many smallpox (pox) lesions, a rough coat, piloerection; 4 points:

dyspnea, dying; and 5 points: virus-related death. The results are shown in FIGS. 9 to 10 (FIG. 9: viral symptom score; FIG. 10: survival rate).

Regarding the virus toxicity, the MD-RVV-administration group manifested symptoms of smallpox (pox) from about 10 days after administration, and after that, severe viral symptoms such as an increased number of smallpox (pox) lesions, a rough coat, and dyspnea were developed. At last, by day 42, all cases died from their virus toxicity (FIG. 9). By contrast, the MD-RVV-ΔRR-EEV6 administration group showed no viral symptoms. This has demonstrated an effect of improving safety by the RNR gene deficiency (FIG. 9).

In the evaluation based on the number of survivors, the MD-RVV-administration group was accompanied by severe virus toxicity and all cases died at the same time as in the case of the virus-non-administration group in which the tumor grew (FIG. 10). By contrast, in the log-rank test for testing the difference in survival period, the MD-RVV-ΔRR-EEV6 administration group had a significant survival-prolonging effect when compared to the virus-non-administration group and the MD-RVV administration group (FIG. 10).

Subsequently, peritoneally metastasized human pancreatic cancer mice were established by transplanting different $3 \times 10^6$ human pancreatic cancer MIA-PaCa2/CMV-Luc cells into the abdominal cavity of each immunodeficient mouse (SCID mice, 6 weeks old, female). Then, 14 days later, MD-RVV ($10^6$ PFU/0.1 mL) or MD-RVV-ΔRR-EEV6 ($10^6$ or $10^7$ PFU/0.1 mL) was intraperitoneally administered to the mice. In addition, PBS (0.1 mL) was intraperitoneally administered to the virus-non-administration group the same 14 days later. After administration, the virus toxicity and the number of survivors were recorded. In addition, the virus toxicity was determined by scoring the symptoms with a maximum of 5 points as follows: 0 points: no symptoms; 1 point: 1-2 smallpox (pox) lesions; 2 points: 3-4 smallpox (pox) lesions; 3 points: many smallpox (pox) lesions, a rough coat, piloerection; 4 points: dyspnea, dying; and 5 points: virus-related death. The results are shown in FIGS. 11 and 12 (FIG. 11: viral symptom score, FIG. 12: survival rate).

Regarding the virus toxicity in the MD-RVV-administration group, a variation was observed between individuals with marked viral symptoms and individuals without them, however overall, moderate to severe viral symptoms were observed (FIG. 11). By contrast, the MD-RVV-ΔRR-EEV6 administration group showed no viral symptoms. This has demonstrated an effect of improving safety by the RNR gene deficiency (FIG. 11).

In the evaluation based on the number of survivors, all cases in the MD-RVV-administration group died at the same time as in the case of the non-virus-inoculation group due to severe virus toxicity and tumor growth (FIG. 12). By contrast, the MD-RVV-ΔRR-EEV6-administration group showed a dose-dependent tendency to prolong survival when compared to the virus-non-administration group and the MD-RVV-administration group (FIG. 12).

The above results have suggested that the RNR gene-deficient virus is a highly safe oncolytic virus that can be administered intraperitoneally.

EXAMPLE 6

Figure 13:
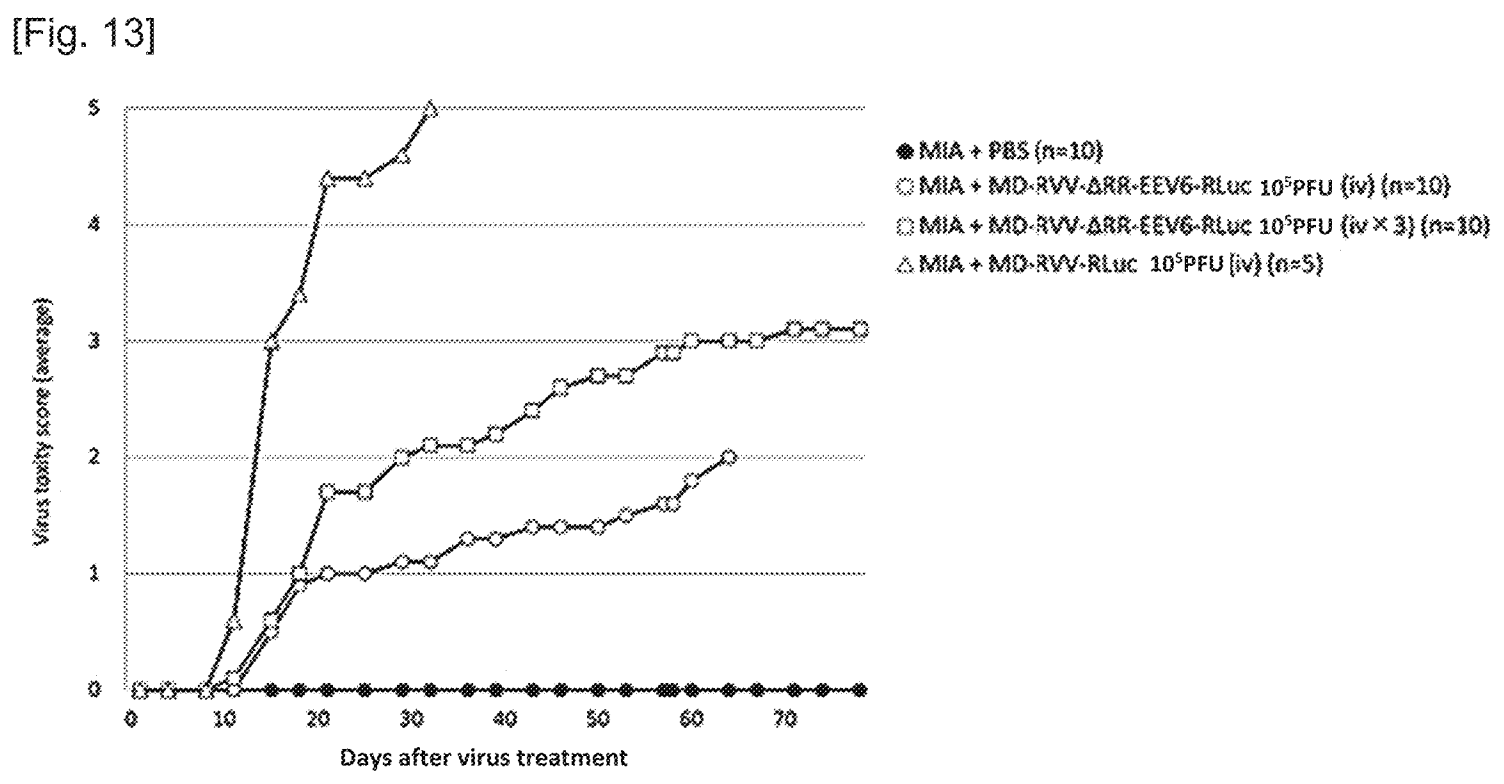

Effects of RNR Gene-Deficient Virus Intravenously Administered to Orthotopically Transplanted Human Pancreatic Cancer Mice It was checked whether the RNR gene-deficient virus elicited a survival-prolonging effect on pancreatic cancer model mice when administered intravenously. For this purpose, orthotopically transplanted human pancreatic cancer mice were established by transplanting $1 \times 10^6$ human pancreatic cancer MIA-PaCa2/CMV-Luc cells into the pancreatic membrane of each immunodeficient mouse (SCID mice, 5 weeks old, female). Then, 12 days later, MD-RVV-RLuc ($10^5$ PFU/0.1 mL) or MD-RVV-ΔRR-EEV6-RLuc ($10^5$ PFU/0.1 mL) was intravenously administered to the mice. Note that RLuc means a Renilla luciferase gene. To check the in vivo distribution of the virus in the future, a RLuc expression cassette (SEQ ID NO: 63) was constructed. Then, the cassette was inserted immediately before the C11R-AccI site after the deletion in Example 1. In addition, MD-RVV-ΔRR-EEV6-RLuc was additionally administered twice within 1 week after the first administration (frequent administration). Further, PBS (0.1 mL) was intravenously administered to the virus-non-administration group the same 12 days later. After administration, the virus toxicity and the number of survivors were recorded. In addition, the virus toxicity was determined by scoring the symptoms with a maximum of 5 points as follows: 0 points: no symptoms; 1 point: 1-2 smallpox (pox) lesions; 2 points: 3-4 smallpox (pox) lesions; 3 points: many smallpox (pox) lesions, a rough coat, piloerection; 4 points: dyspnea, dying; and 5 points: virus-related death. The results are shown in FIGS. 13 and (FIG. 13: viral symptom score, FIG. 14: survival rate).

Regarding the virus toxicity, the MD-RVV-RLuc-administration group manifested symptoms of smallpox (pox) from about 10 days after administration, and after that, severe viral symptoms such as an increased number of smallpox (pox) lesions, a rough coat, and dyspnea were developed. At last, by day 32, all cases died from their virus toxicity accompanied (FIG. 13). By contrast, in the MD-RVV-ΔRR-EEV6-RLuc administration group, some viral symptoms were recognized after both single and frequent administrations, however no fatal symptoms were observed. An effect of improving safety by the RNR gene deficiency was demonstrated (FIG. 13).

In the evaluation based on the number of survivors, all cases in the MD-RVV-RLuc-administration group died of severe virus toxicity at a time earlier than in the case of the virus-non-administration group in which the tumor grew (FIG. 14). By contrast, in the log-rank test for testing the difference in survival period, the MD-RVV-ΔRR-EEV6-RLuc single administration group had substantially the same change in the survival as the virus-non-administration group. However, the frequent administration group elicited a more significant survival-prolonging effect than the virus-non-administration group (FIG. 14).

The above results have suggested that the RNR gene-deficient virus is a highly safe oncolytic virus that can be administered intravenously and frequently.

EXAMPLE 7

Effects of RNR Gene-Deficient Virus Intratumorally Administered to Subcutaneously Transplanted Human Pancreatic Cancer Mice It was checked whether the RNR gene-deficient virus exerted an effect of suppressing tumor growth when administered intratumorally. For this purpose, $5 \times 10^6$ human pancreatic cancer MIA-PaCa2/CMV-Luc cells were transplanted subcutaneously in the right femur of each immunodeficient mouse (SCID mice, 6 weeks old, female). The MD-RVV-ΔRR-EEV6-RLuc ($10^4$, $10^5$, or $10^6$ PFU/0.1 mL) was intratumorally administered to individuals, the tumor volume of which reached 100 mm³ or larger. In addition, PBS (0.1 mL) was intratumorally administered to the virus-non-administration group. After administration, a change in the tumor volume was recorded. The tumor volume was calculated by minor axis×minor axis×major axis×1/2.

Regarding the change in the tumor volume, the MD-RVV-ΔRR-EEV6-RLuc showed a tendency to suppress the tumor growth in an approximately dose-dependent manner. An effect of suppressing the tumor growth after intratumoral administration was demonstrated (FIG. 15).

The results of Examples 5 to 7 have suggested that the RNR gene-deficient viruses MD-RVV-ΔRR-EEV6 and MD-RVV-ΔRR-EEV6-RLuc exerted their intrinsic onco-lytic effect in different human pancreatic cancer mice, thereby eliciting a survival-prolonging effect while the safety is secured.

Sequence List Free Text

SEQ ID NO: 1 is the nucleotide sequence of TK1 primer Fw.

SEQ ID NO: 2 is the nucleotide sequence of TK1 primer Re.

SEQ ID NO: 3 is the nucleotide sequence of TK2 primer Fw.

SEQ ID NO: 4 is the nucleotide sequence of TK2 primer Re. SEQ ID NO: 5 is the nucleotide sequence of the pUCIDT-KAN-op7.5+EGFP plasmid.

SEQ ID NO: 6 is the nucleotide sequence of the BACgfp-removal sequence cassette.

SEQ ID NO: 7 is the nucleotide sequence of TK primer Fw.

SEQ ID NO: 8 is the nucleotide sequence of TK primer Re.

SEQ ID NO: 9 is the nucleotide sequence of kanamycin primer 1Fw.

SEQ ID NO: 10 is the nucleotide sequence of kanamycin primer 1Re.

SEQ ID NO: 11 is the nucleotide sequence of the B5R modification cassette.

SEQ ID NO: 12 is the nucleotide sequence of pUCFk-B5RmO.

SEQ ID NO: 13 is the nucleotide sequence of kanamycin primer 2Fw.

SEQ ID NO: 14 is the nucleotide sequence of kanamycin primer 2Re.

SEQ ID NO: 15 is the nucleotide sequence of the C11R-deficient cassette.

SEQ ID NO: 16 is the nucleotide sequence of pUC57-ΔVGF.

SEQ ID NO: 17 is the nucleotide sequence of kanamycin primer 3Fw.

SEQ ID NO: 18 is the nucleotide sequence of kanamycin primer 3Re.

SEQ ID NO: 19 is the nucleotide sequence of the O1L-deficient cassette.

SEQ ID NO: 20 is the nucleotide sequence of pUC57-ΔO1L-rKanI.

SEQ ID NO: 21 is the nucleotide sequence of the F4L-deficient cassette.

SEQ ID NO: 22 is the nucleotide sequence of pUC57-ΔF4L-rKanI.

SEQ ID NO: 23 is the nucleotide sequence of the A33R modification cassette.

SEQ ID NO: 24 is the nucleotide sequence of the A34R modification cassette.

SEQ ID NO: 25 is the nucleotide sequence of the A36R modification cassette.

SEQ ID NO: 26 is the nucleotide sequence of the A33-34-36R modification cassette.

SEQ ID NO: 27 is the nucleotide sequence of the A56R modification cassette.

SEQ ID NO: 28 is the nucleotide sequence of the B5R modification cassette.

SEQ ID NO: 29 is the nucleotide sequence of the F12-13L modification cassette.

SEQ ID NO: 30 is the nucleotide sequence of pUC57-A33R-rKanI.

SEQ ID NO: 31 is the nucleotide sequence of pUC57-A34R-rKanI.

SEQ ID NO: 32 is the nucleotide sequence of pUC57-A36R-rKanI.

SEQ ID NO: 33 is the nucleotide sequence of pUC57-A33-34-36R-rKanI.

SEQ ID NO: 34 is the nucleotide sequence of pUC57-A56R-rKanI. SEQ ID NO: 35 is the nucleotide sequence of pUC57-B5R-rKanI.

SEQ ID NO: 36 is the nucleotide sequence of pUC57-F12-13L-rKanI.

SEQ ID NO: 37 is the nucleotide sequence of the B5R modification check primer Fw.

SEQ ID NO: 38 is the nucleotide sequence of B5R modification check primer Re.

SEQ ID NO: 39 is the nucleotide sequence of the C11R deficiency check primer Fw.

SEQ ID NO: 40 is the nucleotide sequence of the C11R deficiency check primer Re.

SEQ ID NO: 41 is the nucleotide sequence of the O1L deficiency check primer Fw.

SEQ ID NO: 42 is the nucleotide sequence of the O1L deficiency check primer Re.

SEQ ID NO: 43 is the nucleotide sequence of the F4L deficiency check primer Fw.

SEQ ID NO: 44 represents the nucleotide sequence of the F4L deletion check primer Re.

SEQ ID NO: 45 represents the nucleotide sequence of the A33R modification check primer Fw.

SEQ ID NO: 46 represents the nucleotide sequence of the A33R modification check primer Re.

SEQ ID NO: 47 represents the nucleotide sequence of the A34R modification check primer Fw.

SEQ ID NO: 48 represents the nucleotide sequence of the A34R modification check primer Re.

SEQ ID NO: 49 represents the nucleotide sequence of the A36R modification check primer Fw.

SEQ ID NO: 50 represents the nucleotide sequence of the A36R modification check primer Re.

SEQ ID NO: 51 represents the nucleotide sequence of the A56R modification check primer Fw.

SEQ ID NO: 52 represents the nucleotide sequence of the A56R modification check primer Re.

SEQ ID NO: 53 represents the nucleotide sequence of the B5R modification check primer Fw.

SEQ ID NO: 54 represents the nucleotide sequence of the B5R modification check primer Re.

SEQ ID NO: 55 represents the nucleotide sequence of the F12-13L modification check primer Fw.

SEQ ID NO: 56 represents the nucleotide sequence of the F12-13L modification check primer Re.

SEQ ID NO: 57 represents the nucleotide sequence of the A56R modification check primer Fw.

SEQ ID NO: 58 represents the nucleotide sequence of the F12-13L modification check primer Fw.

SEQ ID NO: 59 represents the nucleotide sequence of the F12-13L modification check primer Fw.

SEQ ID NO: 60 represents the nucleotide sequence of the F12-13L modification check primer Fw.

SEQ ID NO: 61 represents the nucleotide sequence of the BACgfp synthesis primer Fw.

SEQ ID NO: 62 represents the nucleotide sequence of the BACgfp synthesis primer Re.

SEQ ID NO: 63 represents the nucleotide sequence of the RLuc expression cassette.

---

The invention claimed is:

1. A vaccinia virus deficient in functions of vaccinia virus growth factor (VGF), extracellular signal-regulated kinase (ERK)-activating protein, and ribonucleotide reductase (RNR), wherein all or part of regions of each of C11R, O1L, and F4L genes have been deleted or modified, and the functions of these gene products have been inactivated;

wherein genes encoding extracellular enveloped virus (EEV)-related proteins are replaced by a corresponding genes of another vaccinia virus strain having a high EEV productivity;

wherein the genes encoding the extracellular enveloped virus (EEV)-related proteins are A33R, A36R, A56R, B5R, F12L, and F13L, and have been replaced by corresponding genes of another vaccinia virus strain having a high EEV productivity, wherein the corresponding genes of another vaccinia virus strain having a high EEV productivity are genes encoding the same amino acid sequence as those of EEV-related proteins selected from the group consisting of A33R, A36R, A56R, B5R, F12L, and F13L being present in vaccinia virus IHD-J strain or IHD-W strain; or wherein the genes encoding the extracellular enveloped virus (EEV)-related proteins are A33R, A34R, A36R, A56R, B5R, F12L, and F13L, and have been replaced by corresponding genes of another vaccinia virus strain having a high EEV productivity, wherein the corresponding genes of another vaccinia virus strain having a high EEV productivity are genes encoding the same amino acid sequence as those of EEV-related proteins selected from the group consisting of A33R, A34R, A36R, A56R, B5R, F12L, and F13L being present in vaccinia virus IHD-J strain or IHD-W strain.

2. The virus according to claim 1, which is a growth-restricted virus having improved safety, wherein the virus does not replicate in a normal cell and can selectively replicate in a proliferating cell.

3. The virus according to claim 1, wherein the genes encoding the extracellular enveloped virus (EEV)-related proteins are A33R, A36R, A56R, B5R, F12L, and F13L, and have been replaced by corresponding genes of another vaccinia virus strain having a high EEV productivity, wherein the corresponding genes of another vaccinia virus strain having a high EEV productivity are genes encoding the same amino acid sequence as those of EEV-related proteins selected from the group consisting of A33R, A36R, A56R, B5R, F12L, and F13L being present in vaccinia virus IHD-J strain or IHD-W strain.

4. The virus according to claim 1, wherein the genes encoding the extracellular enveloped virus (EEV)-related proteins are A33R, A34R, A36R, A56R, B5R, F12L, and F13L, and have been replaced by corresponding genes of another vaccinia virus strain having a high EEV productivity, wherein the corresponding genes of another vaccinia virus strain having a high EEV productivity are genes encoding the same amino acid sequence as those of EEV-related proteins selected from the group consisting of A33R, A34R, A36R, A56R, B5R, F12L, and F13L being present in vaccinia virus IHD-J strain or IHD-W strain.

5. A pharmaceutical composition for treating a cancer, comprising the virus according to claim 1.

6. The pharmaceutical composition according to claim 5, which is for intravenous administration, intraperitoneal administration, or intratumoral administration.

7. A growth-restricted vaccinia virus vector, which is the virus according to claim 1 into which a foreign DNA has been introduced.

8. The vector according to claim 7, wherein the foreign DNA is a gene encoding a cancer-specific antigen, an immune response regulator, or a protein with affinity for a cancer cell surface antigen.

9. A method of improving productivity of a growth-restricted vaccinia virus, comprising: replacing DNA sequences of genes encoding extracellular enveloped virus (EEV)-related proteins of the growth-restricted vaccinia virus by DNA sequences of corresponding genes of another vaccinia virus strain having a high EEV productivity, wherein the growth-restricted vaccinia virus does not replicate in a normal cell, and can selectively replicate in a proliferating cell, the growth-restricted vaccinia virus deficient in functions of vaccinia virus growth factor (VGF), extracellular signal- regulated kinase (ERK)-activating protein, and ribonucleotide reductase (RNR), wherein all or part of regions of each of C11R, O1L, and F4L genes have been deleted or modified, and the functions of these gene products have been inactivated-, wherein the genes encoding the extracellular enveloped virus (EEV)-related proteins are A33R, A36R, A56R, B5R, F12L, and F13L genes or wherein the genes encoding the extracellular enveloped virus (EEV)-related proteins are A33R, A34R, A36R, A56R, B5R, F12L, and F13L genes and have been replaced by corresponding genes of another vaccinia virus strain having a high EEV productivity, and wherein the corresponding genes of another vaccinia virus strain having a high EEV productivity are genes encoding the same amino acid sequence as those of EEV-related proteins selected from the group consisting of A33R, A34R, A36R, A56R, B5R, F12L, and F13L being present in vaccinia virus IHD-J strain or IHD-W strain.

10. The method according to claim 9, wherein the genes encoding the extracellular enveloped virus (EEV)-related proteins are A33R, A36R, A56R, B5R, F12L, and F13L genes.

11. The method according to claim 9, wherein the genes encoding the extracellular enveloped virus (EEV)-related proteins are A33R, A34R, A36R, A56R, B5R, F12L, and F13L genes.

* * * * *